(12) United States Patent
Ogura

(10) Patent No.: US 10,905,389 B2
(45) Date of Patent: *Feb. 2, 2021

(54) MOBILE RADIATION GENERATION APPARATUS

(71) Applicant: FUJIFILM Corporation, Tokyo (JP)

(72) Inventor: Ryosuke Ogura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 142 days.

This patent is subject to a terminal disclaimer.

(21) Appl. No.: 16/137,490

(22) Filed: Sep. 20, 2018

(65) Prior Publication Data

US 2019/0029619 A1   Jan. 31, 2019

Related U.S. Application Data

(63) Continuation of application No. PCT/JP2017/011079, filed on Mar. 21, 2017.

(30) Foreign Application Priority Data

Apr. 7, 2016  (JP) ................... 2016-077631

(51) Int. Cl.
  *A61B 6/00* (2006.01)
  *A61B 6/10* (2006.01)

(52) U.S. Cl.
  CPC ............ *A61B 6/4405* (2013.01); *A61B 6/105* (2013.01)

(58) Field of Classification Search
  CPC ......... A61B 6/10; A61B 6/105; A61B 6/4405; A61B 6/4429
  See application file for complete search history.

(56) References Cited

U.S. PATENT DOCUMENTS 3,187,845 A  *  6/1965  Ashley, Jr. ................ B60T 7/02
                                                       188/16
5,503,416 A  *  4/1996  Aoki .................... A61B 6/4405
                                                       16/35 R
(Continued)

FOREIGN PATENT DOCUMENTS

DE           3900312 A1  *  2/1990  .......... A61B 6/4405
JP       H02112578          9/1990
(Continued)

OTHER PUBLICATIONS

"Written Opinion of the International Searching Authority (Form PCT/ISA/237) of PCT/JP2017/011079," dated Jun. 13, 2017, with English translation thereof, pp. 1-6.
(Continued)

*Primary Examiner* — Chih-Cheng Kao
(74) *Attorney, Agent, or Firm* — JCIPRNET

(57) ABSTRACT

Provided is a mobile radiation generation apparatus which reliably prevents the unsteady motion of a carriage unit with a simple structure and facilitates the fine adjustment of the position of a radiation emitting unit. Each of a front wheel and a rear wheel of a carriage unit is a caster that swivels about a swivel axis extending in a vertical direction. A support that vertically stands on the carriage unit supports a base end of an arm unit having a free end to which an X-ray emitting unit is attached. The arm unit rotates about a rotation axis parallel to the swivel axis with respect to the carriage unit. The carriage unit includes a front pedal that is provided closer to the front wheel than the support and is used to lock both the rotation and swivel of the caster at the same time.

18 Claims, 41 Drawing Sheets

(56) References Cited

U.S. PATENT DOCUMENTS

| 6,421,854 B1* | 7/2002 | Heimbrock ............ A61G 13/06 |
| | | 280/43.17 |
| 6,609,826 B1 | 8/2003 | Fujii et al. |
| 2015/0078527 A1* | 3/2015 | Iwamoto .............. A61B 6/4405 |
| | | 378/91 |

FOREIGN PATENT DOCUMENTS

| JP | H08091222 | 4/1996 |
| JP | 2005131157 | 5/2005 |
| JP | 2010214126 | 9/2010 |

OTHER PUBLICATIONS

"International Search Report (Form PCT/ISA/210) of PCT/JP2017/011079," dated Jun. 13, 2017, with English translation thereof, pp. 1-3.

* cited by examiner

FIG. 8
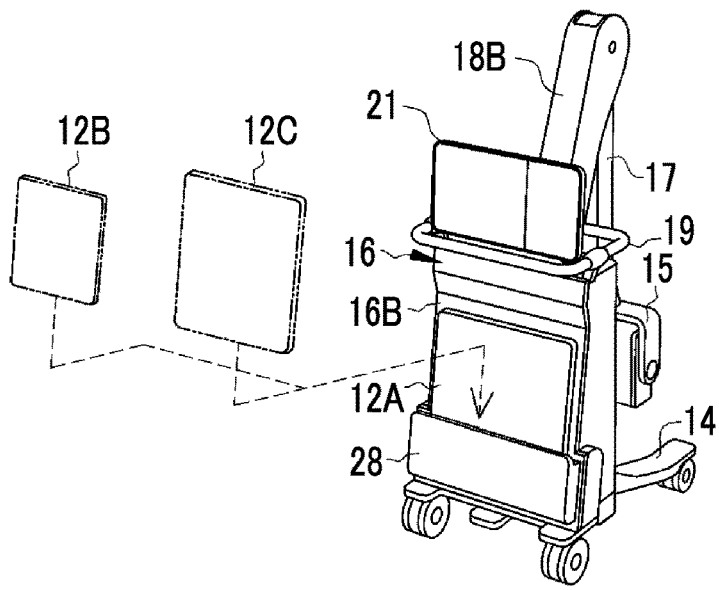
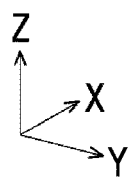
FIG. 9
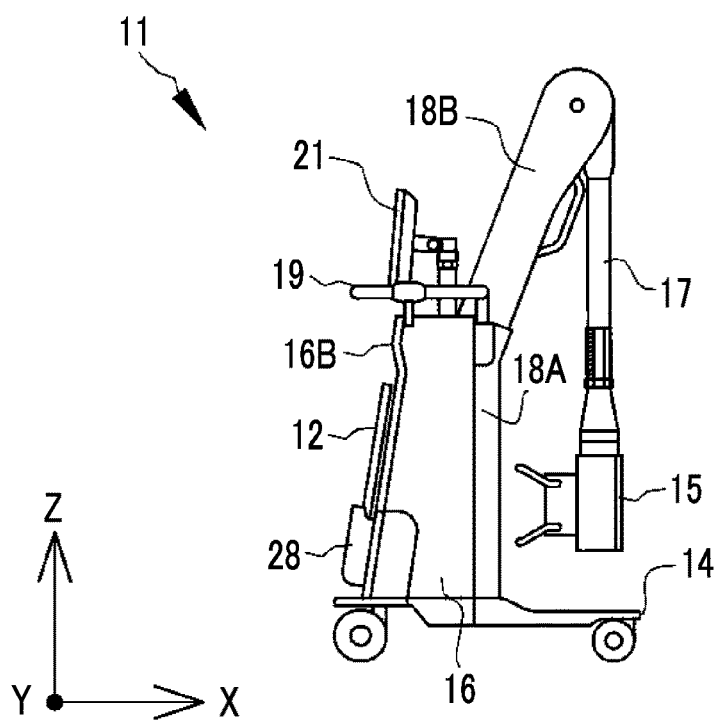
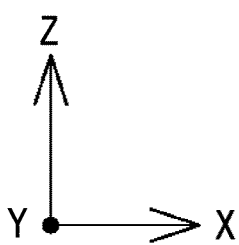

| PEDAL POSITION | LOCK MODE | LOCK OF ROTATION | LOCK OF SWIVEL |
|---|---|---|---|
| UPPER POSITION | SECOND LOCK MODE | RELEASED (OFF) | OPERATED (ON) |
| INITIAL POSITION | UNLOCKED STATE | RELEASED (OFF) | RELEASED (OFF) |
| LOWER POSITION | FIRST LOCK MODE | OPERATED (ON) | OPERATED (ON) |

COMPARATIVE EXAMPLE

COMPARATIVE EXAMPLE

MOBILE RADIATION GENERATION APPARATUS

CROSS-REFERENCE TO RELATED APPLICATIONS

This application is a Continuation of PCT International Application No. PCT/JP2017/011079 filed on Mar. 21, 2017, which claims priority under 35 U.S.C. § 119(a) to Japanese Patent Application No. 2016-077631 filed on Apr. 7, 2016. Each of the above application(s) is hereby expressly incorporated by reference, in its entirety, into the present application.

BACKGROUND OF THE INVENTION

1. Field of the Invention

The present invention relates to a mobile radiation generation apparatus used for radiography.

2. Description of the Related Art

In a medical field, a mobile radiation generation apparatus used for radiography has been known (for example, see JP1990-112578U (JP-H02-112578U)). The mobile radiation generation apparatus includes a radiation emitting unit, an arm unit, a support, and a carriage unit. The carriage unit is run to move the mobile radiation generation apparatus. Therefore, for example, the mobile radiation generation apparatus is used for visit imaging which visits a hospital room in which a patient is present in a hospital ward and performs radiography. Therefore, the mobile radiation generation apparatus is referred to as, for example, a treatment cart or a mobile radiography apparatus.

The arm unit has one end to which the radiation emitting unit is attached and a base end which is rotatably attached to the support. The support is fixed to the carriage unit. The radiation emitting unit and the arm unit are provided on the front side of the carriage unit.

In the mobile radiation generation apparatus disclosed in JP1990-112578U (JP-H02-112578U), the carriage unit includes a front wheel and a rear wheel and is run by the rotation of the front wheel and the rear wheel about the axles. The front wheel and the rear wheel are casters each of which independently swivels about a swivel axis that extends in a vertical direction perpendicular to the axle. The front wheel is one wheel and the rear wheels are two wheels. Two rear wheels are connected to each other through a link mechanism and swivel in the same phase in a case in which a steering wheel is operated. Since the front wheel and the rear wheel swivel independently, the direction of the carriage unit having the casters is easily changed and the carriage unit is easily moved in an oblique direction. Therefore, flexibility in movement is high.

The mobile radiation generation apparatus disclosed in JP1990-112578U (JP-H02-112578U) includes a rotation locking mechanism that locks the rotation of two rear wheels about the axle and a foot lever that is used to operate the rotation locking mechanism. At the time of imaging, the rotation of the rear wheels is locked to prevent the careless movement of the carriage unit. The foot lever is provided so as to surround the rear position and the left and right side positions of the carriage unit.

In a case in which imaging is performed, positioning which adjusts the irradiation position or irradiation direction of the radiation emitting unit according to an imaging part of the patient is performed with the mobile radiation generation apparatus brought close to a bed. Since the radiation emitting unit or the arm unit is disposed on the front side of the carriage unit, the radiation emitting unit is positioned from the front side of the carriage unit. In the mobile radiation generation apparatus disclosed in JP1990-112578U (JP-H02-112578U), the foot lever is provided so as to extend to the side position. Therefore, even in a case in which an operator stands in front of the carriage unit, the operator can operate the foot lever from the front side without moving to the rear side of the carriage unit.

SUMMARY OF THE INVENTION

In a case in which the wheels of the carriage unit are casters that are swivelable as in JP1990-112578U (JP-H02-112578U), the radiation emitting unit can be positioned by moving the carriage unit or by changing the direction of the carriage unit. In addition, in a case in which the arm unit is attached so as to be rotatable about a rotation axis parallel to the swivel axis of the caster, the arm unit is rotated about the rotation axis with respect to the carriage unit to finely adjust the position of the radiation emitting unit. As such, the configuration in which the wheels are casters has the advantage of improving flexibility in positioning.

However, in the configuration in which the wheels are casters that are swivelable, since the arm unit rotates about the rotation axis parallel to the swivel axis of the caster, the casters of the carriage unit are likely to move at the time of the rotation of the arm unit. In a case in which the casters move, the carriage unit becomes unstable, which makes it difficult to finely adjust the position of the radiation emitting unit.

In the carriage unit disclosed in JP1990-112578U (JP-H02-112578U), it is possible to lock the rotation of the rear wheel about the axle, but the swivel of the rear wheel about the swivel axis is not locked. Therefore, the carriage unit is likely to be unsteady due to rotating force about the rotation axis parallel to the swivel axis which acts on the carriage unit in a case in which the arm unit is rotated. In a case in which the carriage unit is unsteady, it is difficult to rotate the arm unit in a stable state. Therefore, it is difficult to finely adjust the position of the radiation emitting unit.

The foot lever which is a rotation locking operation member in JP1990-112578U (JP-H02-112578U) extends from the rear position to the side position of the carriage unit. In some cases, it is difficult for a medical staff member, who is an operator and stands in front of the carriage unit in order to operate the arm unit, to access the side position in order to operate the foot lever. The reason is as follows. In general, a free space on the bed side in the hospital room is very small and it is difficult to ensure the minimum space required for the movement of the medical staff. In a case in which imaging is performed in the small space, difficulty in accessing the rotation lock operation member leads to difficulty in finely adjusting the position of the radiation emitting unit.

An object of the invention is to provide a mobile radiation generation apparatus which reliably prevents the unsteady motion of a carriage unit with a simple structure and facilitates the fine adjustment of the position of a radiation emitting unit even in a case in which a wheel of the carriage unit is a caster that is swivelable.

In order to achieve the object, a mobile radiation generation apparatus according to the invention comprises: a carriage unit, an arm unit, a rotation locking mechanism, a swivel locking mechanism, and a front pedal. The carriage unit includes a front wheel and a rear wheel and is run by rotation of the front wheel and the rear wheel about axles. The front wheel and the rear wheel are casters that independently swivel about a swivel axis extending in a vertical direction perpendicular to the axle. The arm unit has a free end attached to a radiation emitting unit and rotates about a rotation axis parallel to the swivel axis with respect to the carriage unit, using a base end as a base point. The rotation locking mechanism locks the rotation of the rear wheel about the axle. The swivel locking mechanism locks the swivel of the rear wheel about the swivel axis. The front pedal is provided in the carriage unit so as to protrude forward from the carriage unit and is used to operate both the rotation locking mechanism and the swivel locking mechanism at the same time.

Preferably, the rear wheel includes two or more casters and each of the casters is capable of swiveling independently.

Preferably, the mobile radiation generation apparatus has a first lock mode in which the rotation locking mechanism and the swivel locking mechanism are operated for the rear wheel and a second lock mode in which the rotation locking mechanism is not operated and only the swivel locking mechanism is operated.

Preferably, the front pedal selectively switches the first lock mode and the second lock mode.

Preferably, the mobile radiation generation apparatus further comprises a rear pedal that is provided in the carriage unit so as to protrude backward from the carriage unit and has at least some of the functions of the front pedal.

Preferably, the rear pedal has the same functions as the front pedal. Preferably, the front pedal and the rear pedal are selectively switchable among three positions, that is, an initial position, an upper position that is above the initial position in the vertical direction, and a lower position that is below the initial position in the vertical direction. Preferably, the mobile radiation generation apparatus further comprises a front and rear pedal operative association mechanism that, in a case in which one of the front pedal and the rear pedal is moved to any one of the three positions, moves the other pedal to the same position in operative association with the one pedal.

According to the invention, it is possible to provide a mobile radiation generation apparatus which facilitates the fine adjustment of the position of a radiation emitting unit even in a case in which a front wheel and a rear wheel of the carriage unit are casters that are swivelable.

BRIEF DESCRIPTION OF THE DRAWINGS

FIG. 8 is a rear perspective view illustrating a cassette storage portion of the treatment cart.

FIG. 9 is a diagram illustrating the cassette storage portion located at a storage position.

DESCRIPTION OF THE PREFERRED EMBODIMENTS

First Embodiment

Figure 1:
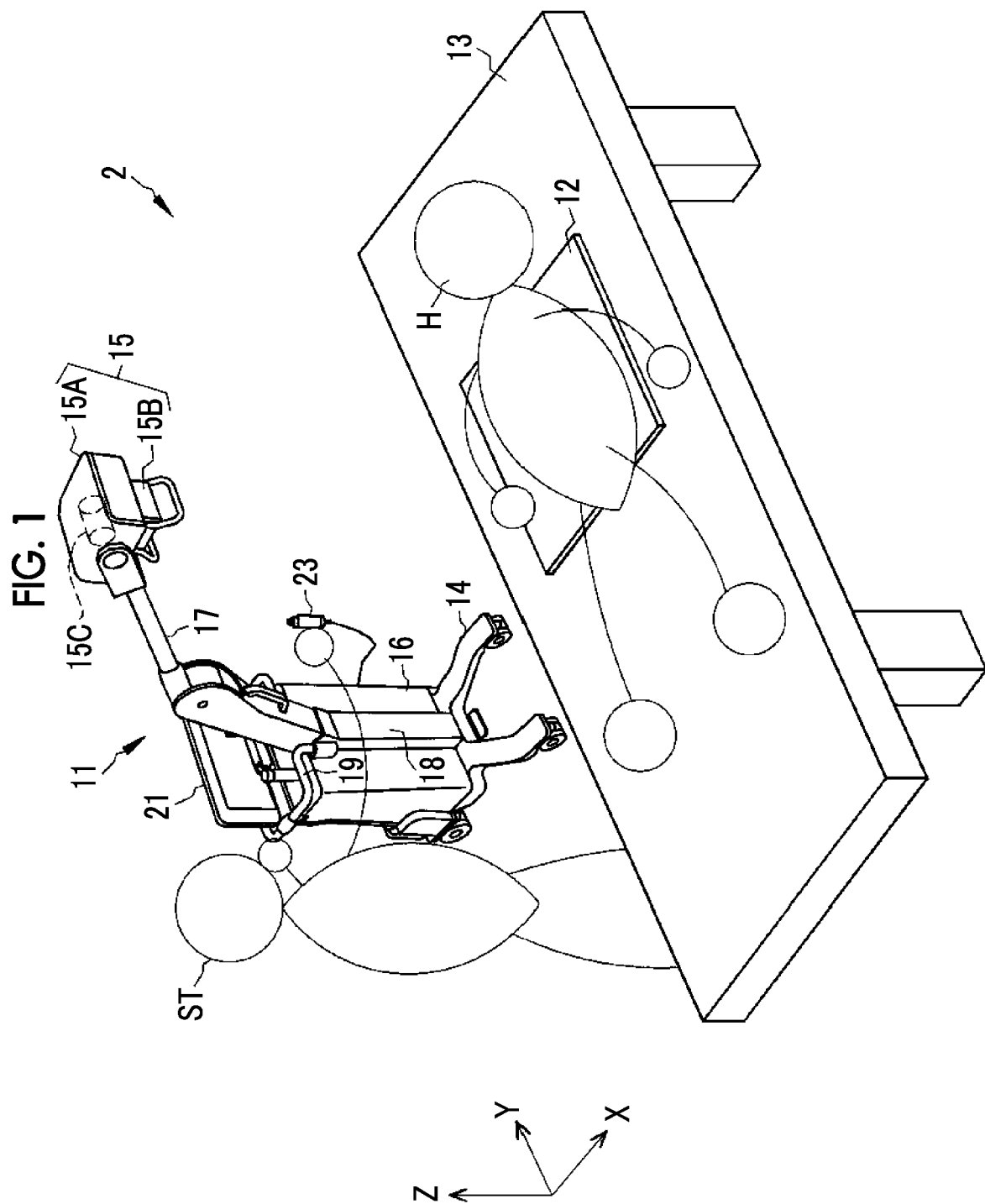
FIG. 1 is a diagram schematically illustrating an X-ray imaging system including a treatment cart (mobile radiation generation apparatus).

In FIG. 1, an X-ray imaging system 2 is a radiography system that uses X-rays as radiation and comprises a treatment cart 11 and an electronic cassette 12. Here, the treatment cart 11 corresponds to a mobile radiation generation apparatus described in the claims. The electronic cassette 12 is a portable X-ray image detector (corresponding to a radiographic image detector), detects X-rays transmitted through an object (patient) H, and outputs an X-ray image. The electronic cassette 12 is connected to an imaging control device (not illustrated) that controls the electronic cassette 12 or a console (not illustrated) that stores X-ray images or performs a process of displaying the X-ray images such that it can communicable with the imaging control device or the console wirelessly or in a wired manner. The electronic cassette 12 is placed on, for example, a bed 13 in order to capture an image of the object H. The electronic cassette 12 is positioned depending on an imaging part. For example, the electronic cassette 12 is held in the arms of the object H.

The treatment cart 11 generates X-rays for X-ray imaging. The treatment cart 11 includes a carriage unit 14 that can travel. Medical staff ST, such as a doctor or a radiology technician, can push the treatment cart 11 with hands to move the treatment cart 11. The treatment cart 11 is used for visit imaging in which the medical staff visits a hospital room in a hospital ward and takes a radiographic image. In addition, the treatment cart 11 can be moved to an operating room and then used during a surgical operation.

The treatment cart 11 comprises an X-ray emitting unit (corresponding to a radiation emitting unit) 15, a main body unit 16, an arm unit 17, a support 18, a handle 19, and an operation panel 21. These units are mounted on the carriage unit 14.

(X-Ray Emitting Unit)

The X-ray emitting unit 15 includes a radiation source unit 15A having an X-ray tube 15C that generates X-rays. An irradiation field limiter (also referred to as a collimator) 15B that limits the irradiation field of the X-rays generated from the X-ray tube 15C to the object H is attached to the radiation source unit 15A. The X-ray tube 15C includes, for example, a filament, a target, and a grid electrode (which are not illustrated). A voltage (tube voltage) is applied between the filament which is a cathode and the target which is an anode. The filament generates thermal electrons corresponding to the tube voltage. The generated thermal electrons are emitted to the target. The target collides with the thermal electrons emitted from the filament and emits X-rays. The grid electrode is provided between the filament and the target and changes the flow rate (tube current) of the thermal electrons from the filament to the target according to the applied voltage.

The irradiation field limiter 15B has, for example, a structure in which four shielding plates (for example, lead plates) that shield X-rays are provided on each side of a rectangle and a rectangular emission opening which transmits X-rays is provided at the center. The position of each shielding plate is changed to change the size of the emission opening, thereby limiting the irradiation field of X-rays.

The main body unit 16 is provided with, for example, a radiation source control device that controls the X-ray emitting unit 15 or a rechargeable battery that supplies power. The radiation source control device includes a voltage generation unit that generates the tube voltage and a voltage to be applied to the grid electrode and a control unit that controls the operation of the voltage generation unit to control the tube voltage, the tube current, and the emission time of X-rays. The radiation source control device and the X-ray emitting unit 15 are connected to each other by a cable for supplying a voltage and transmitting a control signal.

(Main Body Unit)

Figure 2:
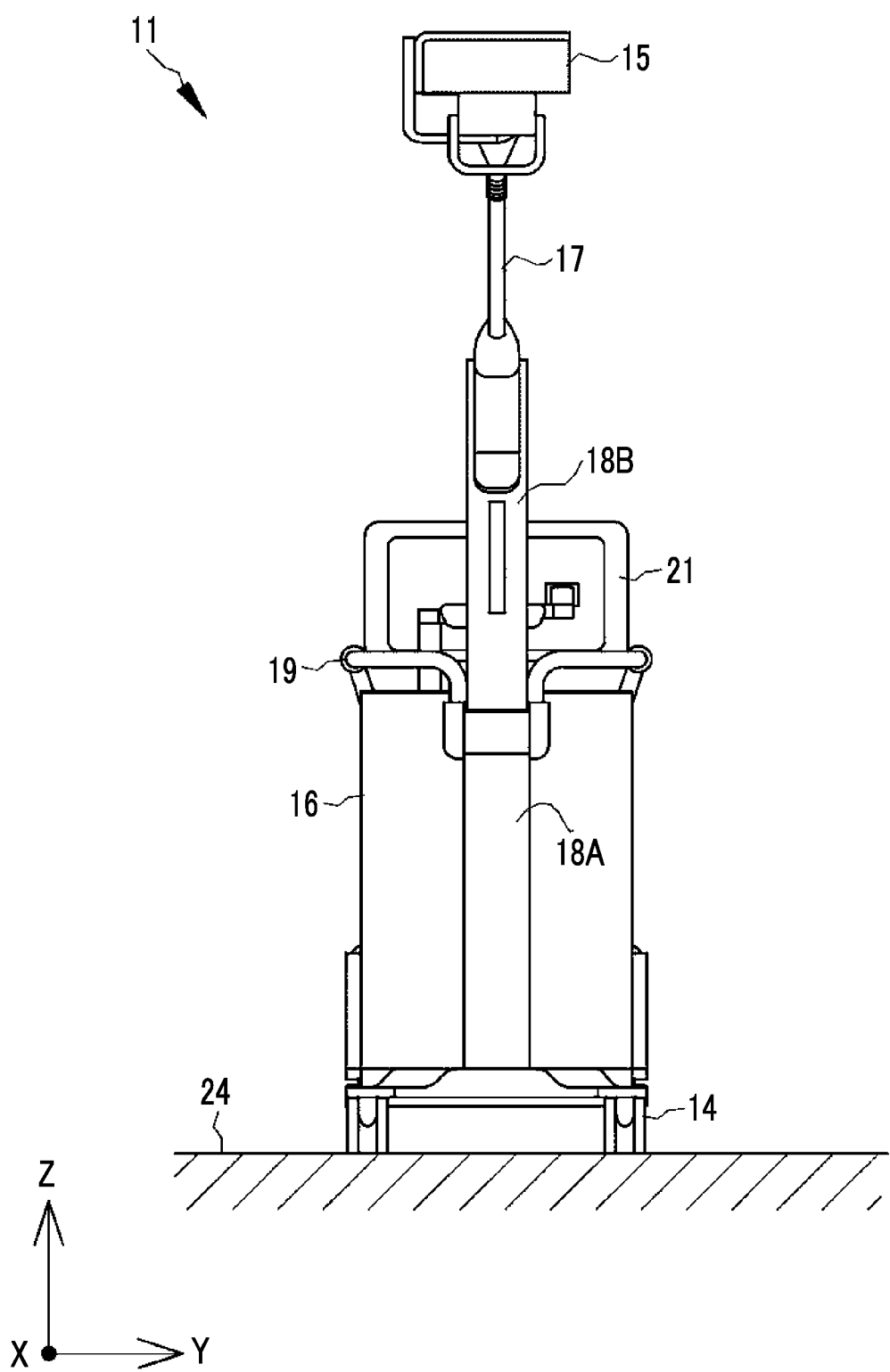
FIG. 2 is a front view illustrating the treatment cart.
Figure 3:
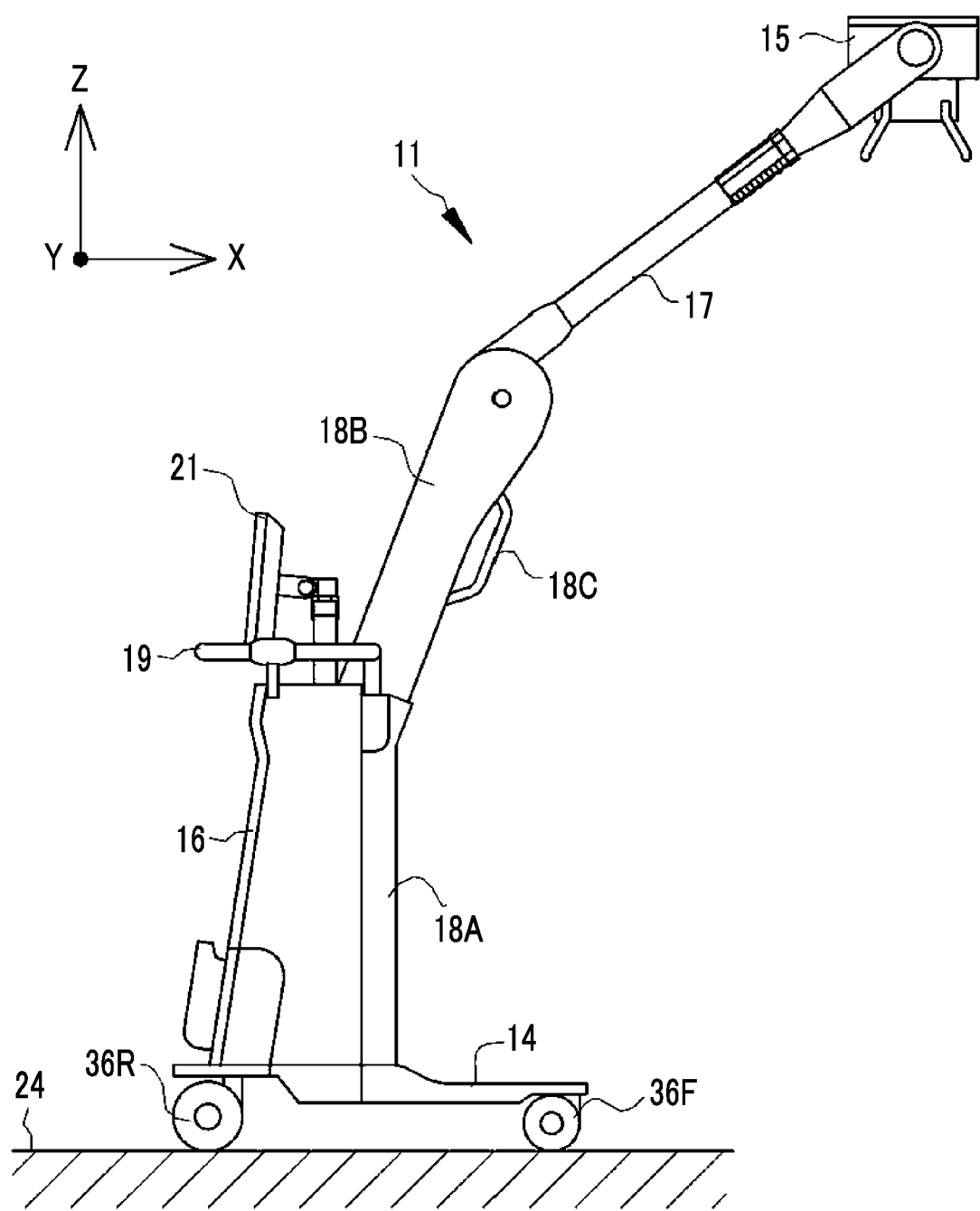
FIG. 3 is a side view illustrating the treatment cart.

The main body unit 16 is small and light. In particular, as illustrated in FIGS. 2 and 3, the main body unit 16 is a thin type in which a length in a front-rear direction (X-axis direction) is less than a length in a width direction (Y-axis direction). Since the main body unit 16 is a thin type, it can get into a small space of the hospital room. The length of the main body unit 16 in the front-rear direction (X-axis direction) is, for example, about two-thirds of the length of the carriage unit 14 in the front-rear direction. In the carriage unit 14, the mounting position of the main body unit 16 is offset to the rear and a front portion of the carriage unit 14 protrudes forward from the main body unit 16. However, since the height of the carriage unit 14 is less than the height of a leg portion of the bed 13, the carriage unit 14 can get into a space below the bed 13. Therefore, in a case in which the front portion of the carriage unit 14 gets into a clearance space below the top plate of the bed 13, a front surface of the main body unit 16 and the bed 13 can be brought close to each other.

The main body unit 16 is provided with the operation panel 21. The operation panel 21 includes an operation unit for operating the X-ray emitting unit 15 and an image display unit on which the X-ray image detected by the electronic cassette 12 is displayed. The medical staff ST inputs X-ray emission conditions (for example, a tube voltage, a tube current, and an irradiation time) through the operation unit. In addition, an irradiation switch 23 for commanding the X-ray emitting unit 15 to start the emission of X-rays is connected to the radiation source control device in the main body unit 16.

For example, the irradiation switch 23 is pressed in two stages. In a case in which the irradiation switch 23 is pressed to the first stage (pressed halfway), the irradiation switch 23 generates a warm-up command signal. In a case in which the irradiation switch 23 is pressed to the second stage (pressed fully), the irradiation switch 23 generates an irradiation start command signal.

In a case in which the warm-up command signal is input, the radiation source control device preheats the filament. At the same time, the radiation source control device starts the rotation of the target. In a case in which the preheating of the filament is completed and the rotation speed of the target reaches a predetermined value, warming-up ends. In a case in which the irradiation start command signal is input, the radiation source control device generates a voltage such that the X-ray emitting unit 15 starts the emission of X-rays. In a case in which the irradiation time set in the irradiation conditions passes, the radiation source control device stops the emission of X-rays.

(Support and Arm Unit)

Figure 4:
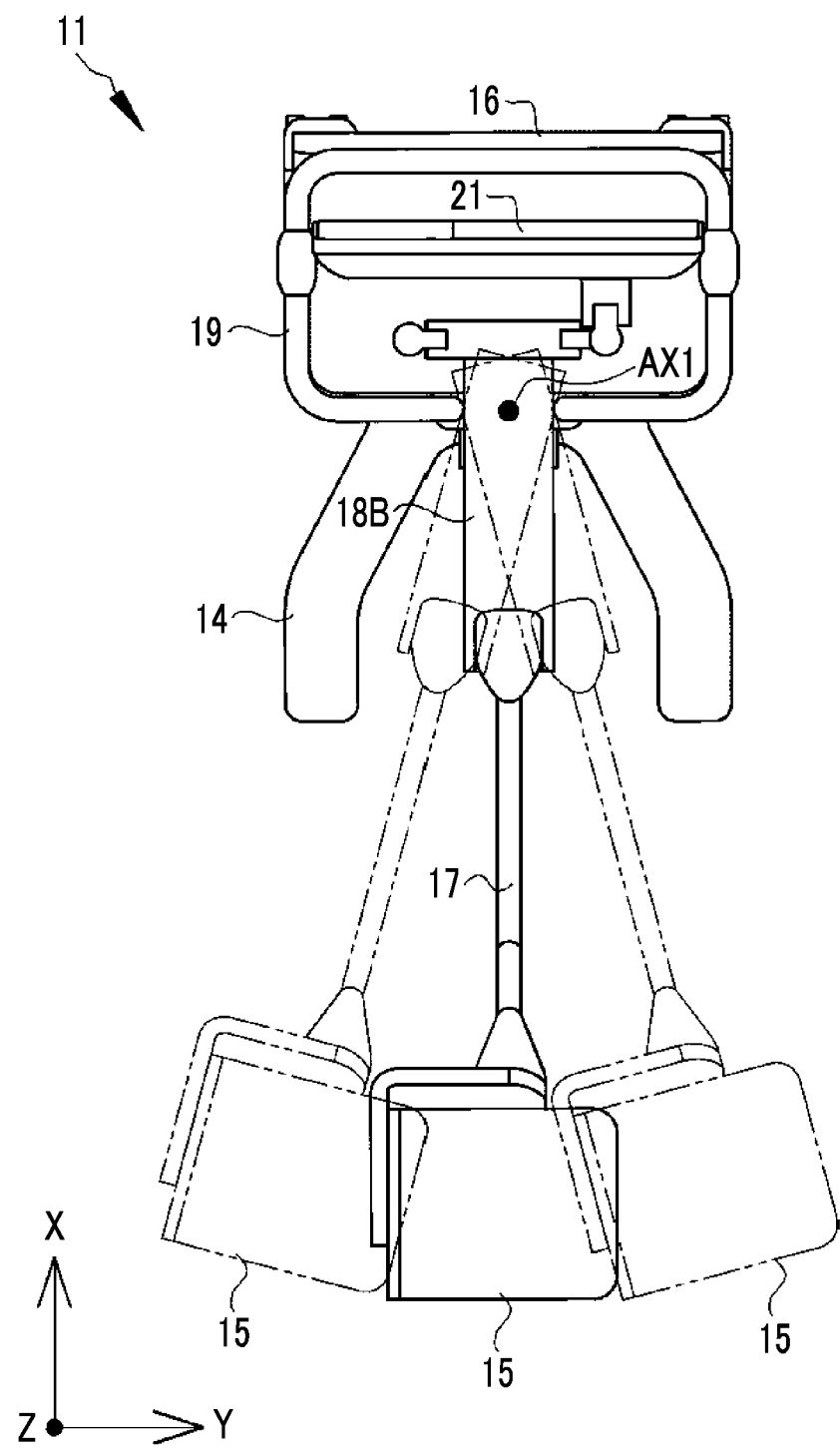
FIG. 4 is a diagram illustrating the rotation of an arm unit.

As illustrated in FIGS. 2 to 4, the arm unit 17 has one end which is a free end and to which the X-ray emitting unit 15 is attached and a base end which is opposite to the free end and to which the support 18 is attached. The support 18 vertically stands on the carriage unit 14. As illustrated in FIG. 2, the support 18 is provided at the center of the carriage unit 14 in the width direction (Y-axis direction). As illustrated in FIG. 3, the support 18 is provided between a front wheel 36F and a rear wheel 36R in the front-rear direction (X-axis direction) of the carriage unit 14.

The support 18 includes a first support portion 18A that is located on the lower side in the vertical direction and a second support portion 18B that is located on the upper side. The first support portion 18A vertically extends upward from an upper surface of the carriage unit 14. The longitudinal direction of the first support portion 18A is parallel to the Z-axis direction. The Z-axis is aligned with the vertical direction in a case in which a placement surface 24 on which the carriage unit 14 is placed is horizontal. The first support portion 18A is partially fitted to a concave portion formed in the front surface of the main body unit 16 and forms a portion of the main body unit 16 in appearance. The first support portion 18A has a lower end that is fixed to the carriage unit 14 and an upper end to which the second support portion 18B is attached.

As illustrated in FIG. 3, the second support portion 18B is inclined toward the front side of the treatment cart 11 with respect to the vertical direction (Z-axis direction). The arm unit 17 is attached to the second support portion 18B. A base end of the arm unit 17 is supported by an upper end of the second support portion 18B.

As illustrated in FIG. 4, a base end of the second support portion 18B is rotatable about a rotation axis AX1 that extends in the Z-axis direction at the upper end of the first support portion 18A. For example, the rotation range of the second support portion 18B from an initial position (represented by a solid line) where the longitudinal direction of the second support portion 18B is parallel to the front-rear direction (X-axis direction) of the treatment cart 11 to each of the left and right positions (represented by a two-dot chain line) is about 15°. That is, the total rotation range of the second support portion 18B is 30°. The rotation angle of the second support portion 18B can be adjusted to any angle in the rotation range. A grip portion 18C that is gripped to rotate the second support portion 18B is provided on the front surface of the second support portion 18B.

Since the first support portion 18A is fixed to the carriage unit 14, the second support portion 18B rotates about the rotation axis AX1 that extends in the Z-axis direction with respect to the carriage unit 14. The base end of the arm unit 17 is attached to the second support portion 18B. Therefore, the arm unit 17 rotates about the rotation axis AX1 with respect to the carriage unit 14, using the base end of the arm unit 17 as a base point.

Figure 5:
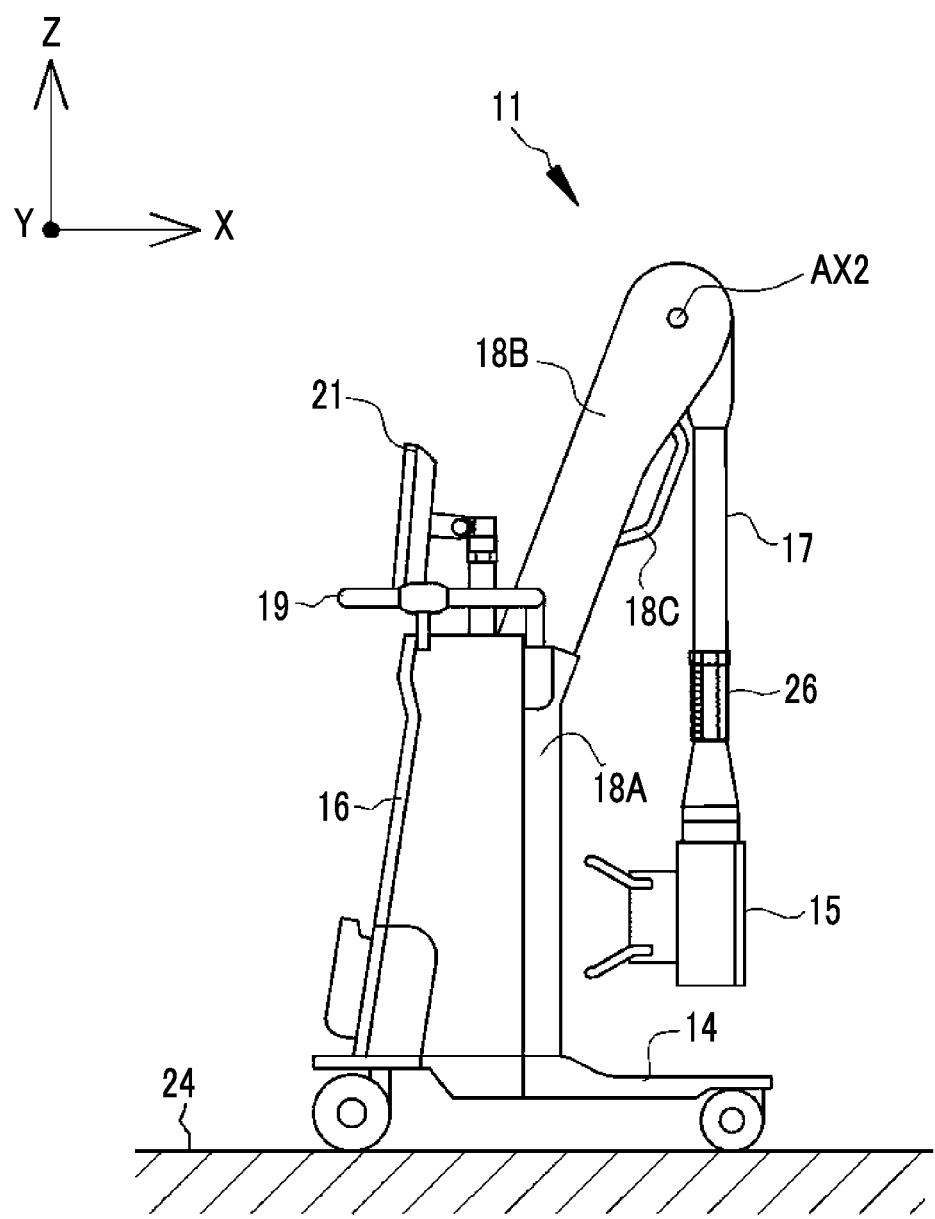
FIG. 5 is a side view illustrating the treatment cart in a state in which the arm unit is folded.
Figure 6:
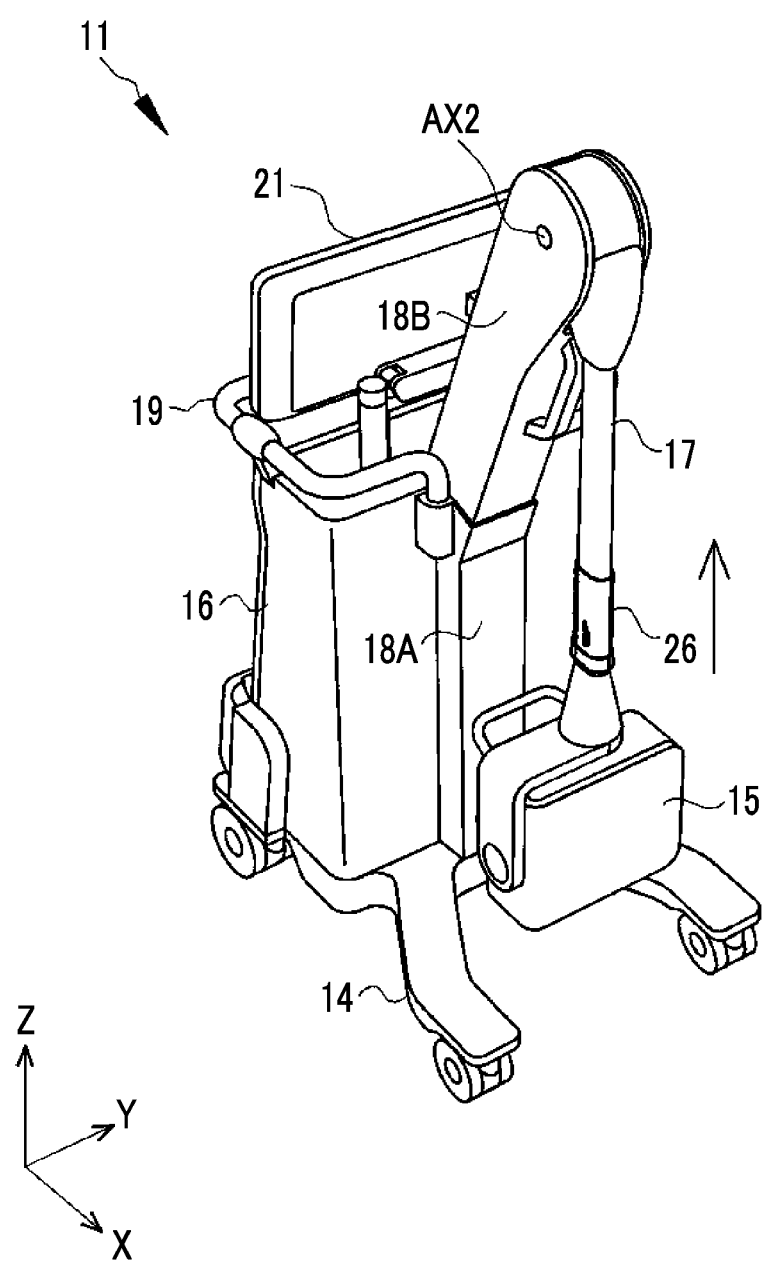
FIG. 6 is a perspective view illustrating the treatment cart in a state in which the arm unit is folded.

As illustrated in FIGS. 5 and 6, the base end of the arm unit 17 is rotatable about a rotation axis AX2 that extends in the Y-axis direction and the arm unit 17 is folded to a storage position where the front surface of the main body unit 16 faces the X-ray emitting unit 15. The rotation range of the arm unit 17 is a range between the storage position illustrated in FIGS. 5 and 6 and the upper end position illustrated in FIG. 3. The rotation angle of the arm unit 17 can be adjusted to any angle in the rotation range.

(Unlocking Operation Portion of Arm Locking Mechanism)

An arm locking mechanism (not illustrated) that locks the movement of the arm unit 17 at the storage position of the arm unit 17 is provided in a connection portion between the arm unit 17 and the second support portion 18B. At the storage position, the free end of the arm unit 17 to which the X-ray emitting unit 15 is attached is located on the lower side and the base end of arm unit 17 supported by the support 18 is located on the upper side in the vertical direction. Since the arm unit 17 is locked at the storage position, the arm unit 17 is prevented from being carelessly rotated while the treatment cart is not used for imaging. In the arm unit 17, an unlocking operation portion 26 that unlocks the arm locking mechanism is provided in a root portion attached to the X-ray emitting unit 15.

The unlocking operation portion 26 is a cylindrical member that covers the outer circumference of the arm unit 17 and is slidably attached along the longitudinal axis of the arm unit 17. In a case in which the arm unit 17 is at the storage position and the unlocking operation portion 26 is slid to the base end of the arm unit 17 in a direction represented by an arrow in FIG. 6, the arm unit 17 is unlocked. Therefore, the arm unit 17 can be rotated from the storage position to the upper end position.

The sliding direction of the unlocking operation portion 26 at the time of unlocking is a vertically upward direction in a case in which the arm unit 17 is at the storage position. At the time of imaging, in a case in which the unlocking operation portion 26 is slid to unlock the arm unit 17 at the storage position, the arm unit 17 is lifted upward to the upper end position so as to be developed. At that time, the direction in which the arm unit 17 is lifted is aligned with the sliding direction of the unlocking operation portion 26. Therefore, it is possible to develop the arm unit 17 while holding the unlocking operation portion 26, without changing the holding position. As a result, operability is high.

The arm unit 17 can be stopped at any position between the upper end position and the storage position in the rotation about the rotation axis AX2. The stop of the arm unit 17 at any position is implemented by the action of frictional force in the connection portion between the base end of the arm unit 17 and the second support portion 18B. In a case in which the arm unit 17 is further moved to the storage position in the developed state, the arm locking mechanism automatically operates to lock the movement of the arm unit 17.

(Handle)

Figure 7:
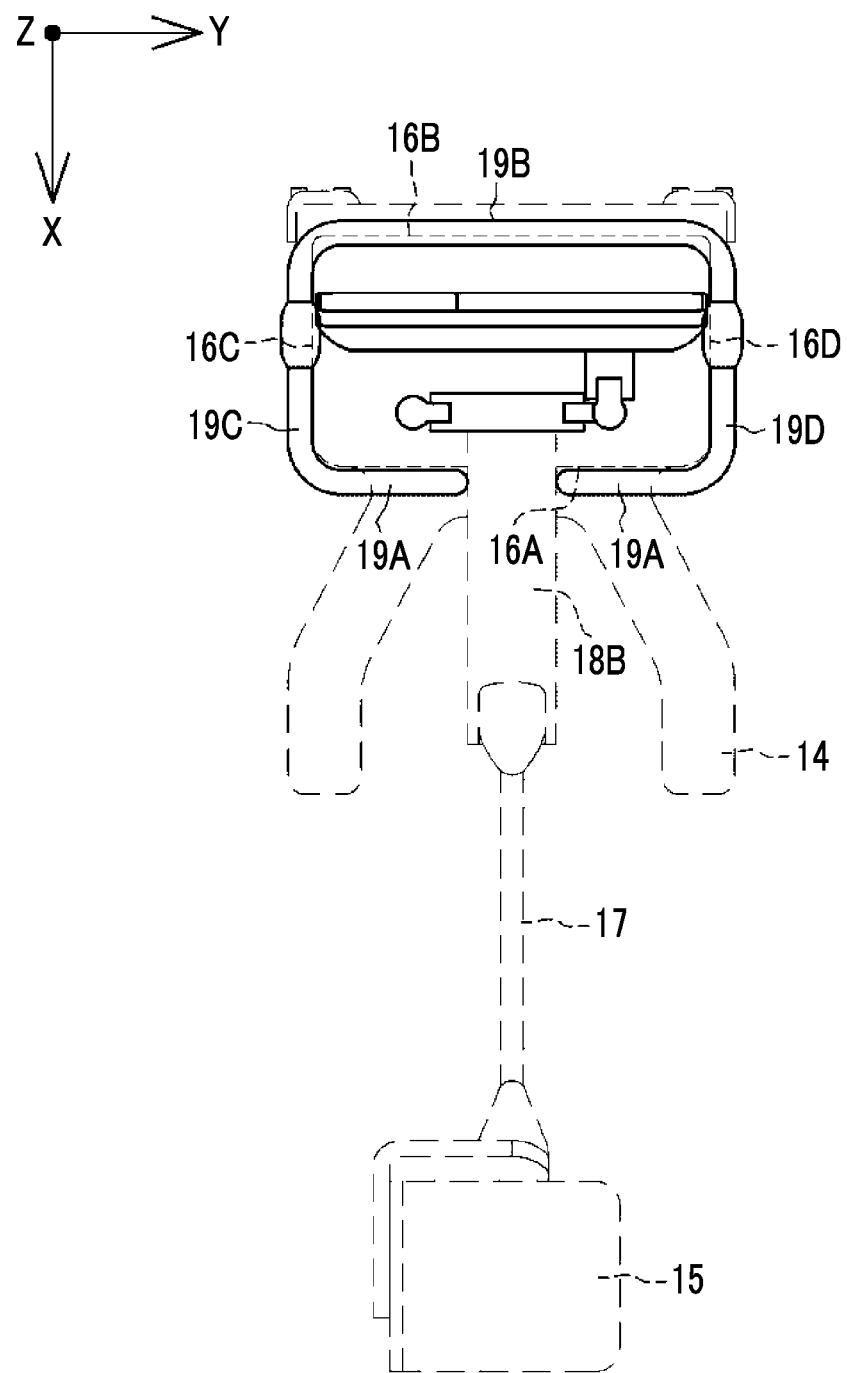
FIG. 7 is a diagram illustrating a handle.

As illustrated in FIG. 7, the handle 19 is provided on the upper side of the main body unit 16. The handle 19 is held in a case in which the carriage unit 14 is moved. The handle 19 is, for example, a bar handle which is a cylindrical bar having a substantially circular shape in a cross-sectional view. Of course, the cross-sectional shape of the bar handle may be a polygon and a shape that is easy to grip is appropriately selected.

The handle 19 includes a front bar portion 19A, a rear bar portion 19B, a left side bar portion 19C, and a right side bar portion 19D whose positions correspond to a front surface 16A, a rear surface 16B, a left side surface 16C, and a right side surface 16D of the main body unit 16, respectively.

The front bar portion 19A and the rear bar portion 19B extend in the width direction (Y-axis direction) perpendicular to the front-rear direction (X-axis direction) of the main body unit 16. The side bar portion 19C and the side bar portion 19D extend in the front-rear direction (X-axis direction) of the main body unit 16. The rear bar portion 19B of the handle 19 is disposed behind the support 18 and the side bar portions 19C and 19D are disposed on the side of the support 18. Here, the rear side of the support 18 is a position corresponding to the rear of the carriage unit 14 and the side of the support 18 is a position corresponding to the side of the carriage unit 14. The position of the front bar portion 19A in the front-rear direction is substantially the same as that of the support 18 and the front bar portion 19A extends in the width direction on both sides of the support 18.

As such, since the handle 19 is provided over substantially the entire periphery of the main body unit 16, it is possible to access the handle 19 in all directions of the treatment cart 11. Since the treatment cart 11 can be operated from the front or the side, the handle 19 is very convenient, which will be described below.

(Cassette Storage Portion)

As illustrated in FIG. 8, a cassette storage portion (corresponding to a storage portion) 28 that stores the electronic cassette 12 is provided on the rear surface 16B of the main body unit 16. The electronic cassette 12 has a flat shape and has a detection surface whose planar shape is a rectangle. The cassette storage portion 28 stores the electronic cassette 12 in a posture in which the detection surface is parallel to the rear surface 16B. The cassette storage portion 28 is a thin box type with a size adjusted to the vertical and horizontal sizes and thickness of the electronic cassette 12.

The electronic cassette 12 has a plurality of sizes according to the size of the detection surface. The cassette storage portion 28 has a maximum size that can store an electronic cassette 12A with a vertical and horizontal size of 17 inches×17 inches. In addition, the cassette storage portion 28 can store electronic cassettes with other sizes, such as an electronic cassette 12B with a size of 12 inches×10 inches that is smaller than the size of the electronic cassette 12A and an electronic cassette 12C with a size of 17 inches×14 inches.

Figure 10:
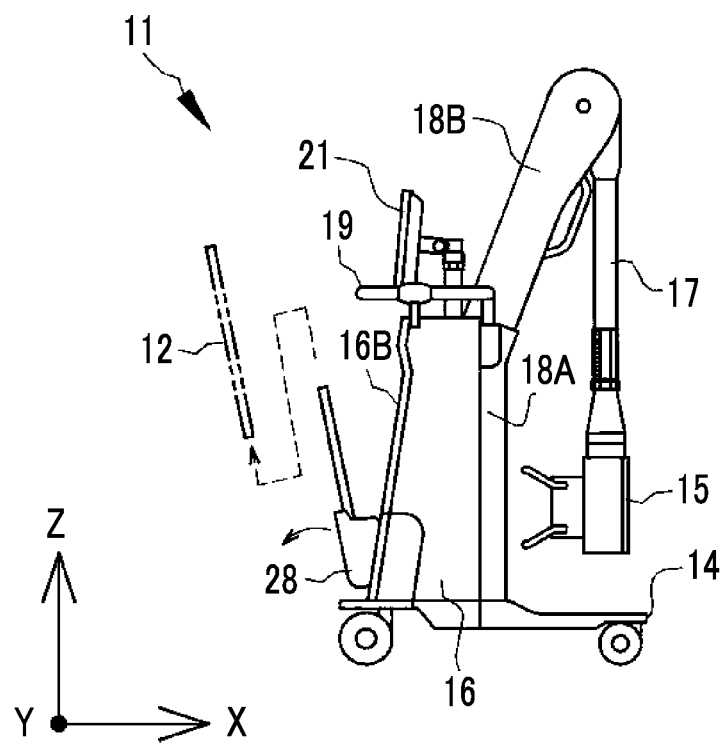
FIG. 10 is a diagram illustrating the cassette storage portion located at an extraction position.

The cassette storage portion 28 is movable between a storage position illustrated in FIG. 9 and an extraction position illustrated in FIG. 10. The rear surface 16B is inclined forward and the cassette storage portion 28 is also inclined forward at an angle corresponding to the inclination angle of the rear surface 16B at the storage position illustrated in FIG. 9. Therefore, at the storage position, the electronic cassette 12 is also inclined at an angle corresponding to the inclination of the rear surface 16B. The storage position can be inclined forward such that the electronic cassette 12 leans against the rear surface 16B. Therefore, the electronic cassette 12 can be stored in a stable state with less unsteadiness as compared to a case in which the electronic cassette 12 is stored in a vertical posture.

Figure 11:
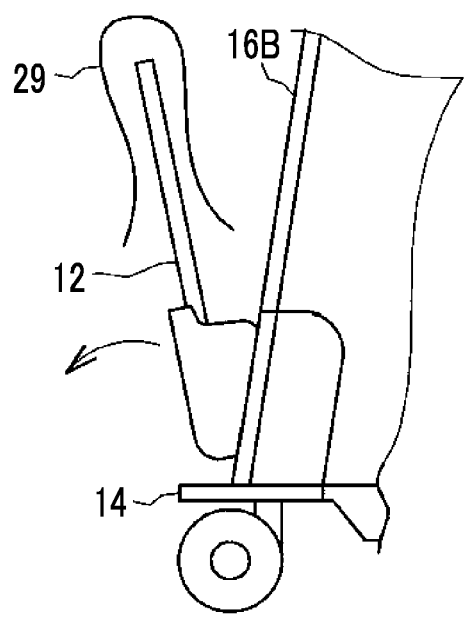
FIG. 11 is a diagram illustrating how to cover an antibacterial bag.

In a case in which the cassette storage portion 28 is rotated backward about a lower end portion as a base point from the storage position illustrated in FIG. 9, the cassette storage portion 28 is moved to the extraction position illustrated in FIG. 10. At the extraction position, the cassette storage portion 28 is inclined backward and the electronic cassette 12 is also inclined backward. Therefore, an upper part of the electronic cassette 12 is separated from the rear surface 16B with a gap interposed therebetween, which makes it easy to hold the upper part of the electronic cassette 12 and to take out the electronic cassette 12. In addition, the gap makes it possible to cover the electronic cassette 12 with an antibacterial bag 29 or to replace the bag 29 at the extraction position as illustrated in FIG. 11, without taking out the electronic cassette 12 from the cassette storage portion 28.

Figure 12:
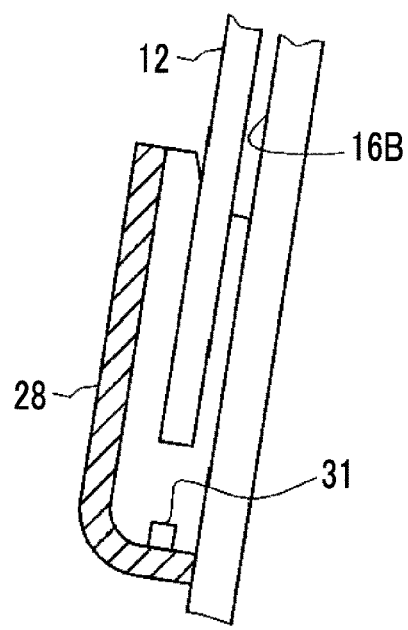
FIG. 12 is a diagram illustrating a charging connector in the cassette storage portion.
Figure 13:
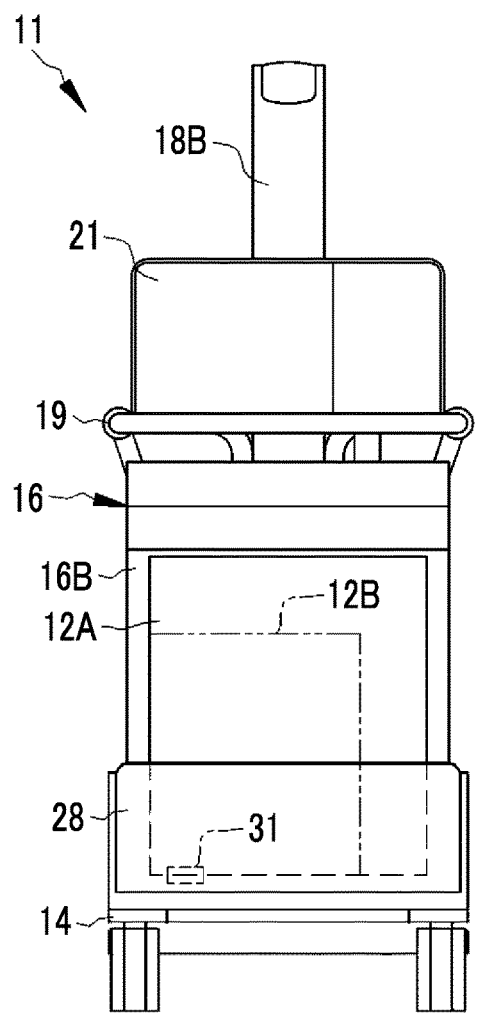
FIG. 13 is a rear view illustrating the treatment cart.

As illustrated in FIGS. 12 and 13, a charging connector 31 is provided on the bottom in the cassette storage portion 28. The charging connector 31 is a connector for charging a battery of the electronic cassette 12. Since the charging connector 31 is provided in the cassette storage portion 28, it is possible to charge the battery while the electronic cassette 12 is being stored in the cassette storage portion 28.

As illustrated in FIG. 13, the position of the charging connector 31 is offset from a center position to the left in the width direction (Y-axis direction) of the treatment cart 11 as viewed from the rear side. This corresponds to the structure of the electronic cassettes 12A to 12C in which the position of a charging terminal connected to the charging connector 31 is offset to the left as viewed from the rear side.

Even in a case in which the electronic cassettes 12A and 12B have different sizes, the electronic cassettes 12A and 12B have the same distance from the left end to the charging terminal in FIG. 13. In addition, in the cassette storage portion 28, the distance from the inner wall of the left end in FIG. 13 to the charging connector 31 is equal to the distance to the charging terminals of the electronic cassettes 12A and 12B. Therefore, the left end of the electronic cassette 12 is brought into contact with the inner wall of the left end of the cassette storage portion 28 to align the position of the charging connector 31 with the position of the charging terminal, regardless of the size of the electronic cassette 12.

(Rotation Locking Mechanism, Swivel Locking Mechanism, and Front and Rear Pedals)

Figure 14:
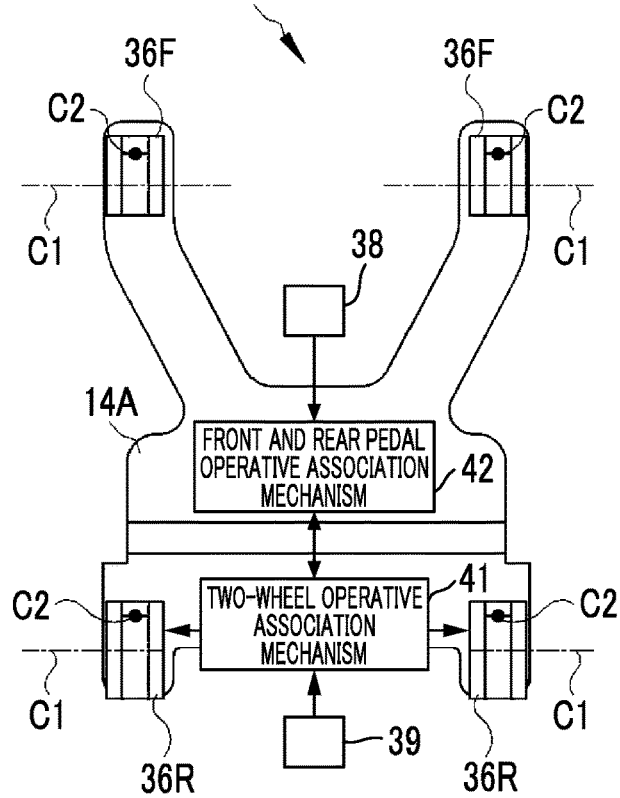
FIG. 14 is a functional diagram illustrating a front pedal and a rear pedal.

As illustrated in FIG. 14, the carriage unit 14 includes the front wheel 36F and the rear wheel 36R. Each of the front wheel 36F and the rear wheel 36R rotates about an axle C1 to run the carriage unit 14. Each of the front wheel 36F and the rear wheel 36R is a caster that independently swivels about an axis that extends in the vertical direction (Z-axis direction) perpendicular to the axle C1. Here, the axis about which the caster swivels is referred to as a swivel axis C2. Each of the front wheel 36F and the rear wheel 36R includes two casters. The carriage unit 14 includes a total of four casters of the front wheel 36F and the rear wheel 36R. Two casters forming the rear wheel 36R can swivel independently. Two casters forming the front wheel 36F can swivel independently. Each of the front wheel 36F and the rear wheel 36R may include three or more casters.

The front wheel 36F and the rear wheel 36R are attached to a lower surface of a frame 14A of the carriage unit 14. The front wheel side of the frame 14A is branched into left and right portions and has a Y-shape. The front wheel 36F is provided at the leading end of each of the left and right branched portions of the frame 14A. As such, since the front wheel side of the frame 14A is formed in a Y-shape, it is easy to put the carriage unit 14 in a clearance space below the top plate of the bed 13. For example, in a case in which the carriage unit 14 is put in the space below the bed 13, a clearance space corresponding to the width of the frame is required in consideration of the frame with a flat plate shape. In the case of the frame 14A with a Y-shape, since the width of the left and right branched portions is small, a necessary clearance space is narrower than that in a case in which the frame has a flat plate shape.

The carriage unit 14 is provided with a rotation locking mechanism that locks the rotation of the rear wheel 36R about the axle C1 and a swivel locking mechanism that locks the swivel of the rear wheel 36R about the swivel axis C2. No rotation locking mechanisms and no swivel locking mechanisms are provided for the front wheel 36F and the front wheel 36F is always in a free state in which it is not locked.

Figure 15:
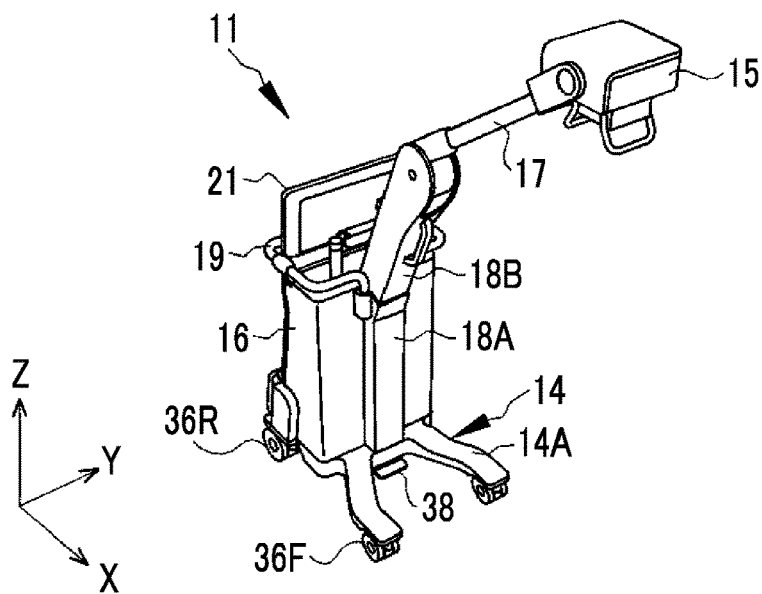
FIG. 15 is a perspective view illustrating the front pedal.
Figure 16:
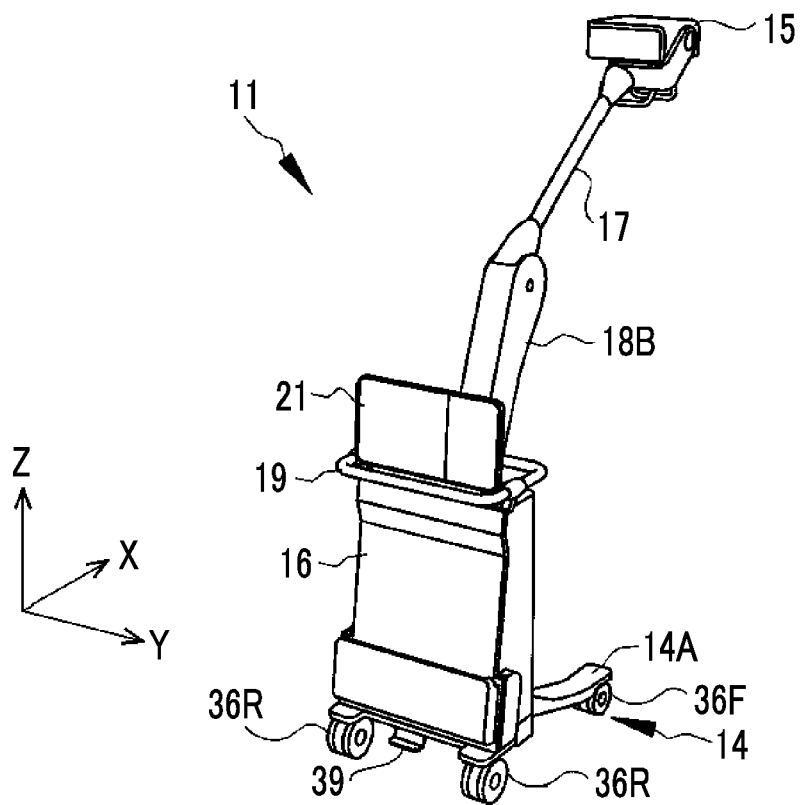
FIG. 16 is a perspective view illustrating the rear pedal.

As illustrated in FIGS. 15 and 16 in addition to FIG. 14, the carriage unit 14 includes a front pedal 38 that is provided closer to the front wheel 36F than the support 18 and a rear pedal 39 that is provided closer to the rear wheel 36R than the support 18. The first support portion 18A which is a base end portion of the support 18 stands vertically between the front wheel 36F and the rear wheel 36R in the front-rear direction of the carriage unit 14. Specifically, the front pedal 38 is provided closer to the front wheel 36F than the first support portion 18A and the rear pedal 39 is provided closer to the rear wheel 36R than the first support portion 18A. The front pedal 38 is provided so as to protrude forward from the carriage unit 14 and the rear pedal 39 is provided so as to protrude backward from the carriage unit 14. The provision of the front pedal 38 in addition to the rear pedal 39 makes it possible to perform a locking operation from the front side and/or the oblique front side.

The rear pedal 39 is provided with a two-wheel operative association mechanism 41. Therefore, it is possible to perform a locking operation and an unlocking operation for two rear wheels 36R at the same time. The front pedal 38 and the rear pedal 39 are operatively associated with each other by the operation of a front and rear pedal operative association mechanism 42. Therefore, the front pedal 38 and the rear pedal 39 can perform the same operation.

Figure 17:
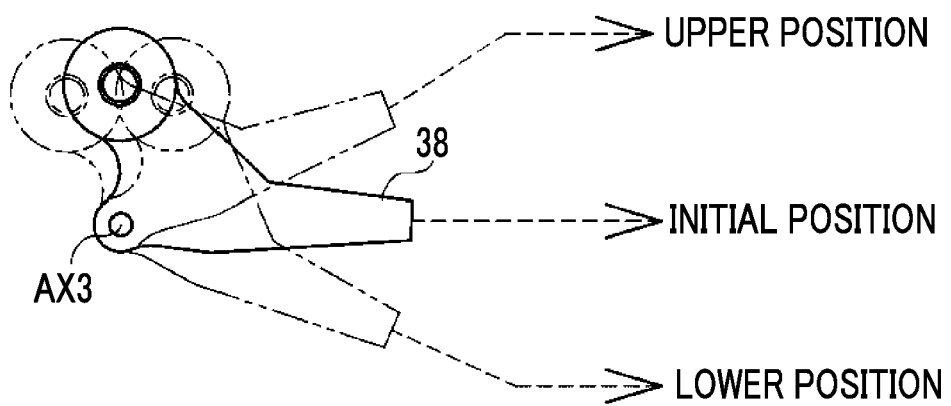
FIG. 17 is a diagram illustrating three pedal positions of the front pedal.

As illustrated in FIG. 17, the front pedal 38 can be selectively operated to three positions, that is, an initial position, an upper position that is above the initial position in the vertical direction, and a lower position that is below the initial position in the vertical direction. Any one of the three pedal positions is selected to selectively switch among a total of three modes including two lock modes of the rear wheel 36R, that is, a first lock mode and a second lock mode, and an unlocked state in which locking is released. The rear pedal 39 has the same functions as the front pedal 38. In addition, the front pedal 38 and the rear pedal 39 are operatively associated with each other. Therefore, in a case in which the front pedal 38 is moved to the upper position, the rear pedal 39 is also moved to the upper position. In a case in which the front pedal 38 is moved to the lower position, the rear pedal 39 is also moved to the lower position.

Figures 18, 19:
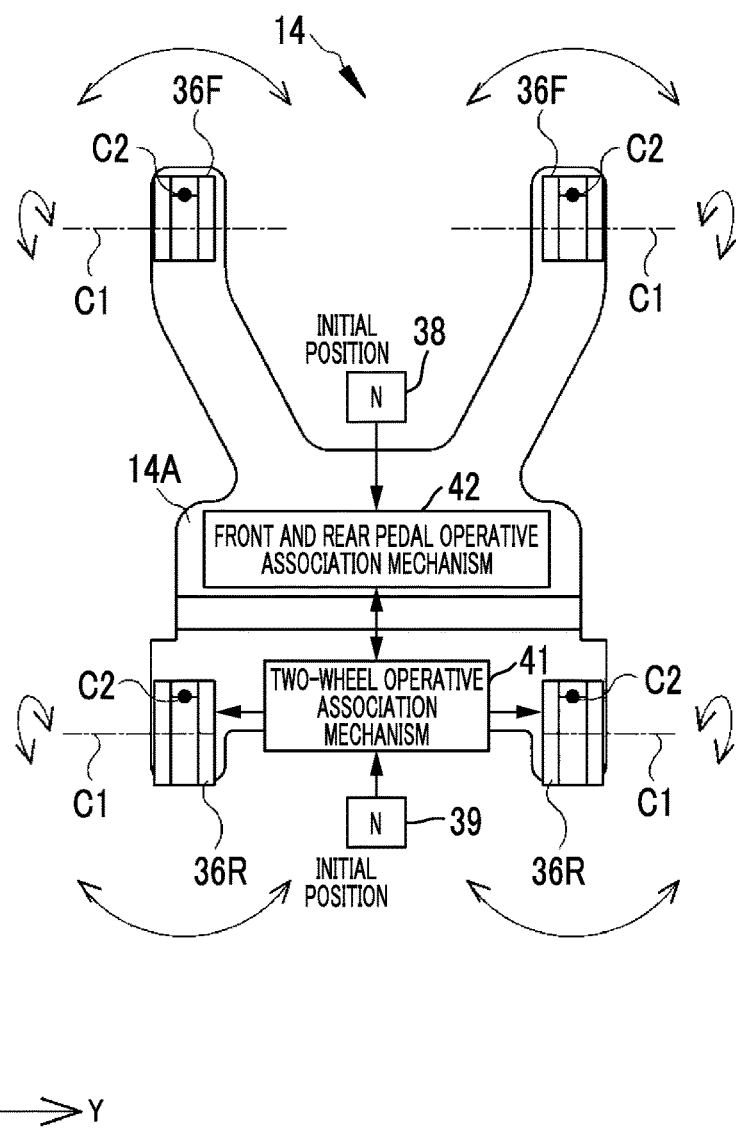
FIG. 18 is a table illustrating the relationship between a pedal position and a lock mode.
FIG. 19 is a diagram illustrating an unlocked state.

As illustrated in FIGS. 18 and 19, in a case in which the pedal position is the initial position, the lock mode is neutral, that is, both the rotation lock and the swivel lock are released (turned off). As illustrated in FIG. 19, the rear wheel 36R is in a state in which it can rotate about the axle C1 and can swivel about the swivel axis C2. Therefore, the carriage unit 14 can be slid in an oblique direction and/or the horizontal direction as well as the front-rear direction. In addition, the direction of the carriage unit 14 can be changed at a predetermined position.

Figure 20:
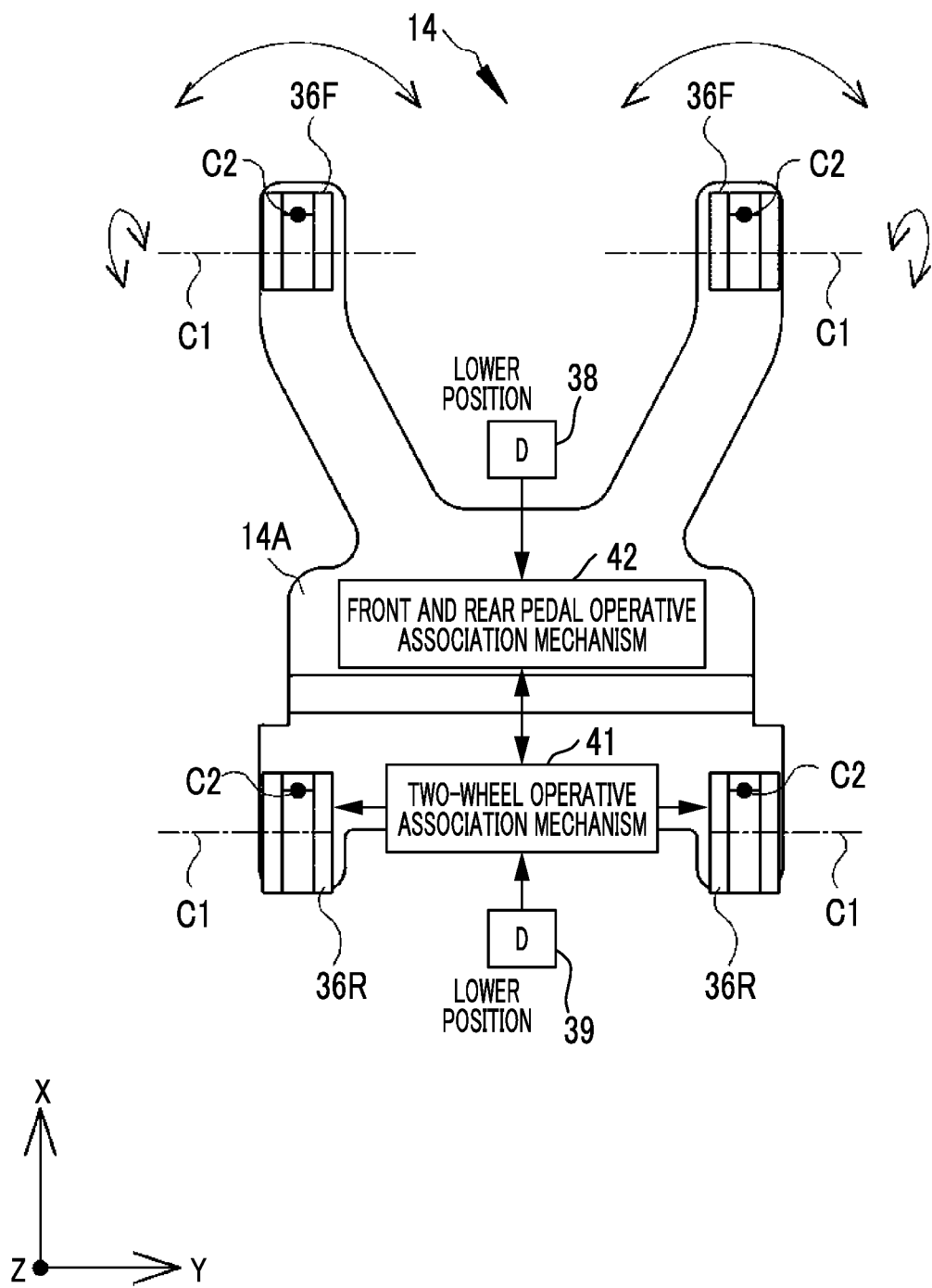
FIG. 20 is a functional diagram illustrating a first lock mode.

As illustrated in FIGS. 18 and 20, the lock mode is the first lock mode in a case in which the pedal position is the lower position. In the first lock mode, both the rotation locking mechanism and the swivel locking mechanism of the rear wheel 36R are operated (turned on) at the same time.

Hereinafter, for convenience, operating (turning on) the rotation locking mechanism is simply referred to locking rotation or operating (turning on) the rotation lock and unlocking the rotation locking mechanism is simply referred to as releasing the rotation lock. Similarly, operating (turning on) the swivel locking mechanism is simply referred to locking swivel or operating (turning on) the swivel lock and unlocking the swivel locking mechanism is simply referred to as releasing swivel lock.

As illustrated in FIG. 20, in the first lock mode in which the front pedal 38 and the rear pedal 39 are at the lower position (D), both the rotation of the rear wheel 36R about the axle C1 and the swivel of the rear wheel 36R about the swivel axis C2 are locked. Therefore, it is difficult to move the carriage unit 14. In addition, in the first lock mode, both swivel and rotation are locked at the same time. Therefore, even in a case in which rotating force is applied to the carriage unit 14, the unsteadiness of the carriage unit 14 is less than that in a case in which only rotation is locked.

Figure 21:
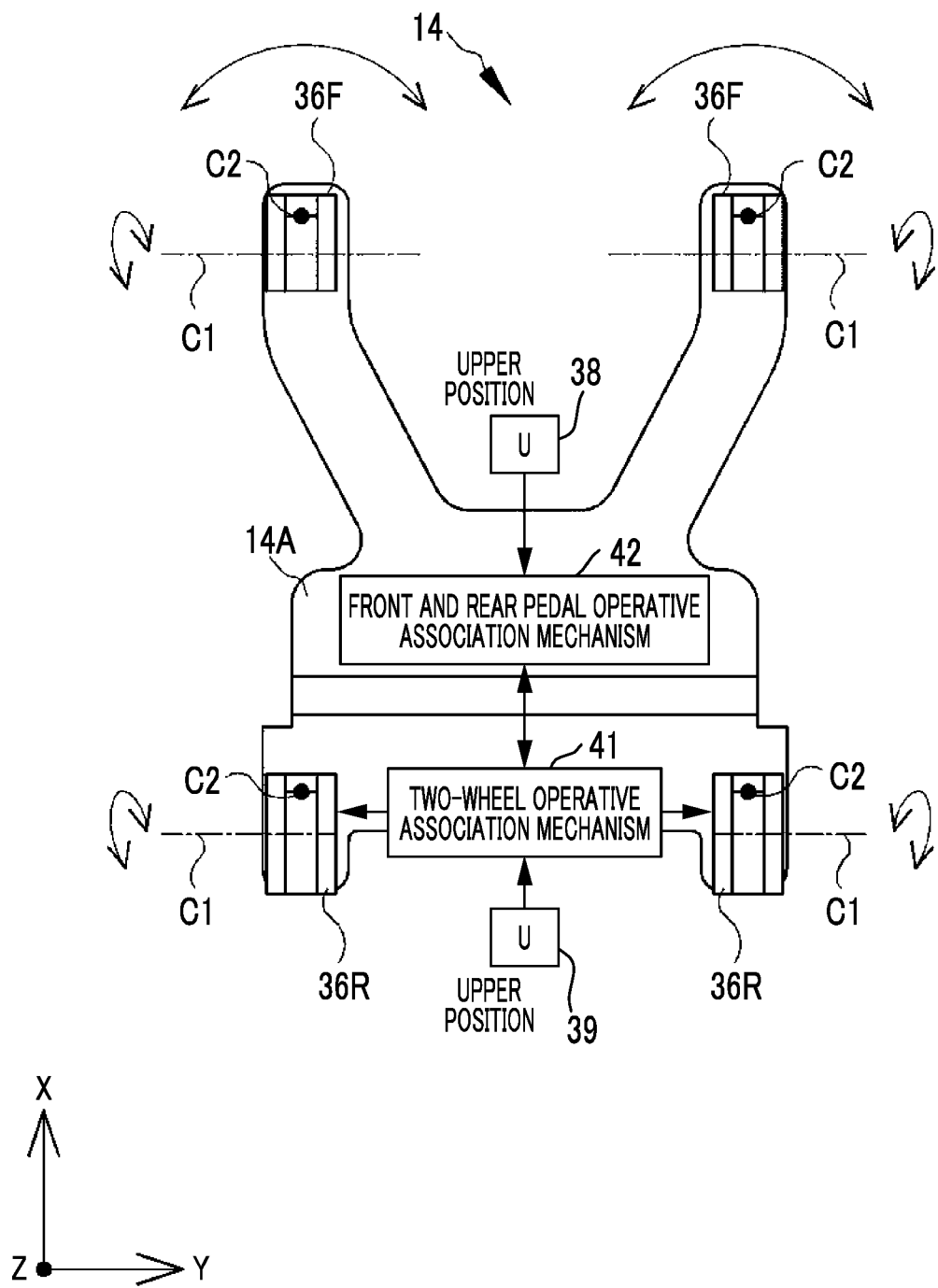
FIG. 21 is a functional diagram illustrating a second lock mode.

As illustrated in FIGS. 18 and 21, in a case in which the pedal position is the upper position, the lock mode is the second lock mode. In the second lock mode, the rotation locking mechanism of the rear wheel 36R is not operated (turned on) and only the swivel locking mechanism of the rear wheel 36R is operated (turned on). That is, the rotation lock is released (turned-off) and only the swivel lock is operated (turned on).

As illustrated in FIG. 21, since the rear wheel 36R can rotate about the axle C1, it is possible to run the carriage unit 14. The configuration in which only the swivel of the rear wheel 36R about the swivel axis C2 is locked has the following advantages. For example, in a case in which the handle 19 is pushed to run the carriage unit 14, it is easy to turn the corner. In a case in which the swivel of the rear wheel 36R is locked, it is possible to prevent the rear wheel 36R of the carriage unit 14 from sliding to the outside of the corner due to the action of centrifugal force. In a case in which the direction of the carriage unit 14 is changed at a fixed position, if only the swivel of the rear wheel 36R is locked, the rear wheel 36R rotates, which makes it easy to change the direction using the rear wheel 36R as a base point.

Figure 22:
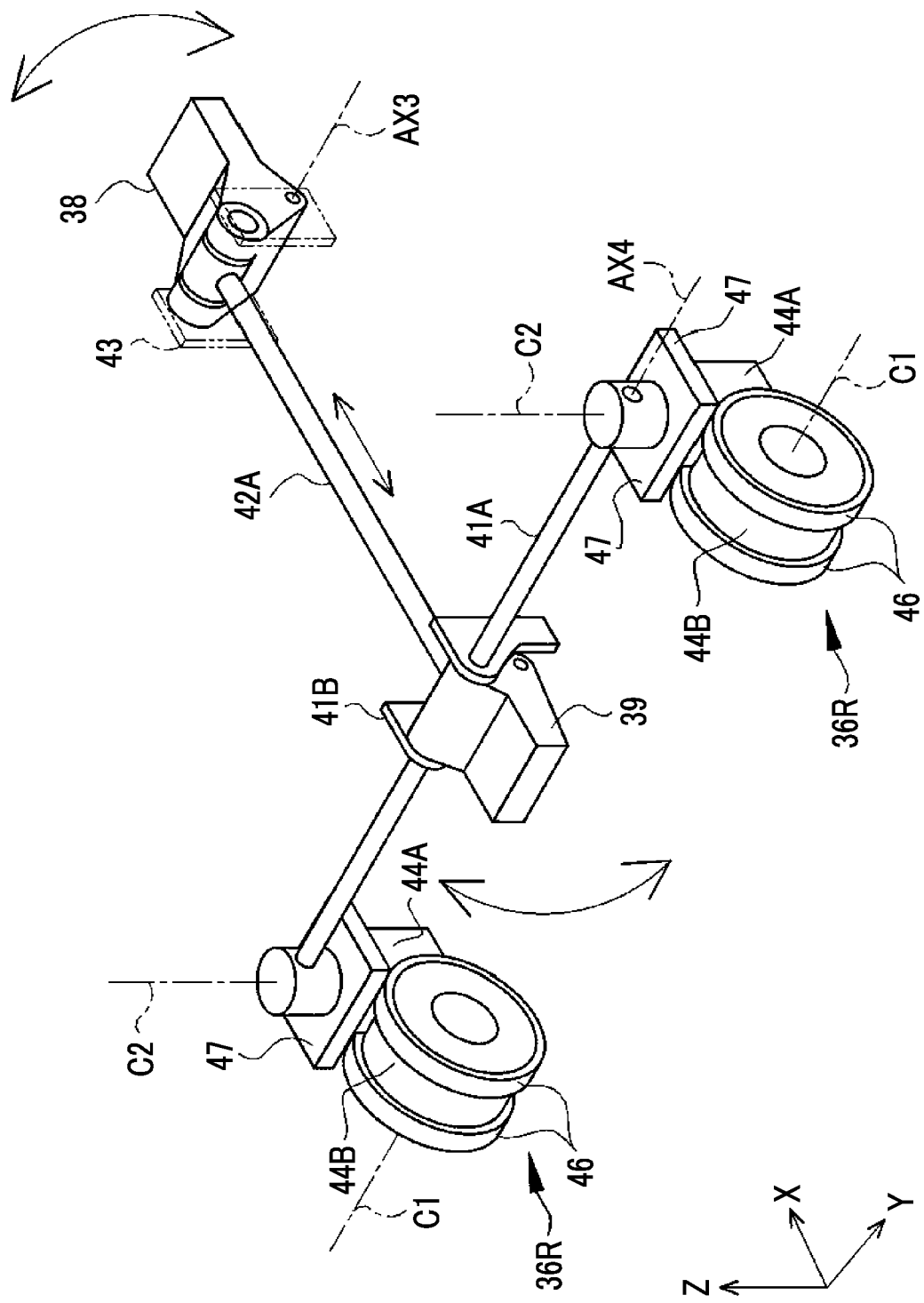
FIG. 22 is a configuration diagram illustrating a two-wheel operative association mechanism and a front and rear pedal operative association mechanism.

As illustrated in FIG. 22, the two-wheel operative association mechanism 41 includes, for example, a two-wheel connection rod 41A. The two-wheel connection rod 41A connects two rear wheels 36R and operatively associates the rotation locking mechanism and the swivel locking mechanism provided in each rear wheel 36R which will be described below. The two-wheel connection rod 41A extends such that the longitudinal direction thereof is the width direction (Y-axis direction) and the rear pedal 39 is attached to a substantially central portion of the two-wheel connection rod 41A. The front pedal 38 is attached to the frame 14A by a supporting metal part 43. Similarly to the rear pedal 39, the front pedal 38 is provided substantially at the center of the carriage unit 14 in the width direction (Y-axis direction).

The rear pedal 39 is rotatable about an axis AX4 that is aligned with the longitudinal axis of the two-wheel connection rod 41A. In a case in which the rear pedal 39 is moved from the initial position to the upper position, the two-wheel connection rod 41A rotates about the axis AX4 in a clockwise direction. On the contrary, in a case in which the rear pedal 39 is moved from the initial position to the lower position, the two-wheel connection rod 41A rotates in a counterclockwise direction. The operating force of the rear pedal 39 is transmitted to the two rear wheels 36R through the two-wheel connection rod 41A. A supporting metal part 41B is attached to the frame 14A and rotatably supports the two-wheel connection rod 41A and the rear pedal 39.

Figure 23:
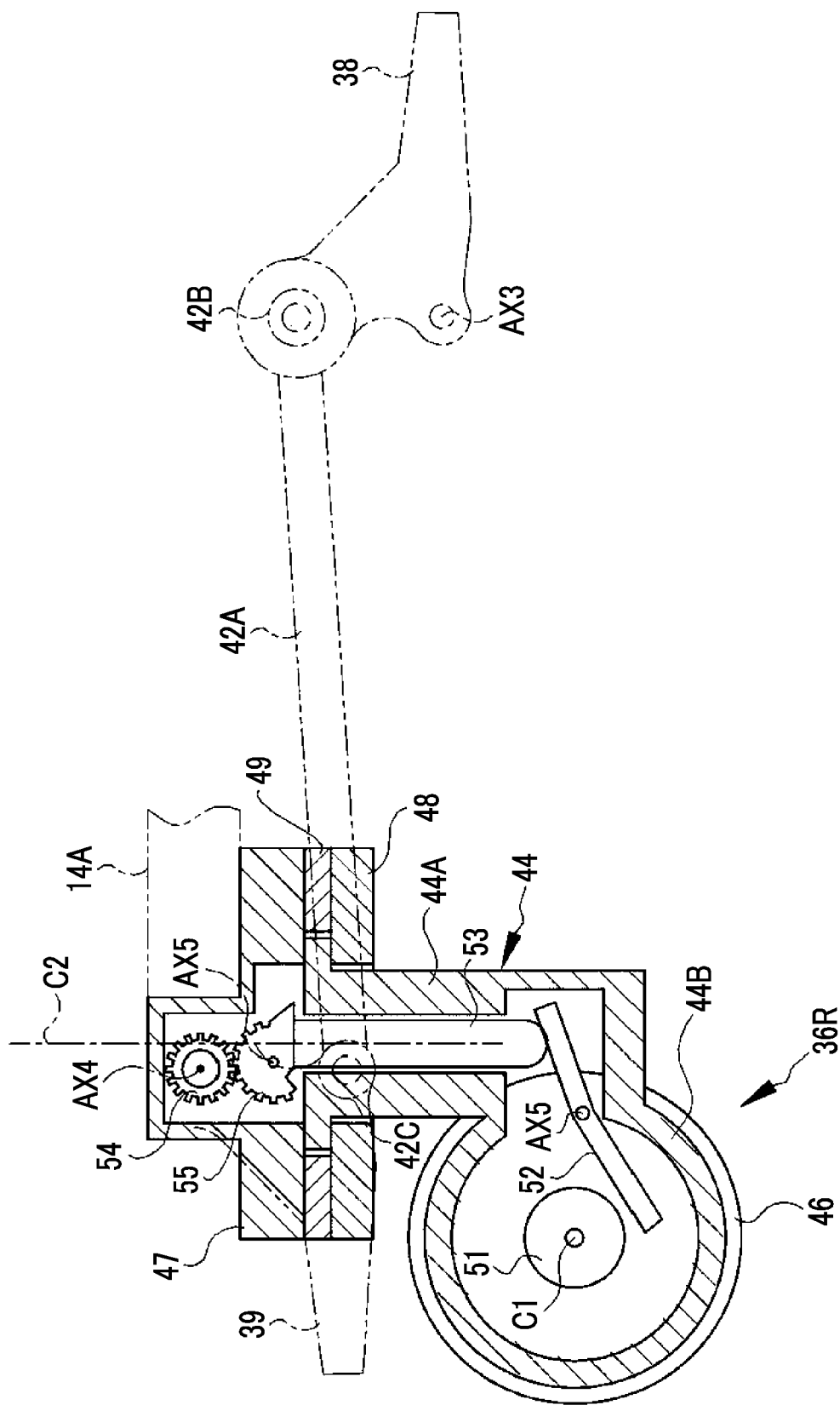
FIG. 23 is a configuration diagram illustrating an unlocked state.
Figure 24:
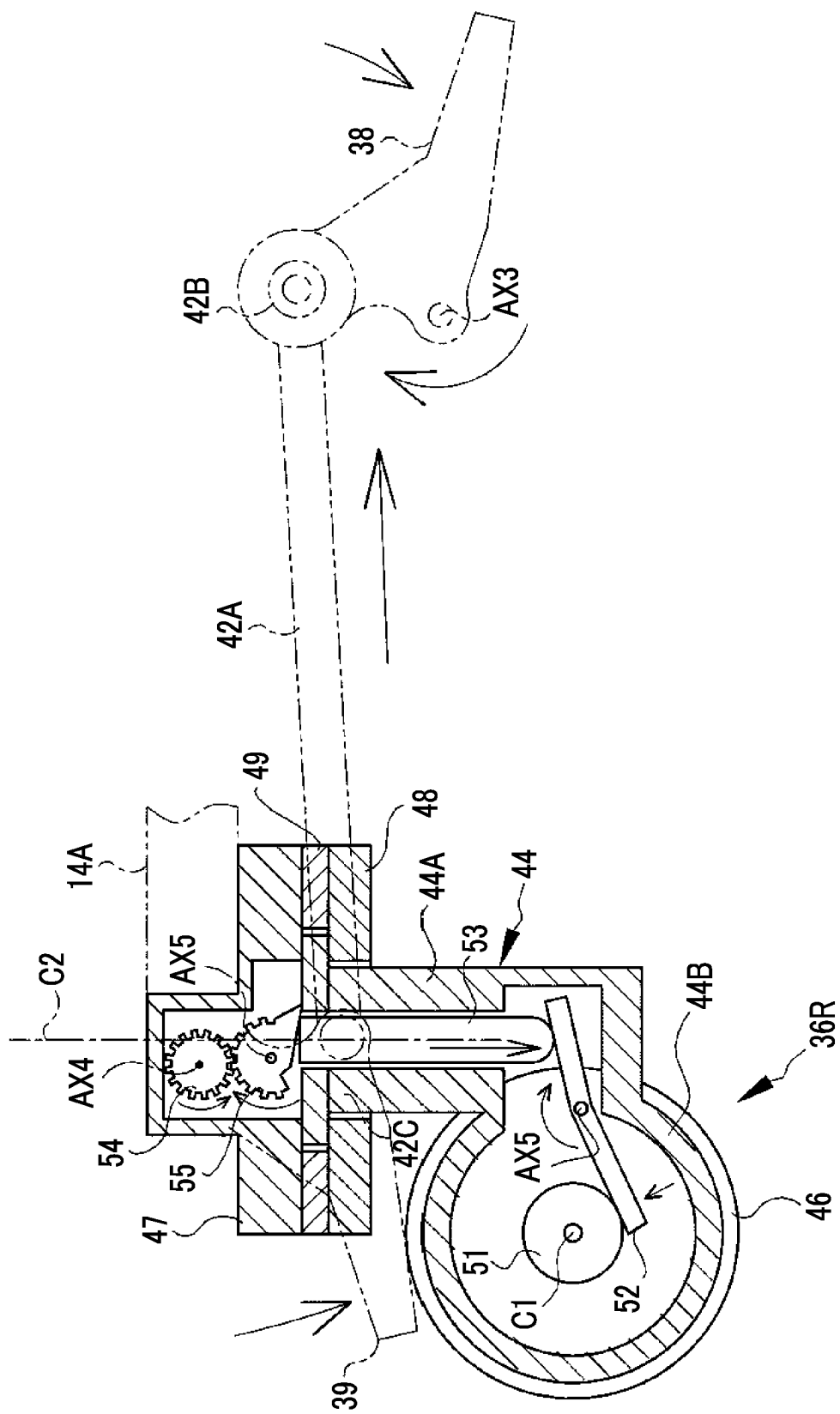
FIG. 24 is a configuration diagram illustrating the first lock mode.
Figure 25:
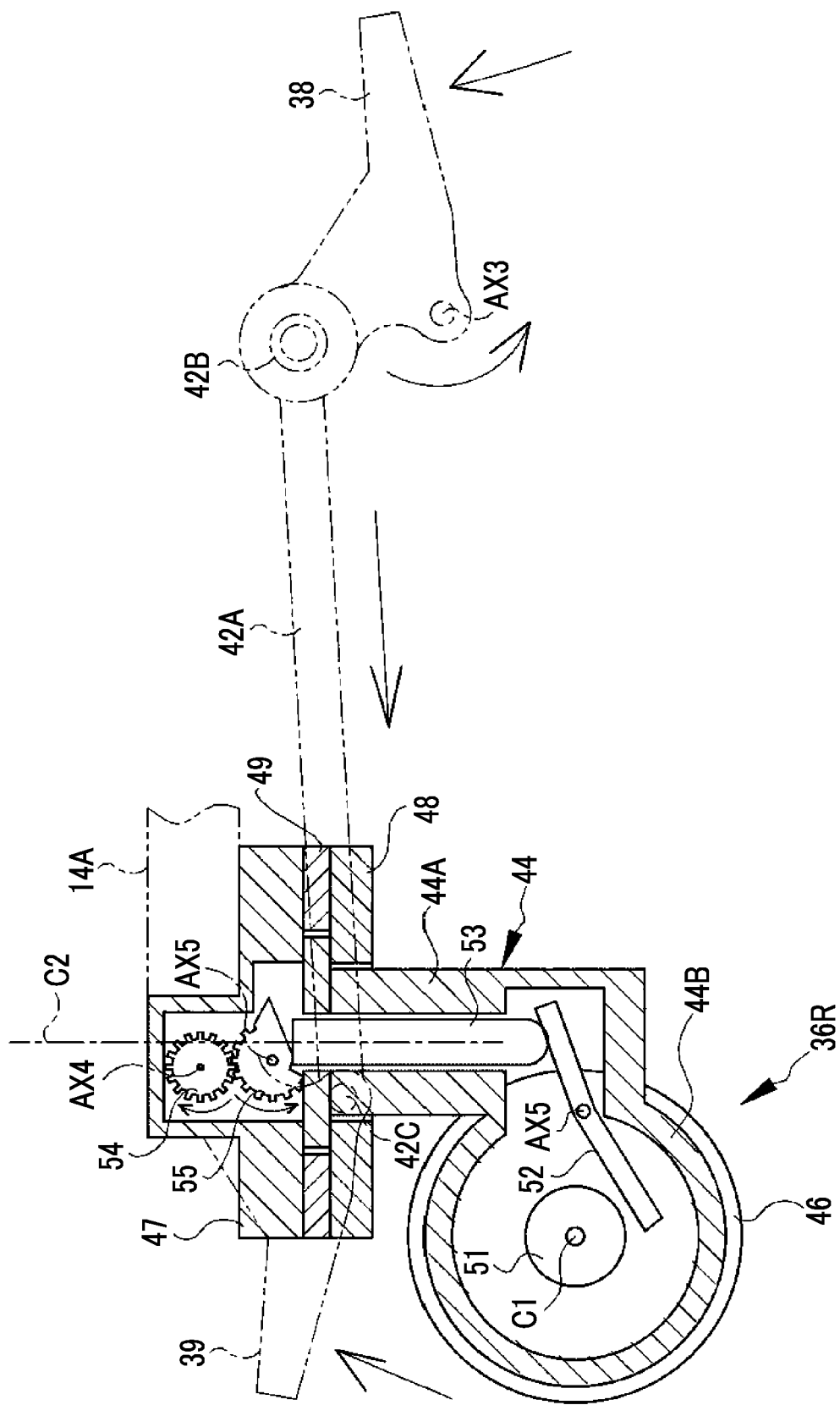
FIG. 25 is a configuration diagram illustrating the second lock mode.

The front and rear pedal operative association mechanism 42 includes, for example, a front and rear operative association rod 42A. As illustrated in FIGS. 23 to 25, the front and rear operative association rod 42A extends in the front-rear direction (X-axis direction) of the carriage unit 14 and has a rear end portion 42C attached to the rear pedal 39 and a leading end portion 42B attached to the front pedal 38. The front and rear operative association rod 42A rotates the front pedal 38 about an axis AX3 in operative association with the rotation of the rear pedal 39 about the axis AX4. In the rear pedal 39, the attachment position of the front and rear operative association rod 42A is offset downward from the axis AX4. Therefore, in a case in which the rear pedal 39 rotates about the axis AX4, the front and rear operative association rod 42A is moved in the front-rear direction (X-axis direction).

In the front pedal 38, the attachment position of the front and rear operative association rod 42A is offset upward from the axis AX3. Therefore, in a case in which the front and rear operative association rod 42A is moved in the front-rear direction, rotating force about the axis AX3 acts on the front pedal 38. In this way, the front pedal 38 is operatively associated with the movement of the rear pedal 39.

In the front pedal 38, the attachment position of the leading end portion 42B of the front and rear operative association rod 42A is offset upward from the axis AX3 about which the front pedal 38 rotates. In contrast, in the rear pedal 39, the attachment position of the rear end portion 42C of the front and rear operative association rod 42A is offset downward from the axis AX4 about which the rear pedal 39 rotates. Therefore, in a case in which the front and rear operative association rod 42A is moved to one side in the front-rear direction, the front pedal 38 and the rear pedal 39 rotate in an opposite direction.

For example, in a case in which the front pedal 38 is pressed from the initial position to the lower position as illustrated in FIG. 24, the front pedal 38 rotates about the axis AX3 in the clockwise direction. Since the front and rear operative association rod 42A is moved forward by the rotation, the rear pedal 39 rotates about the axis AX4 in the counterclockwise direction. In contrast, in a case in which the front pedal 38 is pressed from the initial position to the upper position as illustrated in FIG. 25, the front pedal 38 rotates about the axis AX3 in the counterclockwise direction. Since the front and rear operative association rod 42A is moved backward by the rotation, the rear pedal 39 rotates about the axis AX4 in the clockwise direction.

Therefore, in a case in which one of the front pedal 38 and the rear pedal 39 is moved to any one of the initial position, the upper position, and the lower position, the other pedal can be moved to the same position in operative association with the one pedal. Specifically, as illustrated in FIG. 24, in a case in which one of the pedals is moved to the lower position, the other pedal is also moved to the lower position. As illustrated in FIG. 25, in a case in which one of the pedals is moved to the upper position, the other pedal is also moved to the upper position. According to this structure, the user can operate both the front pedal 38 and the rear pedal 39 with the same feeling. Therefore, operability is high.

As illustrated in FIG. 23, the rear wheel 36R includes, for example, a caster frame 44, a wheel portion 46, a supporting portion 47, and a cover metal part 48. The caster frame 44 includes a main body portion 44A and a wheel attachment portion 44B that is provided behind a lower end of the main body portion 44A. The wheel attachment portion 44B has a substantially cylindrical shape. The wheel portions 46 are attached to both sides of the wheel attachment portion 44B in the Y-axis direction so as to be rotatable about the axle C1. The wheel portion 46 is, for example, a rubber or resin tire.

The supporting portion 47 is fixed to the frame 14A. The caster frame 44 is supported by the supporting portion 47 so as to rotate about the swivel axis C2. The cover metal part 48 covers a flange formed at an upper end of the caster frame 44 from the upper side and is used to attach the caster frame 44 to the supporting portion 47. A spacer 49 corresponding to the thickness of the flange of the caster frame 44 is provided between the cover metal part 48 and the supporting portion 47.

A rotating body 51 that rotates along with the wheel portion 46 is provided in the wheel attachment portion 44B. The rotating body 51 has a cylindrical shape and a brake lever 52 is provided in the vicinity of the outer circumference of the rotating body 51. The brake lever 52 comes into contact with the outer circumference of the rotating body 51 to generate frictional force against a rotation direction, thereby locking the rotation of the wheel portion 46.

The brake lever 52 is provided so as to be swingable about an axis AX5. A push rod 53 that extends in the vertical direction (Z-axis direction) is provided in the main body portion 44A. The push rod 53 is urged upward by urging means (not illustrated) such as a spring. In a case in which the push rod 53 receives pressing force from the upper side and is pressed down against urging force, a lower end of the push rod 53 comes into contact with one end of the brake lever 52 to swing the brake lever 52 in the clockwise direction. Then, the other end of the brake lever 52 comes into contact with the rotating body 51 to lock rotation.

A gear 54 that is connected to an end portion of the two-wheel connection rod 41A and a cam 55 that is engaged with the gear 54 and is rotated are provided in the supporting portion 47. The gear 54 rotates about the axis AX4 with the rotation of the two-wheel connection rod 41A. The cam 55 is provided so as to be rotatable about the axis AX5 that extends in the Y-axis direction similarly to the axis AX4. The cam 55 rotates in a direction opposite to the rotation direction of the gear 54 in operative association with the rotation of the gear 54.

In a case in which the pedal position is moved from the initial position to the lower position as illustrated in FIG. 24, the gear 54 rotates in the counterclockwise direction and the cam 55 rotates in the clockwise direction. In a case in which the cam 55 rotates in the clockwise direction, the cam 55 presses the upper end of the push rod 53. The push rod 53 receives the pressing force and is moved downward to swing the brake lever 52. In this way, rotation is locked.

In addition, the cam 55 comes into contact with an upper end surface of the main body portion 44A of the caster frame 44. The swivel of the caster frame 44 about the swivel axis C2 is locked by the frictional force between the cam 55 and the main body portion 44A. In a case in which the pedal position is moved from the lower position to the initial position, the cam 55 rotates in the counterclockwise direction. In a case in which the cam 55 returns to the initial position, the pressing force applied to the push rod 53 is released. In a case in which the pressing force is released, urging force acts to move the push rod 53 upward. Then, rotation is unlocked. In a case in which the cam 55 is moved to the initial position, the contact between the cam 55 and the main body portion 44A is released and swivel is unlocked.

In a case in which the pedal position is moved from the initial position to the upper position as illustrated in FIG. 25, the gear 54 rotates in the clockwise direction and the cam 55 rotates in the counterclockwise direction. In a case in which the cam 55 rotates in the counterclockwise direction, an end portion of the cam 55 which is opposite to the end portion illustrated in FIG. 24 comes into contact with the upper end surface of the main body portion 44A of the caster frame 44. The swivel of the caster frame 44 about the swivel axis C2 is locked by the frictional force between the cam 55 and the main body portion 44A. In addition, in a case in which the cam 55 rotates in the counterclockwise direction, the upper end of the push rod 53 is fitted to a notch that is formed in the lower end surface of the cam 55. Therefore, unlike the case illustrated in FIG. 24, the pressing force against the push rod 53 does not act and rotation is not locked.

As described above, in this embodiment, the gear 54, cam 55, the push rod 53, the brake lever 52, and the rotating body 51 form the rotation locking mechanism. In addition, the gear 54, the cam 55, and the main body portion 44A form the swivel locking mechanism. The front pedal 38 and the rear pedal 39 are operation members for the locking operation and the unlocking operation of the rotation locking mechanism and the swivel locking mechanism.

(Operation)

Next, the operation of the above-mentioned configuration will be described. In a case in which the medical staff ST performs visit imaging, the medical staff ST holds the handle 19 from the rear side of the treatment cart 11 and runs the carriage unit 14 to visit the hospital rooms. In a case in which the medical staff ST moves to the hospital room, for example, the medical staff ST moves the rear pedal 39 to the upper position to select the second lock mode. Then, the swivel of the rear wheel 36R is locked. Therefore, the rear wheel 36R does not skid sideways even at the corner and it is possible to run the treatment cart 11 in a stable posture.

Figure 26:
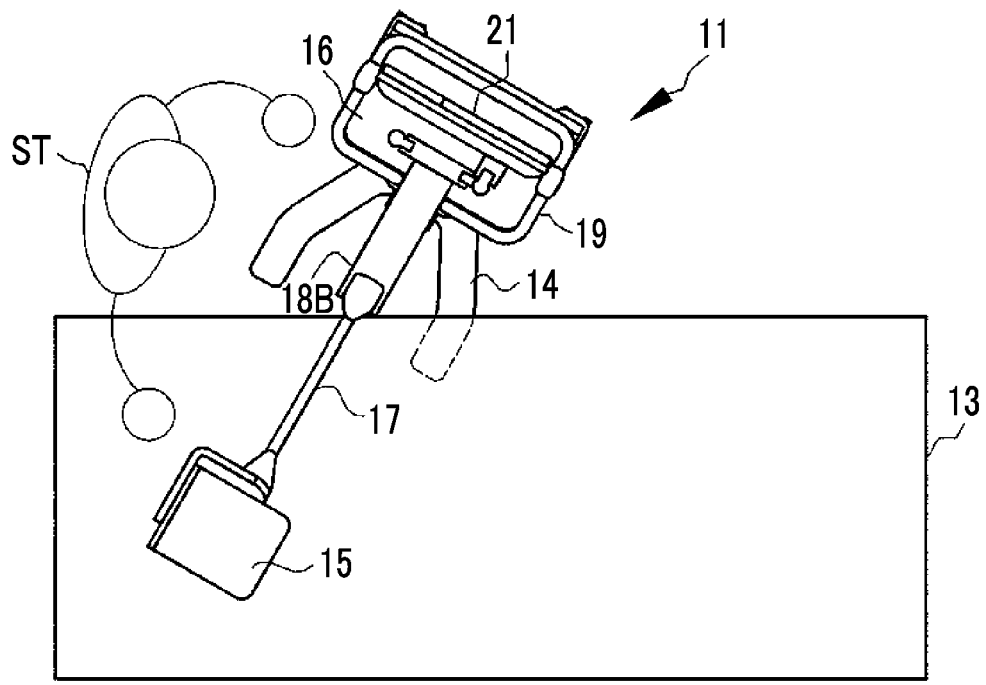
FIG. 26 is a first diagram illustrating an aspect of the positioning of an X-ray emitting unit.
Figure 27:
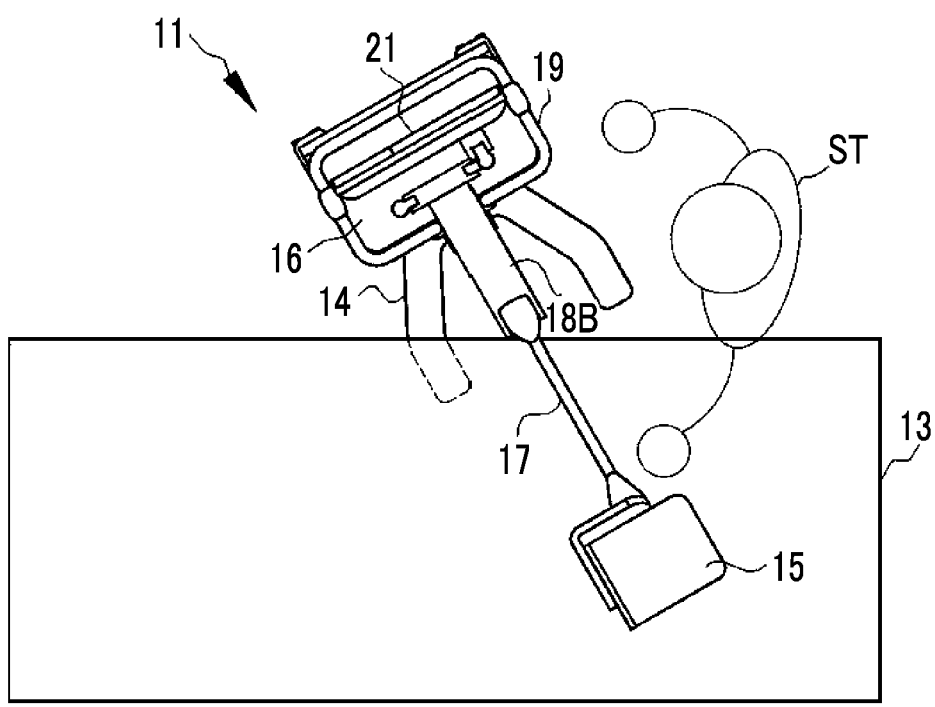
FIG. 27 is a second diagram illustrating an aspect of the positioning of the X-ray emitting unit.

As illustrated in FIGS. 26 and 27, in the hospital room, the treatment cart 11 and/or the X-ray emitting unit 15 is moved to position the X-ray emitting unit 15. First, the position of the electronic cassette 12 is determined according to the imaging part of the object H (see FIG. 1) on the bed 13. Then, the X-ray emitting unit 15 is positioned such that the electronic cassette 12 and the X-ray emitting unit 15 face each other.

Figure 28:
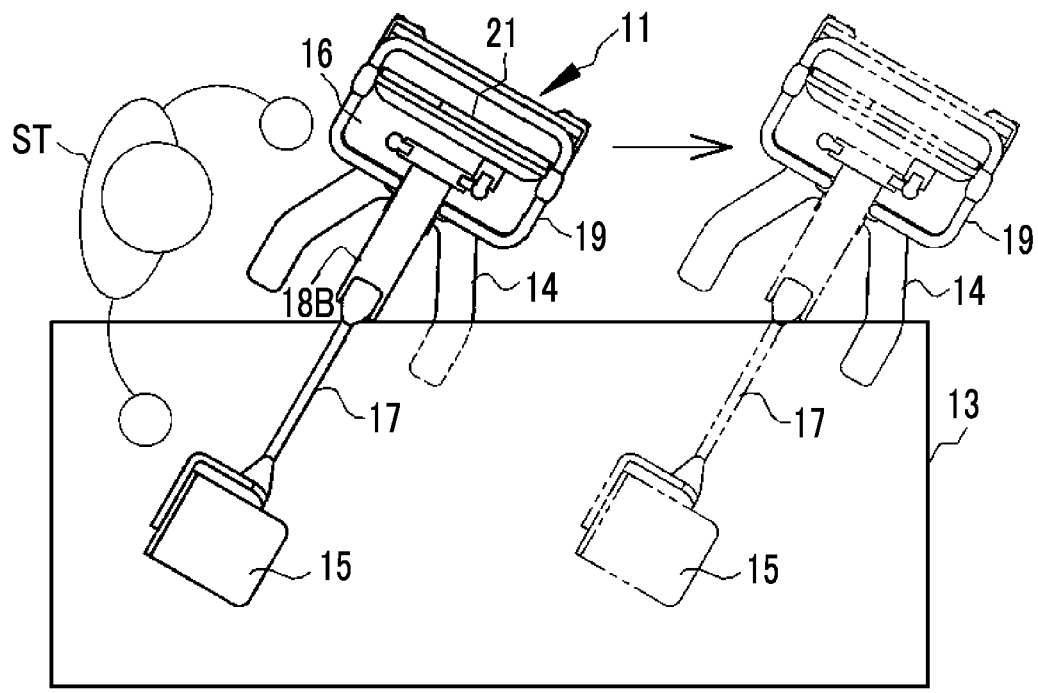
FIG. 28 is a third diagram illustrating an aspect of the positioning of the X-ray emitting unit.

In the treatment cart 11, the main body unit 16 is small and light and the front wheel 36F and the rear wheel 36R are casters that can swivel independently. Therefore, the mobility of the carriage unit 14 is high. In addition, since two casters forming the rear wheel 36R are not always changed in the same phase, but are independently changed, the mobility of the carriage unit 14 is high. Therefore, the X-ray emitting unit 15 can be roughly positioned by moving the carriage unit 14 or changing the direction. As illustrated in FIG. 28, the carriage unit 14 may be slid in the horizontal direction or an oblique direction as well as the front-rear direction.

In a case in which the carriage unit 14 is moved in this way, the pedal position is moved to the initial position to change to an unlocked state. In the unlocked state, since both the rotation locking mechanism and the swivel locking mechanism of the rear wheel 36R are released, both the front wheel 36F and the rear wheel 36R are rotatable. Therefore, the carriage unit 14 can be moved in various ways. For example, the carriage unit 14 can be slid or the direction of the carriage unit 14 can be changed at a fixed position.

In the positioning of the X-ray emitting unit 15, the medical staff ST generally stands between the bed 13 and the treatment cart 11. The reason is that the X-ray emitting unit 15 is disposed in front of the treatment cart 11 and the medical staff ST needs to finely adjust the position of the object on the bed 13 and/or the electronic cassette 12. Since the front pedal 38 is provided in the treatment cart 11, it is easy to lock or unlock the rear wheel 36R from the front side.

Figure 29:
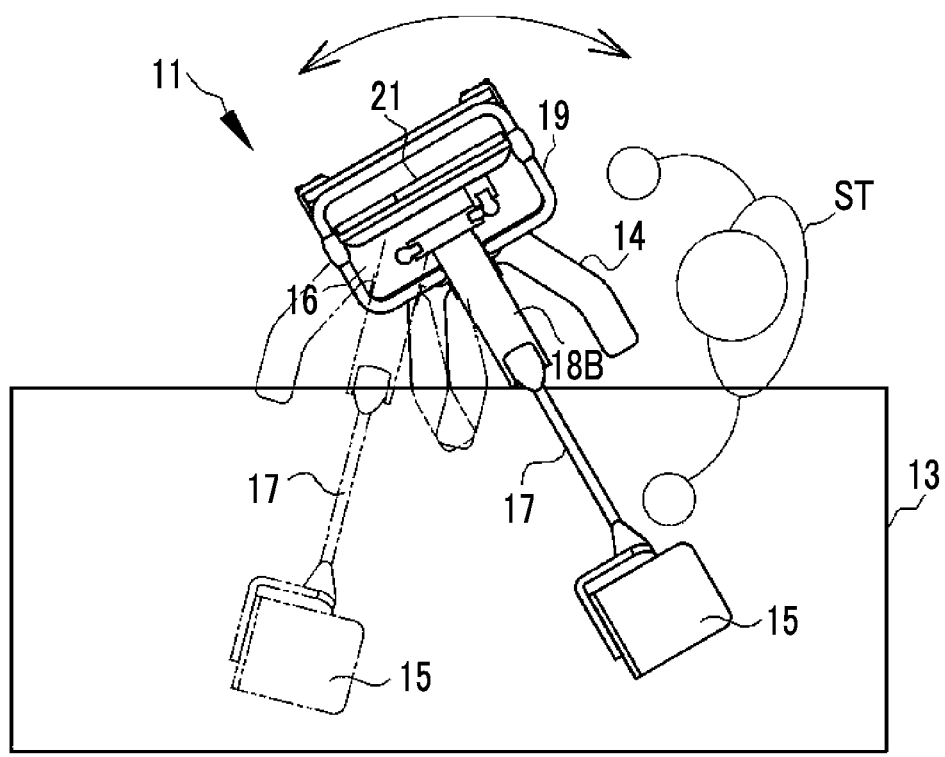
FIG. 29 is a fourth diagram illustrating an aspect of the positioning of the X-ray emitting unit.

As illustrated in FIG. 29, since the front wheel 36F is a caster that can swivel, it is possible to change the direction of the carriage unit 14 using the rear portion of the carriage unit 14 as a base point. In this case, the pedal position is moved to the upper position to select the second lock mode, thereby locking the swivel of the rear wheel 36R. Then, the unsteady motion of the rear portion of the carriage unit 14 is prevented. Therefore, the carriage unit 14 can be smoothly rotated to change the position of the X-ray emitting unit 15.

In addition, the main body unit 16 is thin and the height of the leading end portion of the carriage unit 14 is small. Therefore, the carriage unit 14 can get into a clearance space below the bed 13 such that the main body unit 16 is close to the bed 13. The X-ray emitting unit 15 supported by the support 18 of the main body unit 16 can reach the inside of the bed 13 above the bed 13.

Figure 30:
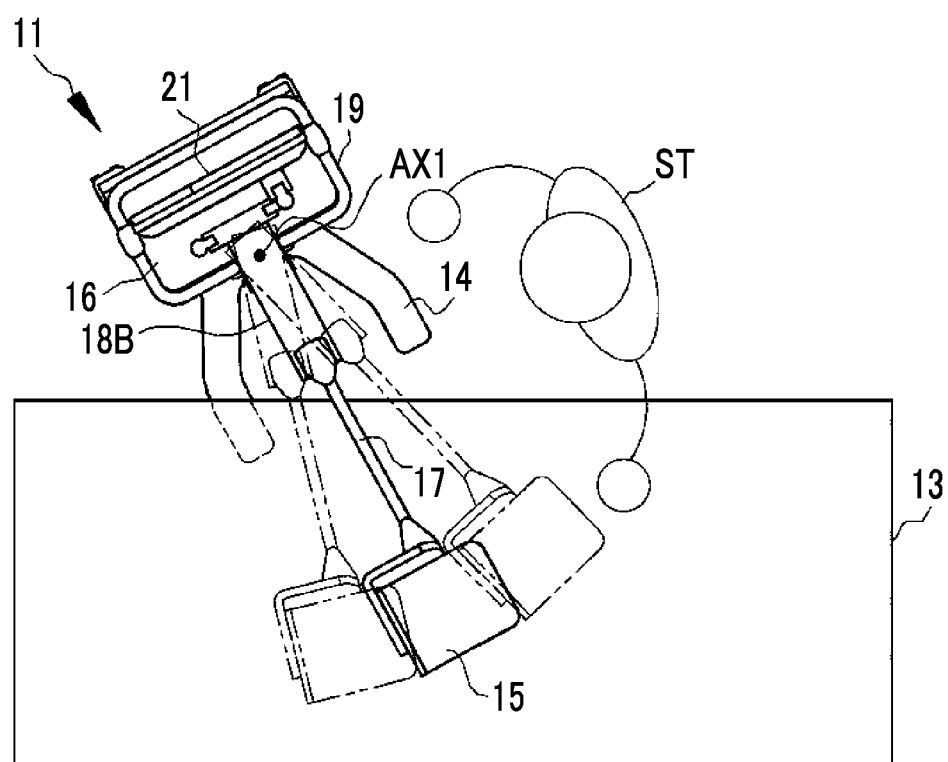
FIG. 30 is a fifth diagram illustrating an aspect of the positioning of the X-ray emitting unit.

In a case in which the carriage unit 14 is moved and rough positioning ends, the pedal position is changed to the lower position and the rear wheel 36R is locked in the first lock mode such that the position and posture of the carriage unit 14 are not changed. In the treatment cart 11, the second support portion 18B rotates about the rotation axis AX1 with respect to the carriage unit 14. Therefore, as illustrated in FIG. 30, it is possible to finely adjust the position of the X-ray emitting unit 15 in a state in which the position and direction of the carriage unit 14 are fixed. In this case, in the first lock mode, since both the rotation and swivel of the rear wheel 36R are locked, the unsteadiness of the carriage unit 14 can be less than that in a case in which only rotation is locked.

In particular, in a case in which the second support portion 18B is rotated, rotating force about the rotation axis AX1 that extends in the Z-axis direction acts on the carriage unit 14. The rear wheel 36R swivels about the swivel axis C2 extending in the Z-axis direction. Therefore, in a case in which the swivel of the rear wheel 36R is not locked, the carriage unit 14 becomes unsteady. In a case in which the first lock mode is used, both the rotation and swivel of the rear wheel 36R are locked. Therefore, the unsteadiness of the carriage unit 14 can be less than that in the related art. As a result, it is possible to rotate the second support portion 18B in a stable posture.

The first lock mode can be selected by one operation of moving the front pedal 38 or the rear pedal 39 to the lower position. That is, both rotation lock and swivel lock can be performed (turned on) at the same time by one operation. Therefore, operability is higher than that in a case in which two types of locking are performed by different operations. In addition, in this embodiment, since the front pedal 38 and the rear pedal 39 have the same function, the same operation can be performed from the front and rear sides.

Furthermore, since both the front pedal 38 and the rear pedal 39 are provided, it is possible to perform a locking operation from a rear position, similarly to the related art. The first lock mode or the second lock mode can be selected while the carriage unit 14 is traveling. Therefore, it is possible to perform an operation of selecting the second lock mode while running the carriage unit 14 in a case in which the carriage unit 14 turns the corner or an operation of selecting the first lock mode in a case in which a sudden stop is needed.

In the above-mentioned example, the front pedal 38 and the rear pedal 39 have the same functions. However, some of the functions may be common to front pedal 38 and the rear pedal 39. For example, it is considered that the front pedal 38 can be used to select both the first lock mode and the second lock mode and the rear pedal 39 can be used to select only one of the first lock mode and the second lock mode.

Second Embodiment

A second embodiment relates to an operation panel 21 provided in a main body unit 16. The basic configuration of a treatment cart 11 including a carriage unit 14 is the same as that in the first embodiment. The same parts and members are denoted by the same reference numerals and the description thereof will not be repeated.

Figure 31:
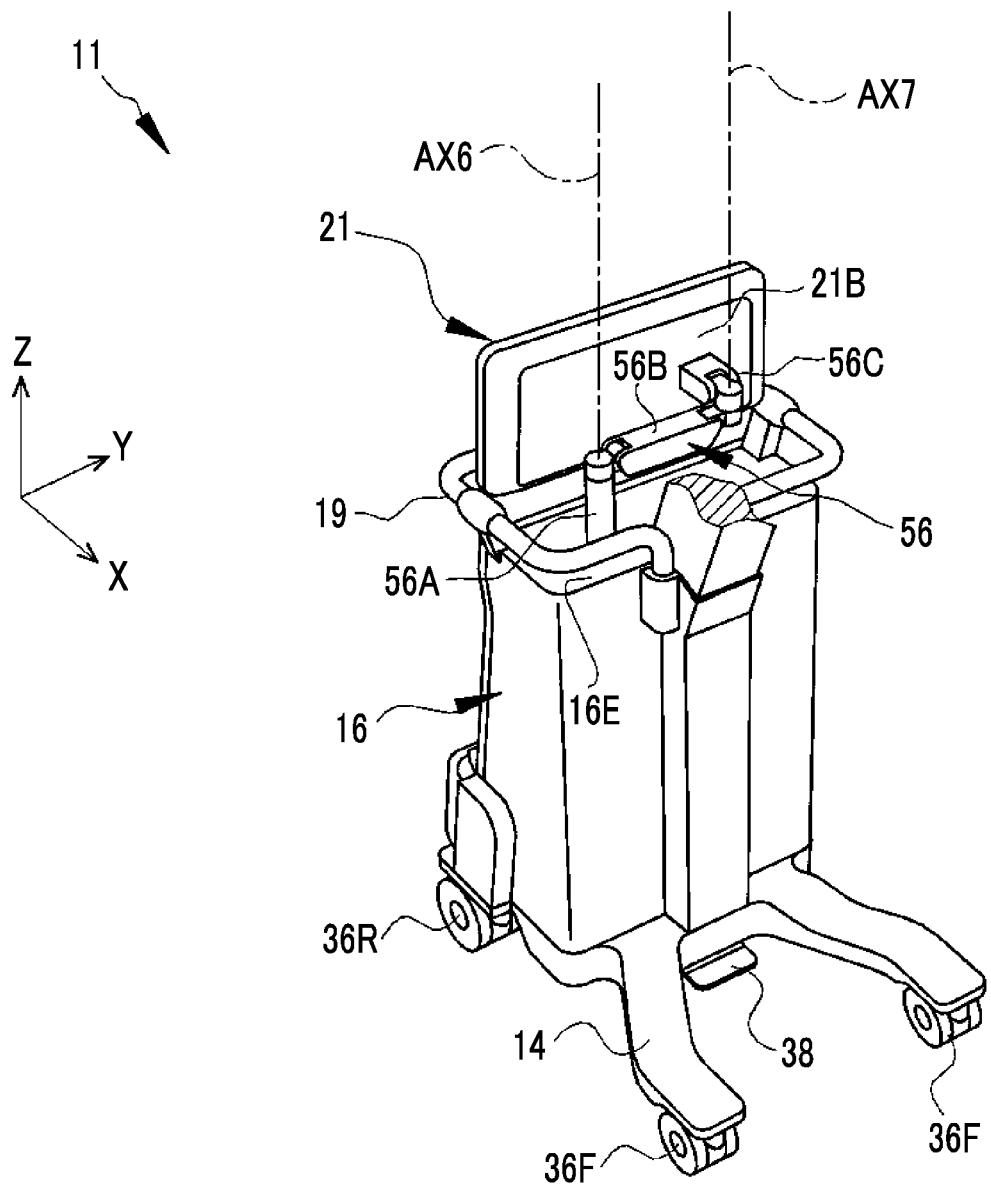
FIG. 31 is a diagram illustrating an attachment arm for an operation panel.
Figure 32:
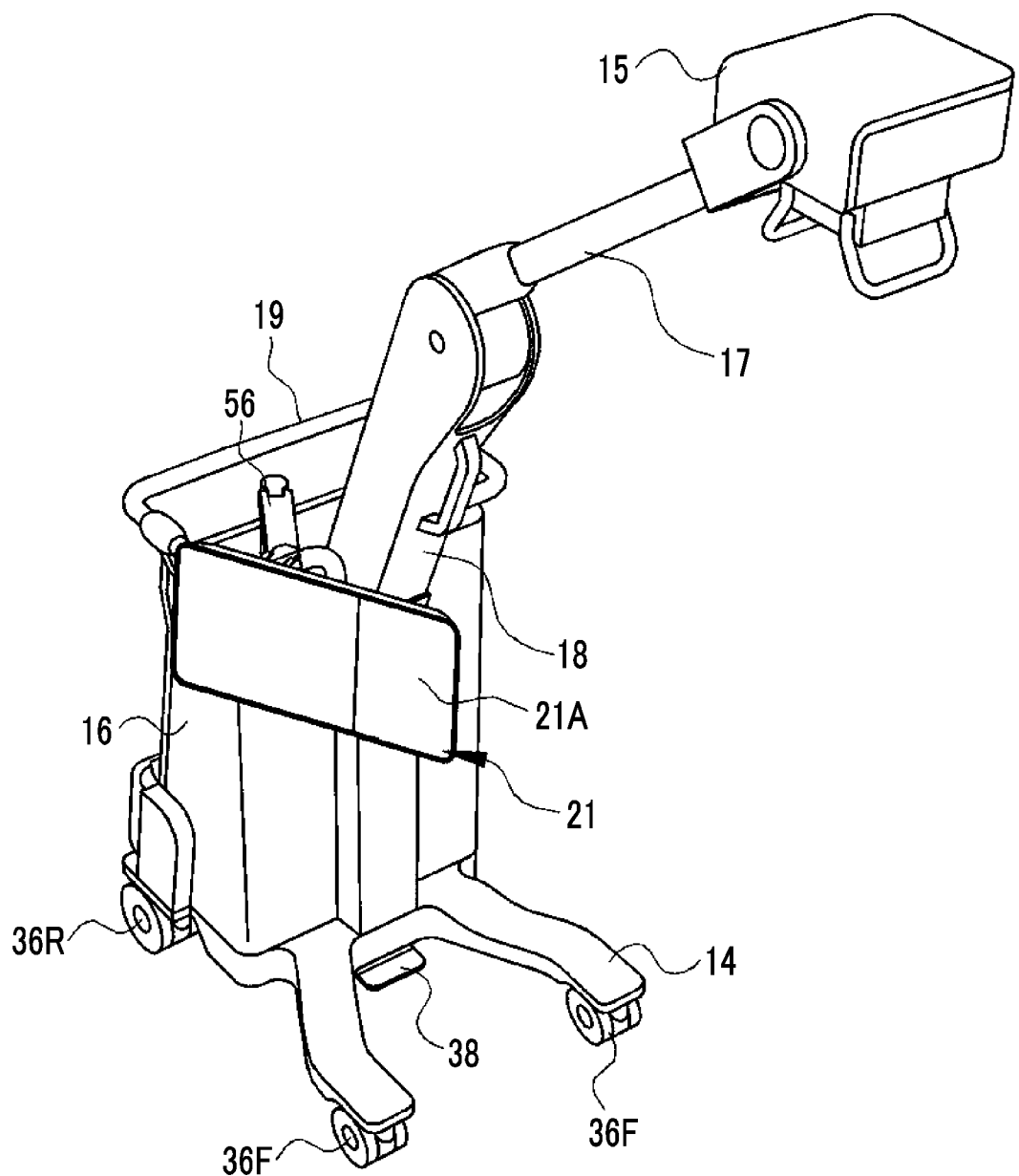
FIG. 32 is a diagram illustrating a state in which the operation panel faces forward.

As illustrated in FIGS. 31 and 32, the operation panel 21 is attached to an upper surface 16E of the main body unit 16 through an attachment arm 56. The attachment arm 56 includes a vertical support portion 56A, a horizontal arm portion 56B, and an attachment portion 56C. The vertical support portion 56A is a support that extends in the Z-axis direction parallel to the vertical direction and vertically stands on the upper surface 16E of the main body unit 16. One end of the horizontal arm portion 56B is attached to an upper end portion of the vertical support portion 56A. The horizontal arm portion 56B has one end attached to the vertical support portion 56A and the other end attached to the operation panel 21. The horizontal arm portion 56B is an arm whose longitudinal axis extends from the vertical support portion 56A in the horizontal direction perpendicular to the Z-axis direction.

In this embodiment, the vertical support portion 56A has a linear longitudinal axis. However, the vertical support portion 56A is not necessarily a linear support as long as it has a length in the vertical direction. The vertical support portion 56A may be bent in the middle or may be inclined in the middle. The concept of extension in the vertical direction includes these aspects. Similarly, in this embodiment, the horizontal arm portion 56B has a linear longitudinal axis. However, the horizontal arm portion 56B may be bent in the middle or may be inclined in the middle as long as it has a length in the horizontal direction. The concept of extension in the horizontal direction includes these aspects.

The height of the operation panel 21 in the vertical direction is greater than the height of the handle 19. Since the operation panel 21 is provided at a high position, the visibility of the operation panel 21 is improved.

The attachment portion 56C is attached to a rear surface 21B opposite to an operation surface 21A which is a front surface of the operation panel 21. The attachment portion 56C is attached to the horizontal arm portion 56B. The horizontal arm portion 56B is provided so as to be rotatable about an axis AX6 that extends in the Z-axis direction with respect to the vertical support portion 56A. In addition, the attachment portion 56C is provided so as to be rotatable about an axis AX7 that extends in the Z-axis direction with respect to the horizontal arm portion 56B. That is, the attachment arm 56 has two joints that rotate about the axis AX6 and the axis AX7 extending in the Z-axis direction. The operation panel 21 is provided so as to be rotatable about an axis that extends in the Z-axis direction with respect to the carriage unit 14.

Figure 33:
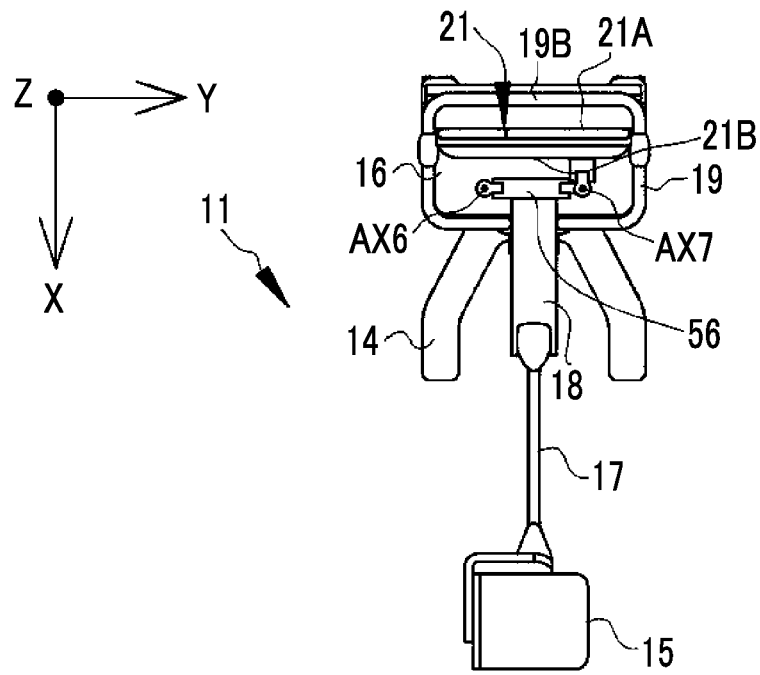
FIG. 33 is a diagram illustrating the operation panel at an initial position.
Figure 34:
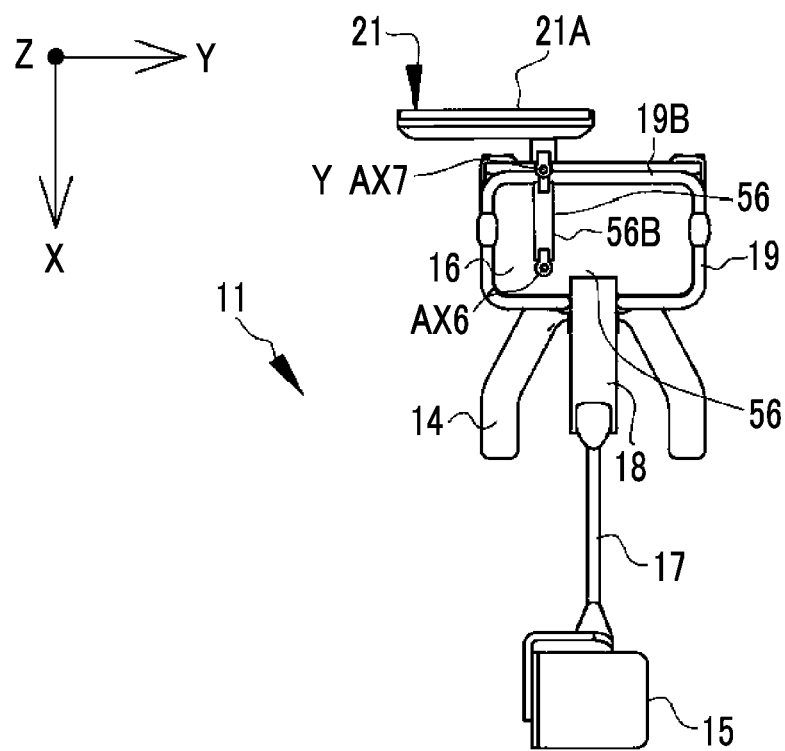
FIG. 34 is a diagram illustrating the operation panel located at a rear position different from the initial position.
Figure 35:
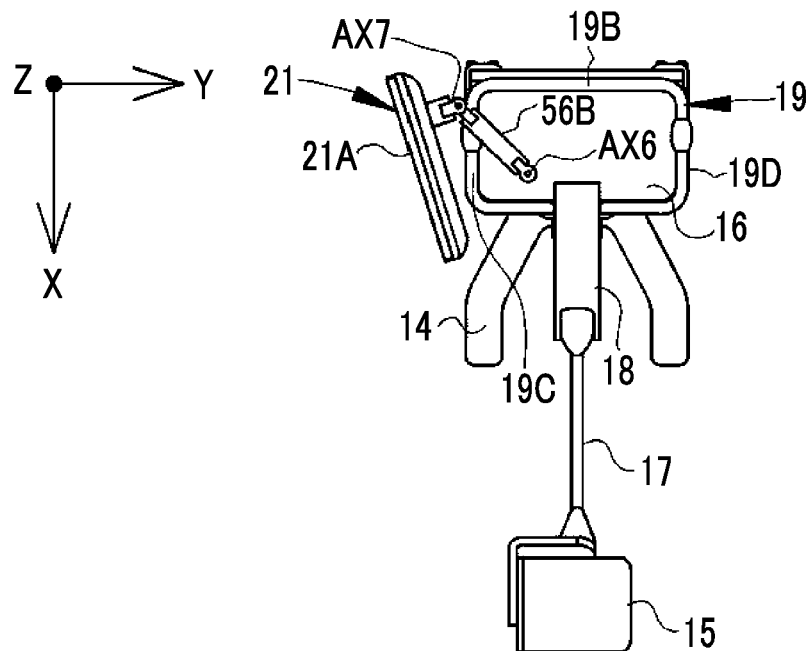
FIG. 35 is a diagram illustrating the operation panel located at a side position.
Figure 36:
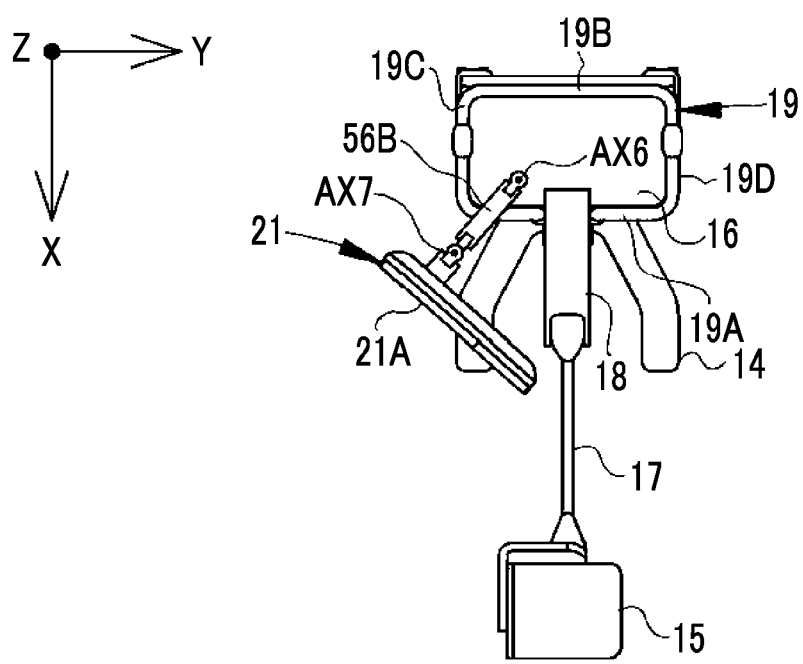
FIG. 36 is a diagram illustrating the operation panel located at a side position different from that illustrated in FIG. 35.
Figure 37:
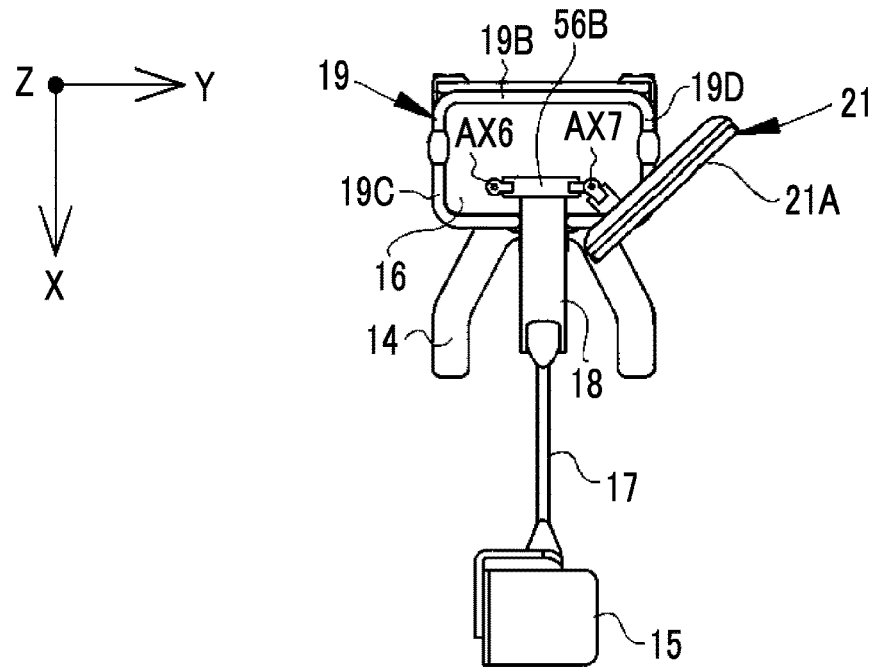
FIG. 37 is a diagram illustrating the operation panel located at the side position opposite to that illustrated in FIG. 36.

As illustrated in FIGS. 33 to 37, the operation panel 21 has at least a movable range from a rear position where the operation surface 21A faces the rear of the carriage unit 14 as illustrated in FIGS. 33 and 34 to a side position where the operation surface 21A faces the side of the carriage unit 14 as illustrated in FIGS. 35 to 37. In a case in which the operation panel 21 is moved to the side position, for example, the medical staff ST stands on the oblique front side of the support 18 as illustrated in FIG. 26 and can operate the operation panel 21 at that position.

As illustrated in FIG. 33, the initial position of the operation panel 21 is the rear position where the operation surface 21A faces backward. At the rear position, the rear surface 21B faces the support 18. At the initial position, the horizontal arm portion 56B extends in the width direction (Y-axis direction) of the main body unit 16 and the operation panel 21 is accommodated inside the handle 19 in the horizontal direction. The medical staff holds the handle 19 from the rear side in a case in which the medical staff runs the treatment cart 11 in the hospital ward. At that time, since the operation panel 21 can be accommodated inside the handle 19 as represented at the initial position, the operation panel 21 does not hinder the medical staff from holding the handle 19. Therefore, it is easy to run the treatment cart 11.

As illustrated in FIG. 34, in a case in which the horizontal arm portion 56B of the attachment arm 56 is rotated backward about the axis AX6 by 90° in the counterclockwise direction from the initial position, the operation panel 21 can be moved outside the handle 19.

As illustrated in FIGS. 35 and 36, in a case in which the horizontal arm portion 56B is further rotated about the axis AX6 in the counterclockwise direction from the position illustrated in FIG. 34, the operation surface 21A of the operation panel 21 can face forward. FIG. 35 illustrates a state in which the operation surface 21A faces sideways and FIG. 36 illustrates a state in which the operation surface 21A faces substantially obliquely forward. At the side position, the operation panel 21 protrudes outward from the handle 19 in the horizontal direction.

The configuration in which the operation panel 21 protrudes outward from the handle 19 at the side position has the advantage that the operability of the operation panel 21 is improved. For example, in a case in which the medical staff ST stands in front of the support 18 and positions the X-ray emitting unit 15 as illustrated in FIG. 26 and in a case in which the medical staff ST sets irradiation conditions, the operation panel 21 is operated. In a case in which the operation panel 21 protrudes outward from the handle 19 as illustrated in FIGS. 35 and 36, the operation panel 21 is located in front of the handle 19 as viewed from the medical staff ST who stands in front of the operation panel 21. Therefore, the handle 19 does not hinder the operation of the operation panel 21 and operability is high.

As illustrated in FIG. 37, in a case in which only the attachment portion 56C is rotated about the axis AX7 in the clockwise direction with the horizontal arm portion 56B in the same state as that at the initial position (FIG. 33), it is possible to move the operation panel 21 to a side position opposite to the position illustrated in FIGS. 35 and 36.

As such, the operation panel 21 is provided so as to be rotatable about the axis extending in the Z-axis direction. The medical staff ST can rotate the operation panel 21 about the axis extending in the Z-axis direction to change the direction of the operation panel 21, depending on the position of the medical staff ST. However, in a case in which the operation panel 21 is rotated, rotating force about the axis extending in the Z-axis direction acts on the carriage unit 14 as in the first embodiment in which the arm unit 17 is rotated. Therefore, the carriage unit 14 is unsteady and unstable.

As described above, the treatment cart 11 has the first lock mode in which the rotation locking mechanism and the swivel locking mechanism of the rear wheel 36R are operated at the same time. Similarly to the first embodiment, the first lock mode can be used to solve the above-mentioned problems. That is, in a case in which the first lock mode is used, the rotation and swivel of the rear wheel 36R are locked. Therefore, it is possible to reliably prevent the unsteadiness of the carriage unit 14. In addition, since the first lock mode can be selected by the operation of the front pedal 38 or the rear pedal 39, the selection operation is simplified. Furthermore, since the front pedal 38 is provided, the medical staff ST who operates the operation panel 21 in front of the support 18 operates the front pedal 38 to select the first lock mode from the front side. Therefore, it is easy to adjust the position of the operation panel 21.

Third Embodiment

A third embodiment illustrated in FIGS. 38 to 44 relates to an operation panel 21 provided in a main body unit 16, similarly to the second embodiment. The third embodiment relates to the relative relationship between an attachment arm 56 and a handle 19. The basic configuration of each portion of a treatment cart 11 is the same as that in the first embodiment. The attachment arm 56, the handle 19, and the operation panel 21 have the same configuration as those in the second embodiment. The same parts and members are denoted by the same reference numerals and the description thereof will not be repeated.

Figure 38:
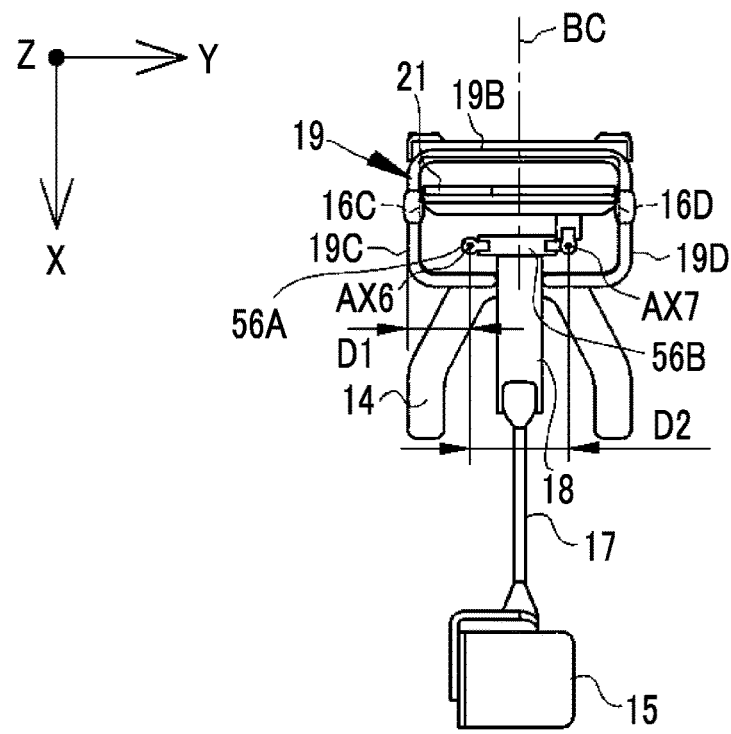
FIG. 38 is a first diagram illustrating a third embodiment.

As illustrated in FIG. 38, the vertical support portion 56A of the attachment arm 56 is provided at a position that is closer to the other side bar portion 19C on the left side than to one side bar portion 19D on the right side, as viewed from the front side of the treatment cart 11. That is, the position of the vertical support portion 56A is offset to the left from a center position BC of the main body unit 16 in the width direction as viewed from the front side. In a case in which the distance from the vertical support portion 56A to the side bar portion 19C close to the vertical support portion 56A is D1, a length D2 from one end of the horizontal arm portion 56B which is attached to the vertical support portion 56A to the other end of the horizontal arm portion 56B which is attached to the operation panel 21 is greater than the distance D1.

Figure 39:
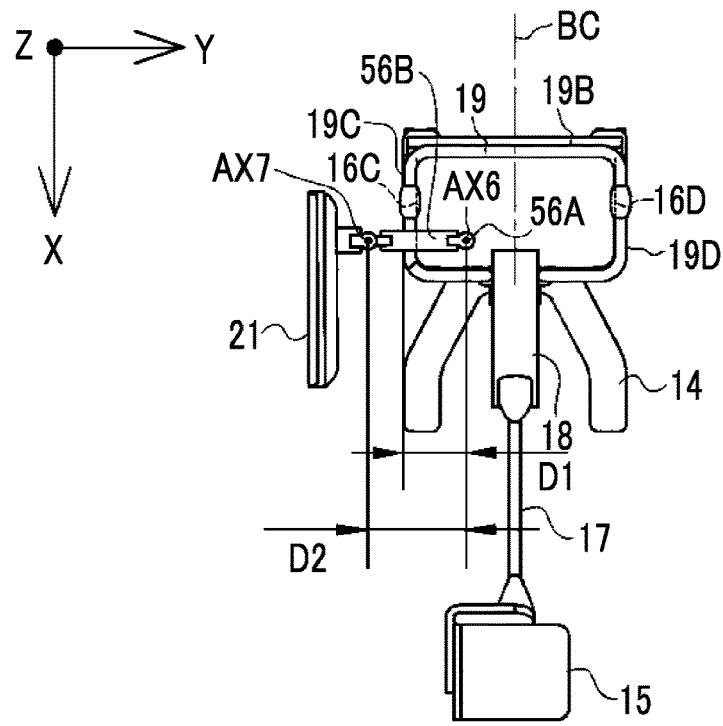
FIG. 39 is a second diagram illustrating the third embodiment.

At the initial position illustrated in FIG. 38, the horizontal arm portion 56B extends from the axis AX6 to the side bar portion 19D that is distant from the vertical support portion 56A. In this state, the horizontal arm portion 56B is accommodated inside the handle 19. In a case in which the horizontal arm portion 56B is rotated about the axis AX6 by 180° in the counterclockwise direction from the initial position, the horizontal arm portion 56B extends to the side bar portion 19C that is close to the vertical support portion 56A as illustrated in FIG. 39. Since the length D2 of the horizontal arm portion 56B is greater than the distance D1, the end portion of the horizontal arm portion 56B, to which the operation panel 21 is attached, protrudes outward from the handle 19. As described above, in a case in which the operation panel 21 protrudes outward from the handle 19, the handle 19 does not hinder an operation. Therefore, operability is high.

In addition, since the vertical support portion 56A is offset to one side bar portion 19C, the length D2 of the horizontal arm portion 56B required to protrude outward from the side bar portion 19C is short. Therefore, it is easy to accommodate the operation panel 21 inside the handle 19 with the operation surface 21A of the operation panel 21 facing backward as at the initial position.

The content of this configuration will be described in detail in comparison with a comparative example illustrated in FIGS. 40 and 41. The comparative example is the same as the above-described embodiments except that an attachment arm 156 is provided instead of the attachment arm 56. In the attachment arm 156, a vertical support portion 156A is provided at the center position BC of the main body unit 16 and is not offset to one side in the width direction. Therefore, as illustrated in FIG. 41, the length D2 of the horizontal arm portion 156B needs to be greater than that in the above-described embodiment illustrated in FIG. 39 in order to dispose the operation panel 21 so as to protrude outward from the handle 19 at the side position.

Figure 40:
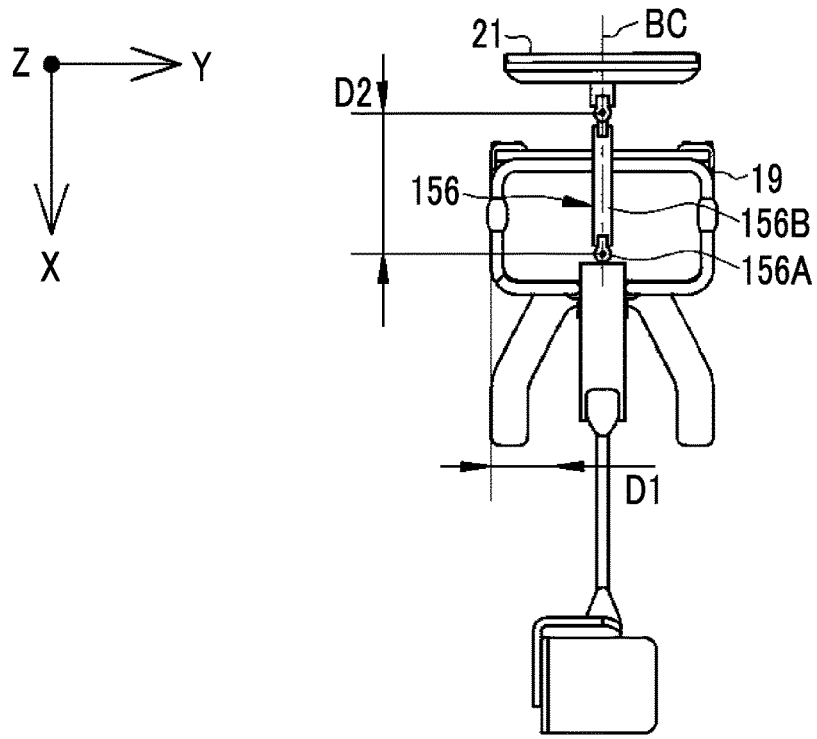
FIG. 40 is a first diagram illustrating a comparative example of the third embodiment.
Figure 41:
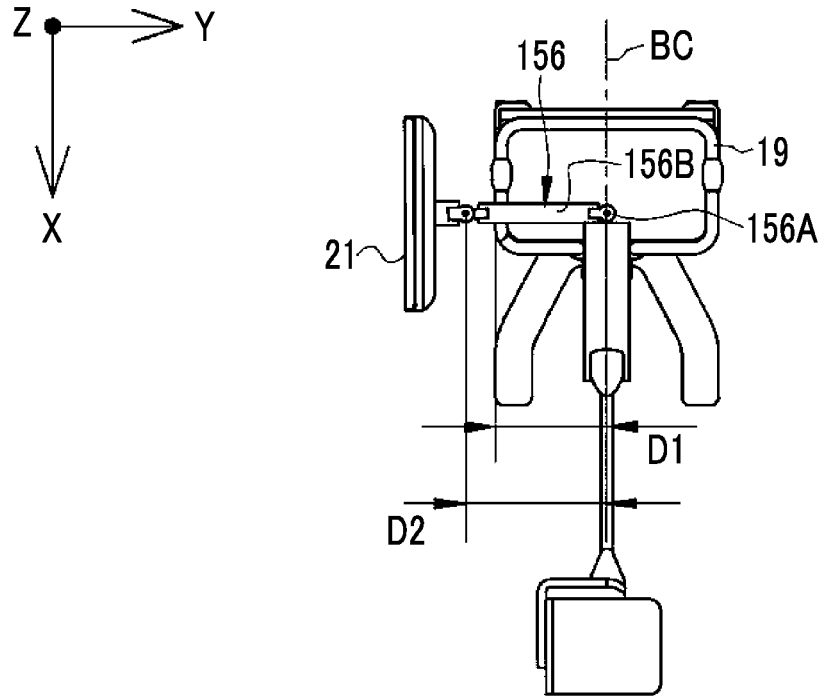
FIG. 41 is a second diagram illustrating the comparative example of the third embodiment.

However, in the above-mentioned configuration in which the length D2 is long, even in a case in which the operation panel 21 is located at the rear position as illustrated in FIG. 40, the operation panel 21 protrudes from the handle 19 and it is difficult to accommodate the operation panel 21 inside the handle 19. As described above, in a case in which the medical staff runs the treatment cart 11, the medical staff holds the handle 19 from the rear side. Therefore, in a case in which the operation panel 21 protrudes backward, it is difficult to hold the handle 19. For this reason, the configuration of the attachment arm 56 illustrated in FIGS. 38 and 39 is preferable.

This problem occurs particularly in a case in which the size of the main body unit 16 in the front-rear direction is reduced. The reason is that the operation panel 21 does not project backward if the main body unit 16 is not thin even in a case in which the attachment arm 156 illustrated in FIG. 40 is used. The cassette storage portion 28 is provided on the rear surface of the main body unit 16. The cassette storage portion 28 stores the electronic cassettes 12 in a posture in which the detection surfaces are parallel to each other. Therefore, the size of the main body unit 16 in the width direction needs to be equal to or larger than the size of the electronic cassette 12 in the width direction. In a case in which the size of the main body unit 16 is reduced, the thickness of the main body unit 16 in the front-rear direction is reduced, which causes the above-mentioned problem. Therefore, the third embodiment is particularly effective in a case in which the thin main body unit 16 having the cassette storage portion 28 provided on the rear surface 16B is provided.

Figure 42:
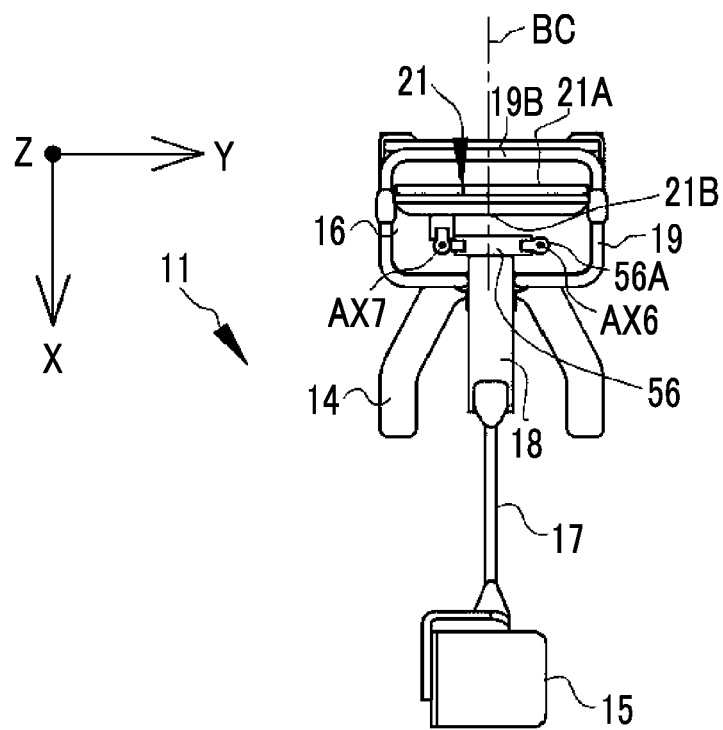
FIG. 42 is a first diagram illustrating a modification example of the third embodiment.

As illustrated in FIG. 42, the attachment position of the vertical support portion 56A may be movable. In FIG. 42, the attachment position of the vertical support portion 56A is on the right side as viewed from the front side and is offset to the side opposite to the position illustrated in FIG. 38. As such, in a case in which the attachment position of the vertical support portion 56A is movable between a position close to one side bar portion 19C and a position close to the other side bar portion 19D, flexibility in changing the position and/or direction of the operation panel 21 increases.

Figure 43:
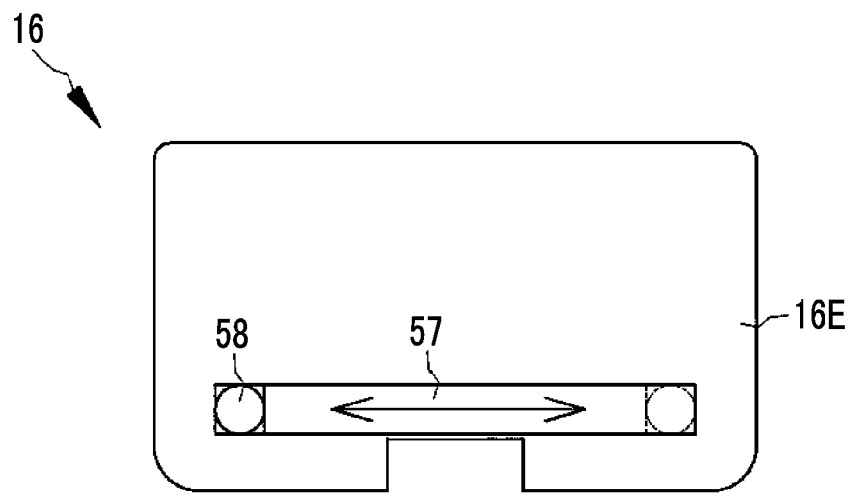
FIG. 43 is a second diagram illustrating the modification example of the third embodiment.
Figure 44:
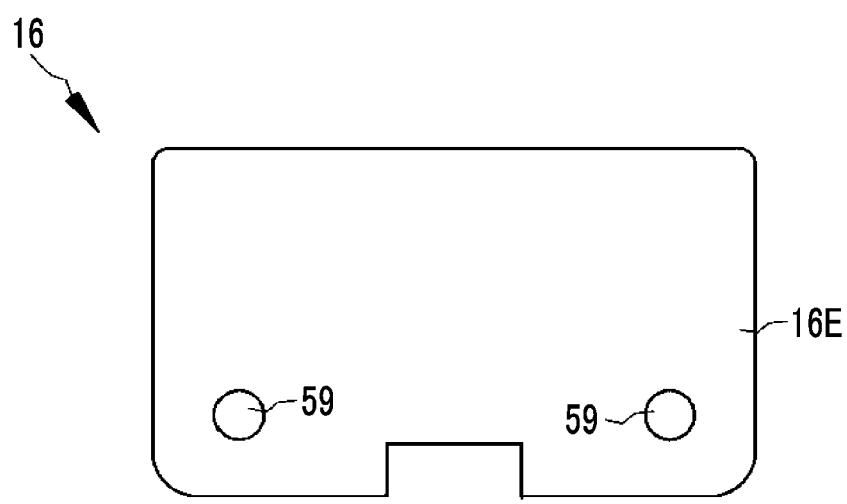
FIG. 44 is a third diagram illustrating the modification example of the third embodiment.

As illustrated in FIG. 43, a slide groove 57 is formed in the upper surface 16E of the main body unit 16 in the width direction. A mount 58 to which the base end of the vertical support portion 56A is attached is provided in the slide groove 57 so as to be movable in the width direction. The mount 58 can be moved to any position in the slide groove 57. As illustrated in FIG. 44, two attachment holes 59 for the vertical support portion 56A may be provided in the upper surface 16E of the main body unit 16 and the attachment position may be changed by any one of the two attachment holes 59. The aspects in which the attachment position of the vertical support portion 56A is movable include the two aspects illustrated in FIGS. 43 and 44.

Fourth Embodiment

A fourth embodiment relates to the function and shape of an operation panel 21. The basic configuration of each portion of a treatment cart 11 is the same as that in the first embodiment. The same parts and members are denoted by the same reference numerals and the description thereof will not be repeated.

Figure 45:
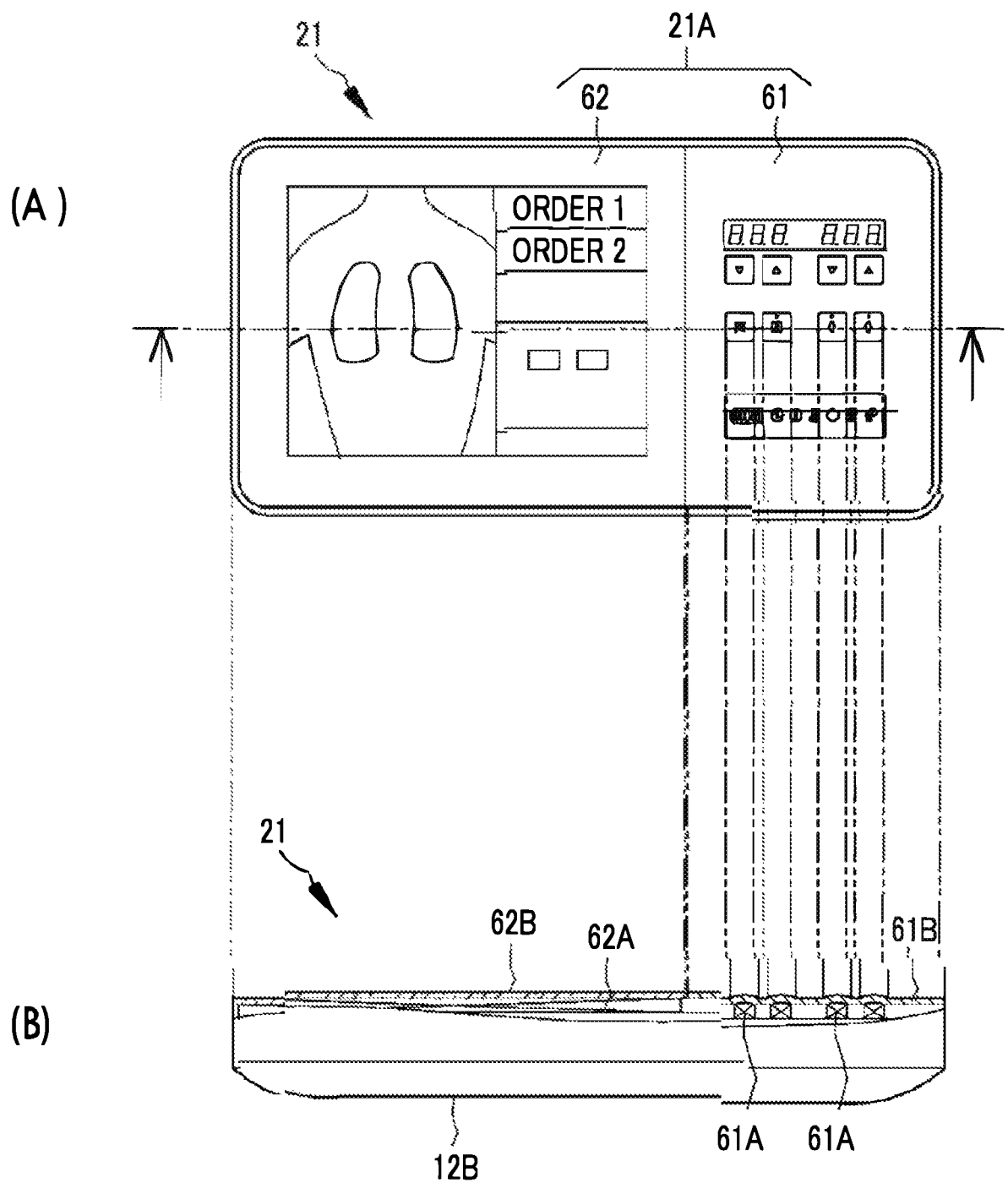
FIG. 45 is a configuration diagram illustrating an operation panel according to a fourth embodiment.

As illustrated in FIG. 45, in the operation panel 21, a first operation unit 61 and a second operation unit 62 are provided on an operation surface 21A. The first operation unit 61 is an operation unit for operating the X-ray emitting unit 15. The second operation unit 62 is an operation unit for operating the electronic cassette 12 and functions as an image display unit which displays the X-ray image detected by the electronic cassette 12.

The first operation unit 61 includes mechanical switches. As illustrated in (B) of FIG. 45, the first operation unit 61 includes a plurality of switches 61A forming the mechanical switches. The plurality of switches 61A are covered by one sheet 61B covering the entire region of the first operation unit 61. Therefore, in the operation surface 21A, there are no grooves and/or holes formed between the plurality of switches 61A in the surface of the first operation unit 61.

The second operation unit 62 includes a touch panel 62A. The touch panel 62A is covered by a sheet 62B covering the entire region of the second operation unit 62. As such, the entire surface of the first operation unit 61 is covered by one sheet 61B and the entire surface of the second operation unit 62 is covered by one sheet 62B. In addition, the heights of the surfaces of the sheets 61B and 62B are substantially equal to each other. Here, the term "substantially equal" allows a level difference of a few millimeters. As such, since the operation surface 21A has almost no level difference, it is easy to perform, for example, cleaning and sweeping and to maintain the hygiene of the operation panel 21 at a high level.

Fifth Embodiment

A fifth embodiment illustrated in FIGS. 46 to 49 relates to the form of a support 18. The basic configuration of each portion of a treatment cart 11 is the same as that in the first embodiment. The same parts and members are denoted by the same reference numerals and the description thereof will not be repeated.

Figure 46:
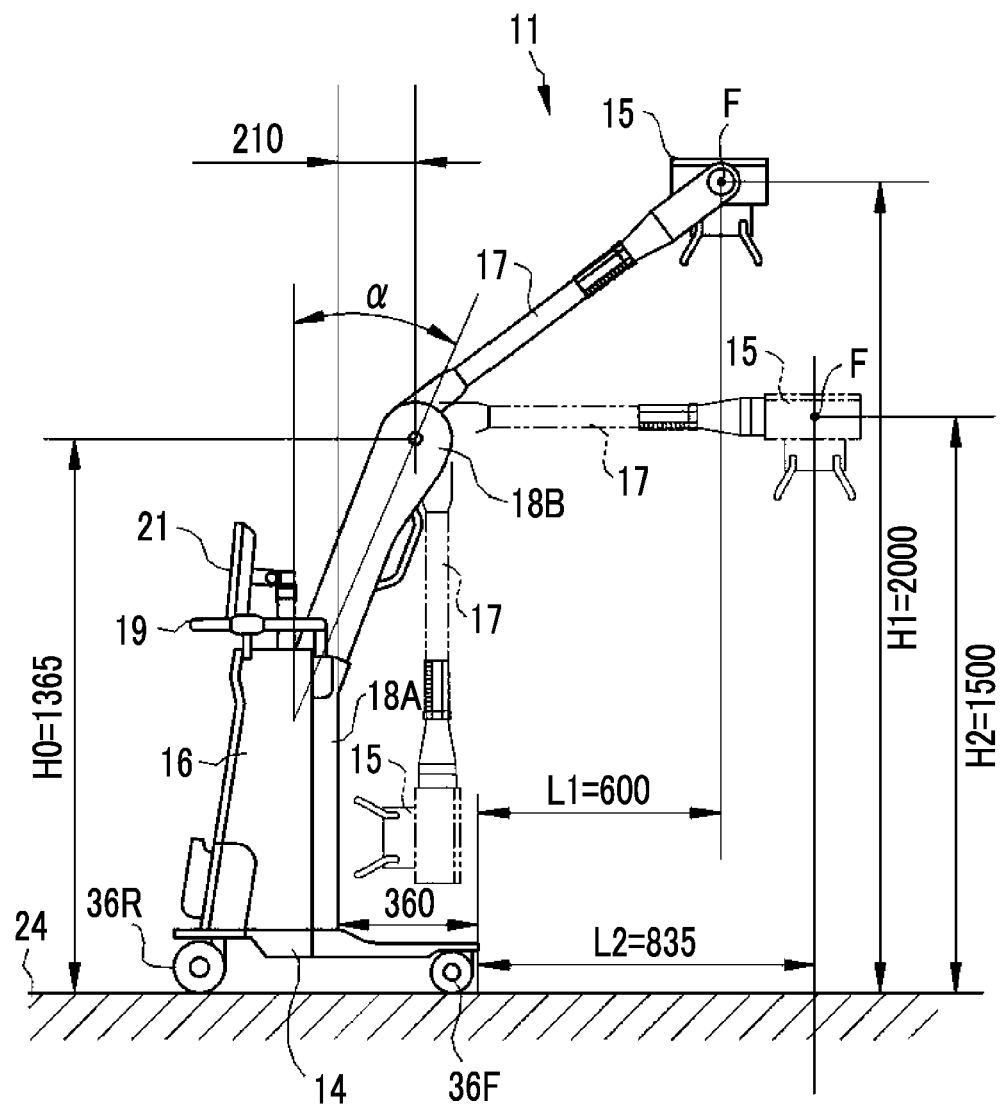
FIG. 46 is a first diagram illustrating a fifth embodiment.

As illustrated in FIG. 46, in the support 18, a second support portion 18B which is a portion of an upper part of the support 18 is inclined forward by an angle α. The angle (inclination angle) a is the angle of the longitudinal axis of the second support portion 18B with respect to the vertical direction. The upper end of the second support portion 18B supports the arm unit 17 such that the arm unit 17 is rotatable about the rotation axis AX2. The second support portion 18B rotates about the rotation axis AX1 that extends in the Z-axis direction with respect to the carriage unit 14 and does not rotate about an axis parallel to the rotation axis AX2 of the arm unit 17. The forward inclination angle α of the second support portion 18B is fixed. Since the second support portion 18B is inclined forward, it is possible to extend the range of the X-ray emitting unit 15 in the horizontal direction without complicating the structure of the arm unit 17.

As a method for extending the range of the X-ray emitting unit 15 in the horizontal direction, there is a method in which the arm unit is formed in a telescopic structure in which it can be expanded and contracted in the longitudinal axis direction. However, in a case in which the arm unit is formed in the telescopic structure, the structure of the arm unit becomes complicated. The arm unit 17 does not have the telescopic structure and the length of the arm unit 17 in the longitudinal axis direction is fixed. Therefore, the second support portion 18B supporting the base end of the arm unit 17 is inclined forward to extend the range of the X-ray emitting unit 15 in the horizontal direction.

Figure 47:
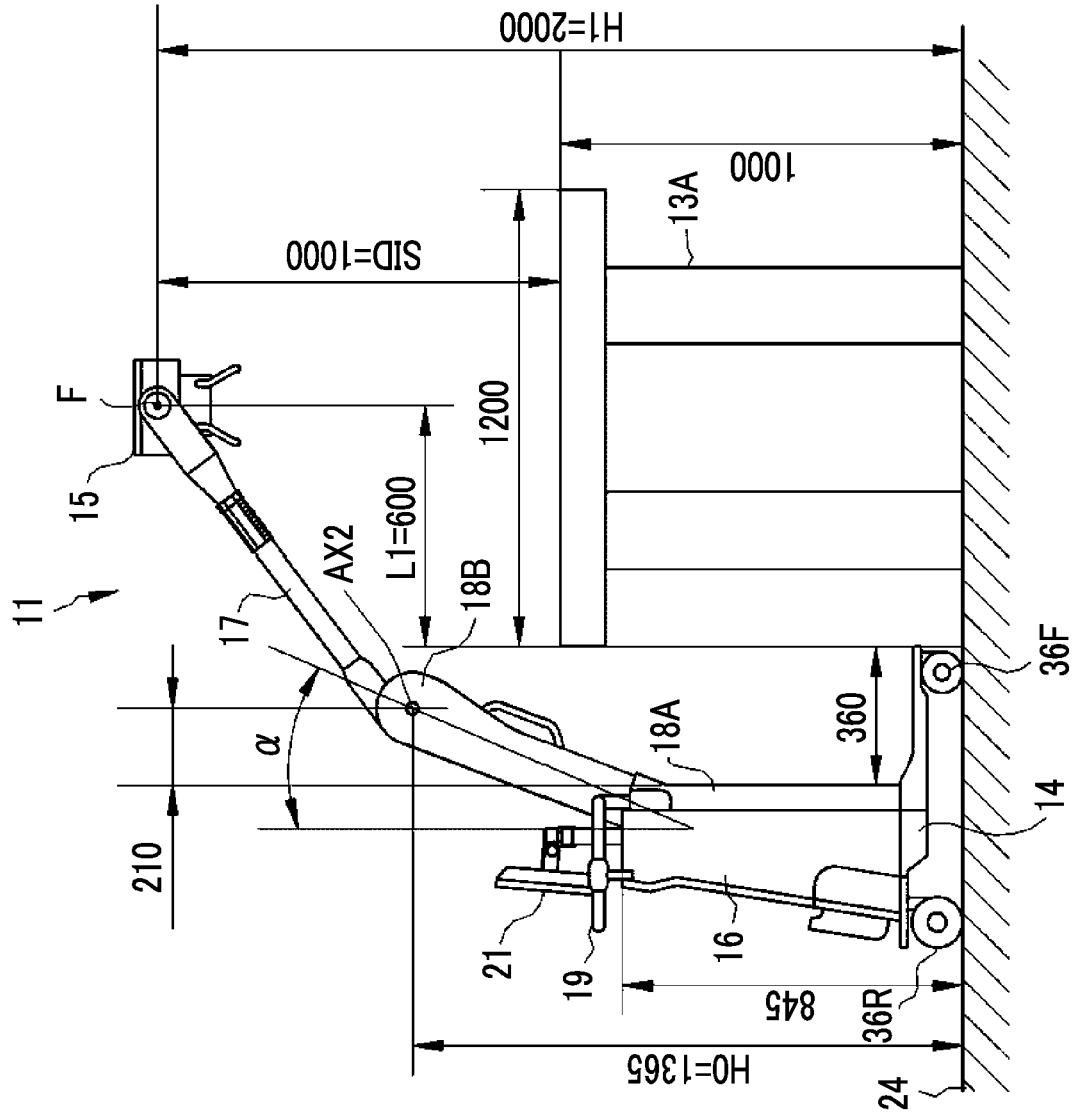
FIG. 47 is a second diagram illustrating the fifth embodiment.
Figure 48:
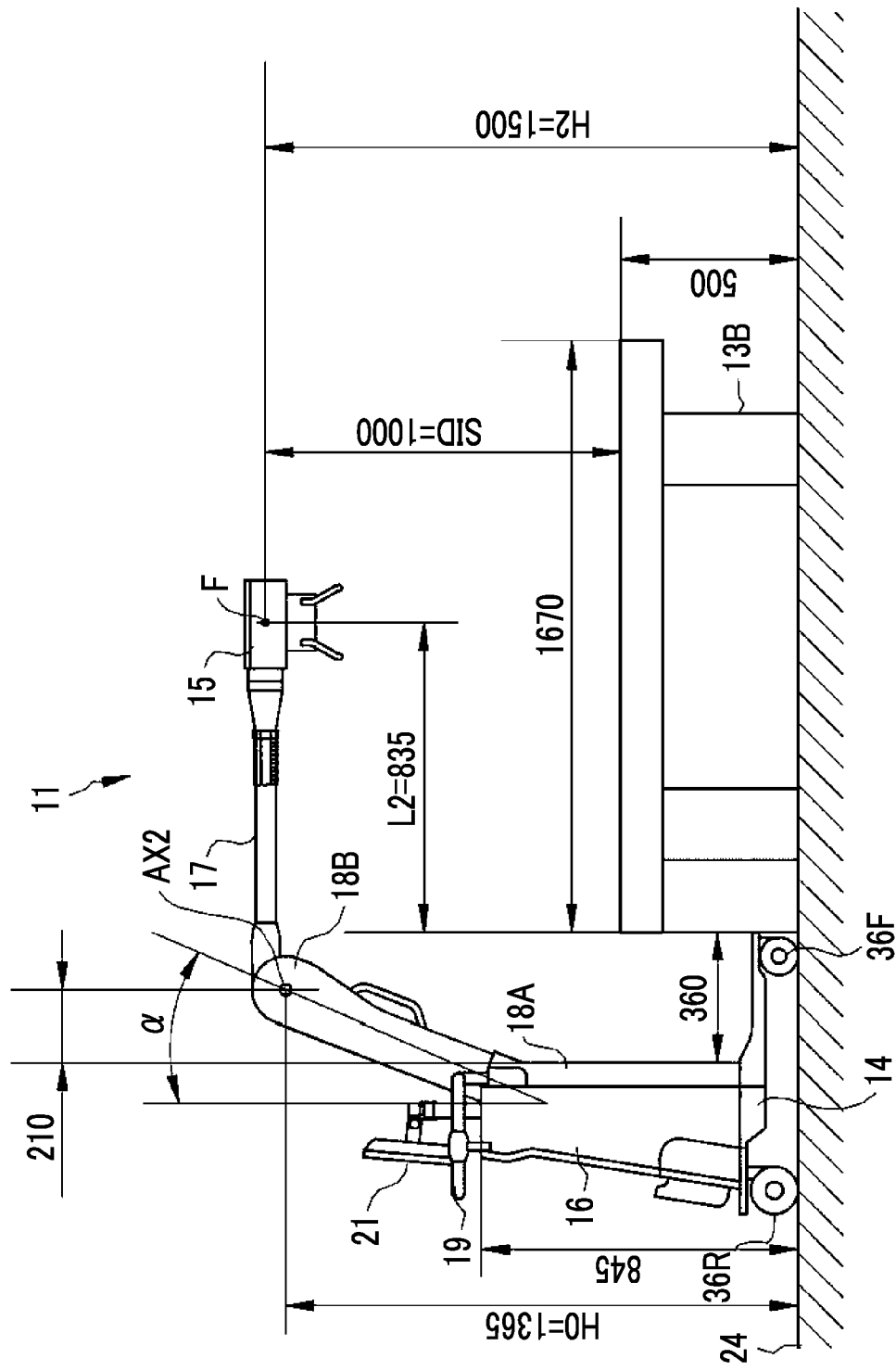
FIG. 48 is a third diagram illustrating the fifth embodiment.

As illustrated in FIGS. 47 and 48, the detailed dimensions of each portion of the treatment cart 11 are set so as to correspond to the sizes of a plurality of beds 13A and 13B. The bed 13A illustrated in FIG. 47 is a bed provided in an operating room. The bed 13A in the operating room includes a top plate that is relatively high and has a relatively small width, considering the workability of the medical staff who stands up and faces the patient on the bed 13A for a long time. For example, the size of the bed 13A is a height of 1000 mm and a width of about 1200 mm.

In contrast, the bed 13B illustrated in FIG. 48 is a bed provided in a hospital room. The bed 13B in the hospital room includes a top plate that is relatively low and has a relatively large width, considering the patient's convenience in getting on and off the bed or comfortableness. For example, the size of the bed 13B is a width of 1670 mm and a height of about 500 mm.

In a case in which any bed 13 is used, it is preferable that the X-ray emitting unit 15 reaches a center position of the top plate of the bed 13 in the horizontal direction. In addition, in a case in which any bed 13 is used, it is preferable to ensure about 1000 mm as a source to image receptor distance (SID) which is a distance from an X-ray focus F of the X-ray emitting unit 15 to the electronic cassette 12 that is placed on the bed 13 and faces the X-ray emitting unit 15.

A height H0 from the placement surface 24 to the rotation axis AX2 of the arm unit 17 located at the upper end portion of the support 18 is, for example, about 1365 mm considering the above-mentioned conditions. In addition, the angle α is about 23° and the distance from the front surface of the first support portion 18A located at the forefront of the main body unit 16 to the rotation axis AX2 of the base end of the arm unit 17 is about 210 mm.

As illustrated in FIG. 47, in a posture in which the arm unit 17 is rotated to the upper end position such that the range of the X-ray emitting unit 15 in the vertical direction is the maximum, the height H1 of the X-ray focus F from the placement surface 24 is about 2000 mm. Therefore, in the case of the bed 13A having a height of about 1000 mm, it is possible to ensure an SID of about 1000 mm. The range of the X-ray emitting unit 15 in the horizontal direction in this posture is a distance L1 from the leading end position of the carriage unit 14 to the X-ray focus F and is about 600 mm. Since the width of the bed 13A is about 1200 mm, the X-ray focus F of the X-ray emitting unit 15 can reach the substantially center position of the bed 13A in the width direction.

In this embodiment, the length of a protruding portion of the leading end of the carriage unit 14, that is, the distance from the front surface of the support 18 at the leading end of the main body unit 16 to the leading end position of the carriage unit 14 is about 360 mm. Therefore, in a case in which this portion can get into a clearance space below the top plate of the bed 13A, the main body unit 16 can be brought closer to a side end portion of the bed 13A. As a result, the range of the X-ray focus F in the horizontal direction is further extended.

As illustrated in FIG. 48, in a posture in which the longitudinal axis of the arm unit 17 is horizontal such that the range of the X-ray emitting unit 15 in the horizontal direction is the maximum, the height H2 of the X-ray focus F from the placement surface 24 is about 1500 mm. Therefore, in the case of the bed 13B having a height of about 500 mm, it is possible to ensure an SID of about 1000 mm. The range of the X-ray emitting unit 15 in the horizontal direction in this posture is a distance L2 from the leading end position of the carriage unit 14 to the X-ray focus F and is about 835 mm. Since the width of the bed 13B is about 1670 mm, the X-ray focus F of the X-ray emitting unit 15 can reach the substantially center position of the bed 13B in the width direction.

As in the case in which the bed 13A illustrated in FIG. 47 is used, in a case in which the protruding portion of the leading end of the carriage unit 14 can get into a clearance space below the top plate of the bed 13B, the main body unit 16 can be brought closer to a side end portion of the bed 13B. As a result, the range of the X-ray focus F in the horizontal direction is further extended.

Figure 49:
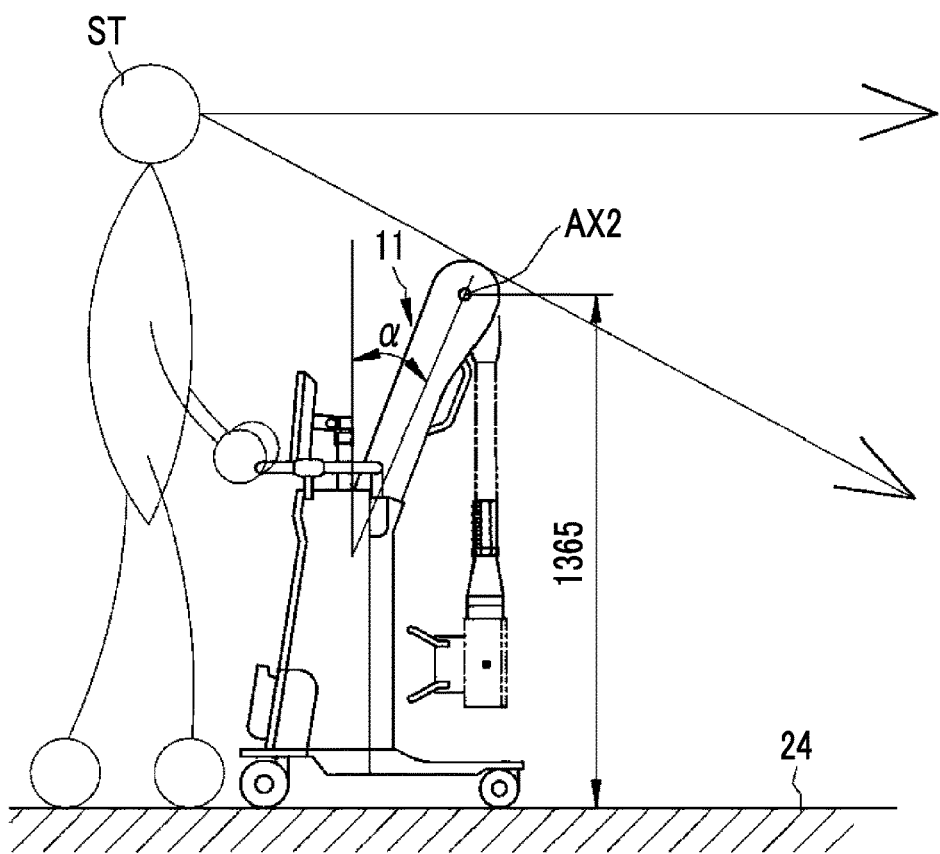
FIG. 49 is a fourth diagram illustrating the fifth embodiment.

As such, in a case in which the second support portion 18B provided in the upper part of the support 18 is inclined forward, the overall height of the treatment cart 11 with the arm unit 17 located at the storage position can be less than that in a case in which the second support portion 18B is not inclined. Therefore, as illustrated in FIG. 49, in a case in which the medical staff ST pushes the treatment cart 11 from the rear side to run the treatment cart 11, it is possible to ensure a good front view.

Sixth Embodiment

A sixth embodiment illustrated in FIGS. 50 to 54 relates to a cassette locking mechanism for preventing the theft of the electronic cassette 12. The basic configuration of each portion of a treatment cart 11 is the same as that in the first embodiment. The same parts and members are denoted by the same reference numerals and the description thereof will not be repeated.

Figure 50:
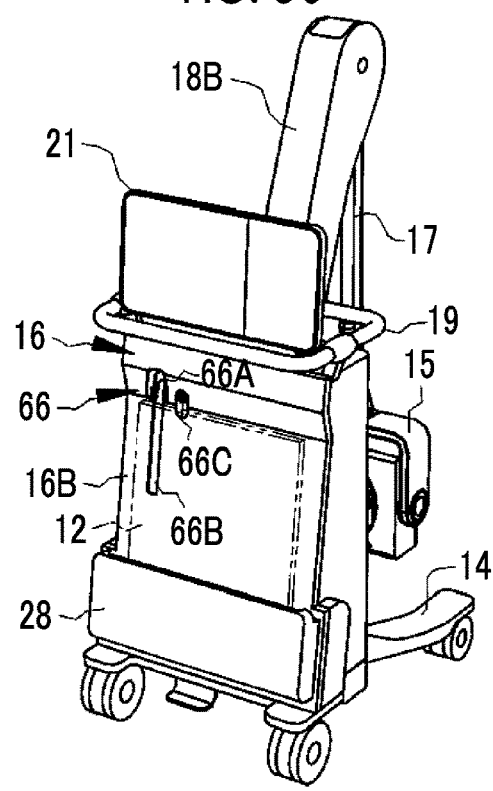
FIG. 50 is a first diagram illustrating a sixth embodiment.

As illustrated in FIG. 50, in the treatment cart 11, a cassette fixing mechanism (corresponding to a fixing mechanism) 66 that fixes the electronic cassette 12 stored in the cassette storage portion 28 is provided on the rear surface 16B of the main body unit 16. The cassette fixing mechanism 66 fixes the electronic cassette 12 such that the electronic cassette 12 stored in the cassette storage portion 28 does not carelessly lose its position and or posture. For example, a little vibration is generated while the treatment cart 11 is traveling. The use of the cassette fixing mechanism 66 makes it possible to prevent the electronic cassette 12 from losing its position and/or posture in the cassette storage portion 28 even in a case in which the carriage unit 14 vibrates. In addition, since the electronic cassette 12 is fixed, it is possible to prevent poor connection between the electronic cassette 12 and the charging connector 31.

The cassette fixing mechanism 66 includes a slide groove 66A that extends in the vertical direction in the rear surface 16B, a fixing portion 66B that is slidably fixed to the slide groove 66A, and a key lock 66C that locks the sliding of the fixing portion 66B with a key. The fixing portion 66B is provided above the cassette storage portion 28 in the vertical direction at a position that faces the cassette storage portion 28 located below the fixing portion 66B. For example, the fixing portion 66B has an inverted J-shape in a cross-sectional view. The fixing portion 66B comes into contact with an upper end portion of the electronic cassette 12 having a lower end portion stored in the cassette storage portion 28 and fixes the electronic cassette 12 such that the electronic cassette 12 is interposed between the fixing portion 66B and the cassette storage portion 28.

The key lock 66C locks the position of the fixing portion 66B at any position in the slide groove 66A. The use of the key lock 66C makes it possible to prevent the theft of the electronic cassette 12.

The fixing portion 66B is moved in the slide groove 66A and is movable in a direction in which the gap between the fixing portion 66B and the cassette storage portion 28 changes. Therefore, the cassette fixing mechanism 66 can fix the electronic cassettes 12 with a plurality of sizes, such as the electronic cassette 12A with a size of 17 inches×17 inches and/or the electronic cassette 12B with a size of 12 inches×10 inches.

As described in FIG. 13, the position of the charging connector 31 in the width direction in the rear surface 16B is offset from the center position in order that the charging connector 31 corresponds to the electronic cassettes 12A and 12B with different sizes. Since the electronic cassettes 12A and 12B are stored so as to lean to the charging connector 31 of the cassette storage portion 28, the position of the cassette fixing mechanism 66 in the width direction is offset from the center position.

Figure 51:
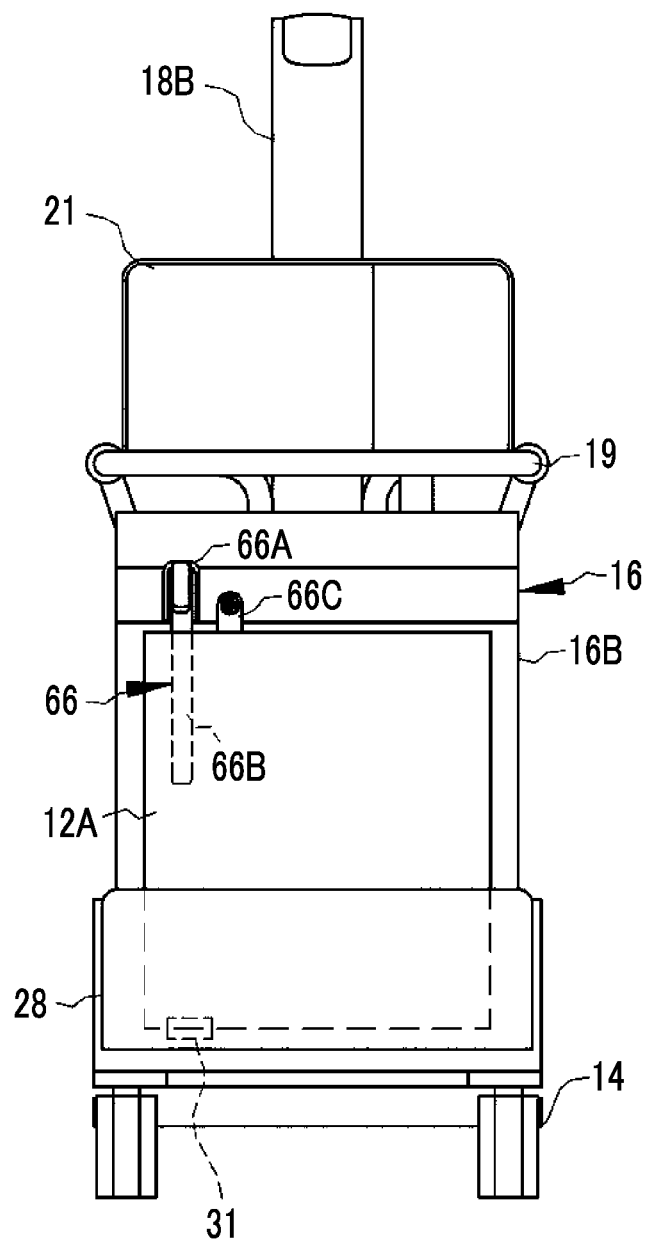
FIG. 51 is a second diagram illustrating the sixth embodiment.
Figure 52:
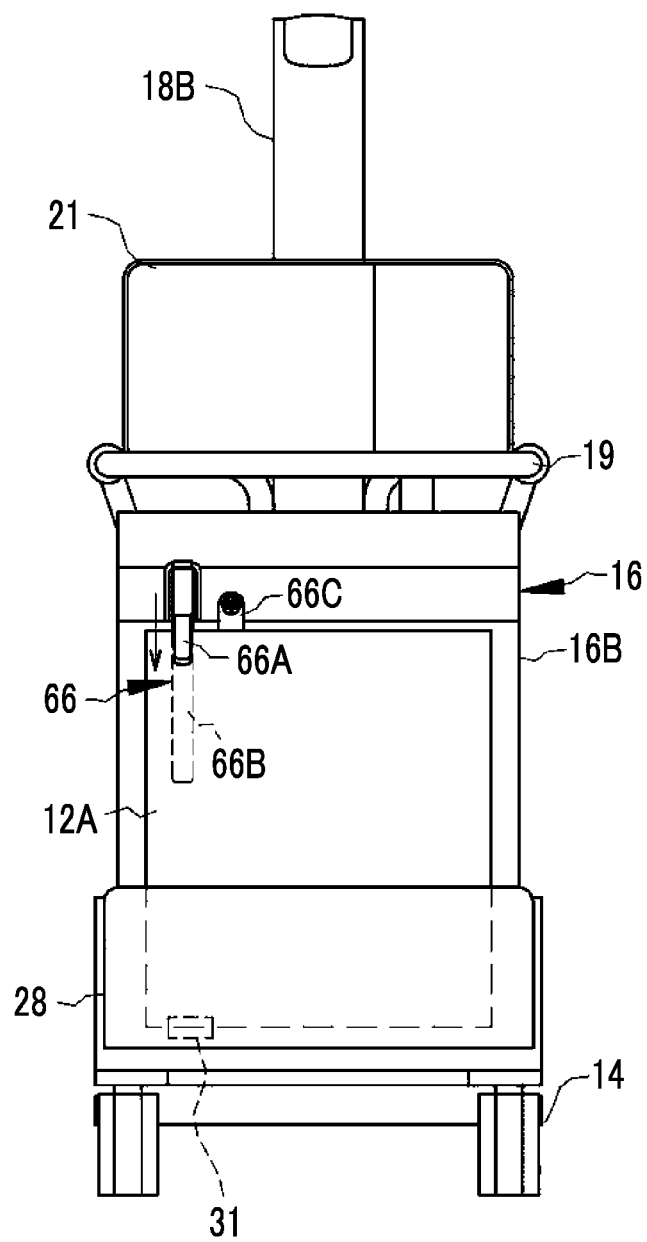
FIG. 52 is a third diagram illustrating the sixth embodiment.
Figure 53:
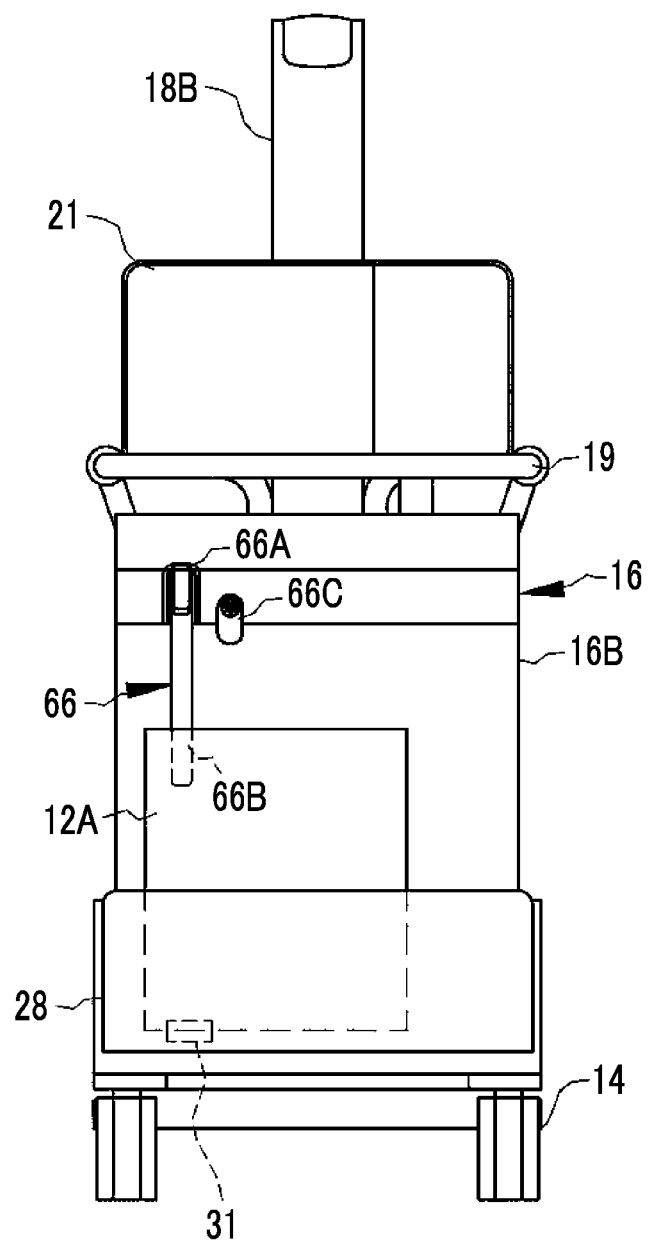
FIG. 53 is a fourth diagram illustrating the sixth embodiment.
Figure 54:
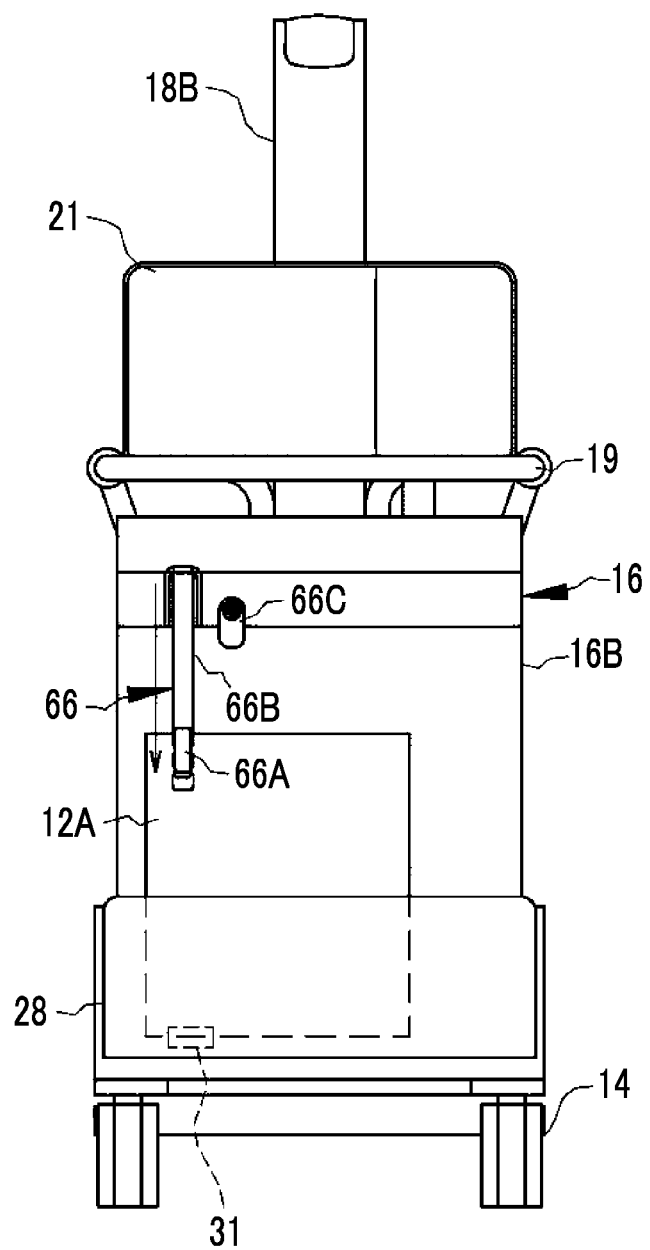
FIG. 54 is a fifth diagram illustrating the sixth embodiment.

FIGS. 51 and 52 illustrate an example of the fixation of the electronic cassette 12A. FIG. 51 illustrates a case in which the fixing portion 66B is at an initial position and FIG. 52 illustrates a state in which the fixing portion 66B is slid to the position where it comes into contact with the upper end of the electronic cassette 12A. FIGS. 53 and 54 illustrate an example of the fixation of the small electronic cassette 12B. FIG. 53 illustrates a case in which the fixing portion 66B is at the initial position and FIG. 54 illustrates a state in which the fixing portion 66B is slid to the position where it comes into contact with the upper end of the electronic cassette 12B. As such, the cassette fixing mechanism 66 can fix the electronic cassettes 12A and 12B with a plurality of sizes.

Seventh Embodiment

Figure 55:
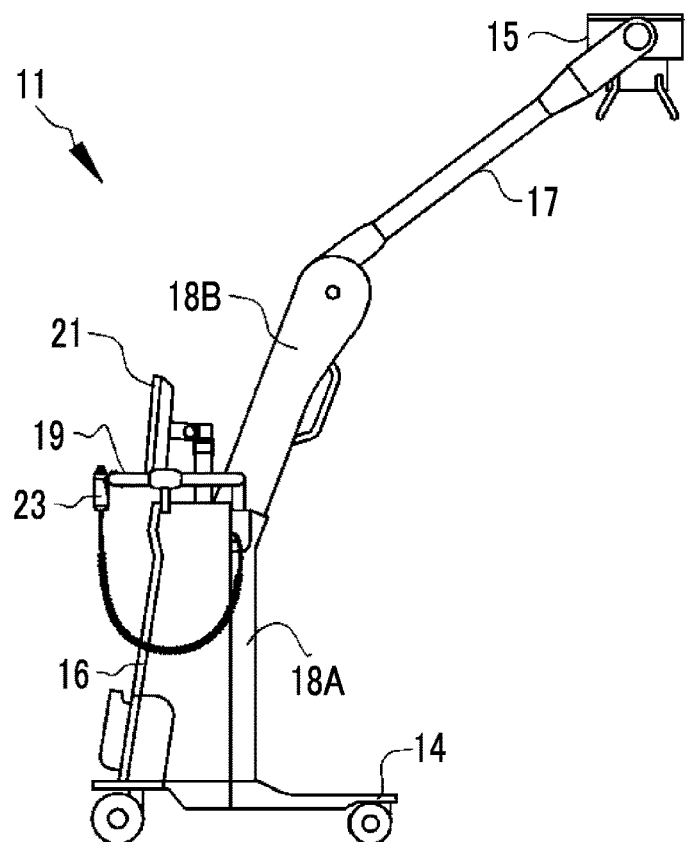
FIG. 55 is a first diagram illustrating a seventh embodiment.
Figure 56:
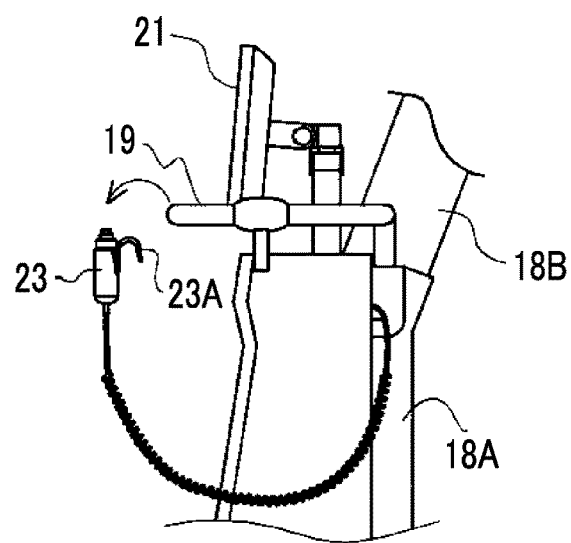
FIG. 56 is a second diagram illustrating the seventh embodiment.

A seventh embodiment illustrated in FIGS. 55 and 56 relates to the form of an irradiation switch 23. The configuration of each portion of a treatment cart 11 is the same as that in the first embodiment. The same parts and members are denoted by the same reference numerals and the description thereof will not be repeated.

As illustrated in FIG. 56, the irradiation switch 23 is provided with a hook 23A. The provision of the hook 23A makes it possible to hang the irradiation switch 23 on the handle 19 as illustrated in FIG. 55. The handle 19 is a bar handle that extends in the horizontal direction and is provided substantially in the entire periphery of the support 18. Since the hook 23A is provided in the irradiation switch 23, it is possible to dispose the irradiation switch 23 at any position around the support 18 where the handle 19 is provided.

Eighth Embodiment

Figure 57:
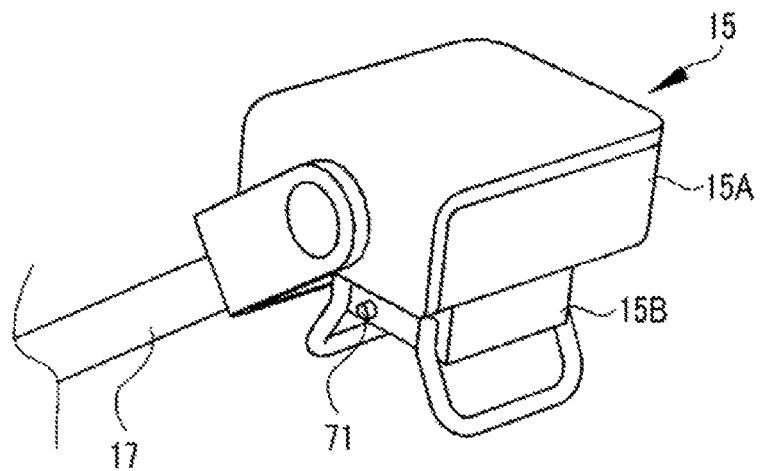
FIG. 57 is a first diagram illustrating an eighth embodiment.
Figure 58:
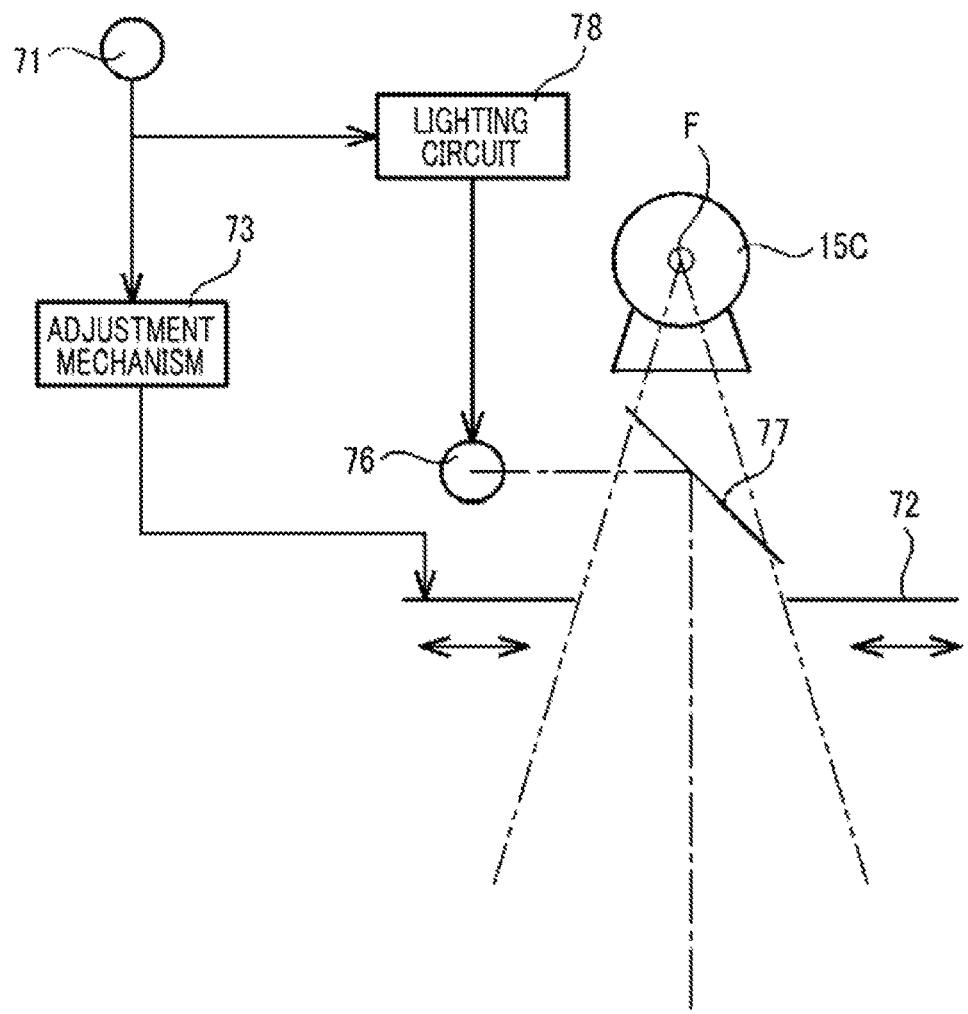
FIG. 58 is a second diagram illustrating the eighth embodiment.

An eighth embodiment illustrated in FIGS. 57 and 58 relates to the function of an adjustment knob 71 of an irradiation field limiter 15B of an X-ray emitting unit 15. The configuration of each portion of a treatment cart 11 is the same as that in the first embodiment. The same parts and members are denoted by the same reference numerals and the description thereof will not be repeated.

As illustrated in FIG. 57, the adjustment knob 71 is provided on an outer peripheral surface of a housing of the irradiation field limiter 15B. As illustrated in FIG. 58, the irradiation field limiter 15B includes, for example, a plurality of shielding plates 72 that shield X-rays and an adjustment mechanism 73 that moves the position of the shielding plates 72 to adjust the size of an emission opening. The irradiation field limiter 15B includes a lamp 76 that emits visible light for checking the position of an irradiation field, a lighting circuit 78 that turns on the lamp 76, and a reflective mirror 77 that reflects the visible light.

The reflective mirror 77 is provided on an X-ray emission path, is inclined at an angle of 45° with respect to the lamp 76 and the optical axis of each X-ray, and emits visible light through the emission opening. The irradiation field of the visible light is checked to check the irradiation field of X-rays before X-ray imaging. The medical staff operates the adjustment knob 71 to change the size of the emission opening while checking the irradiation field of the visible light. The adjustment knob 71 is connected to the lighting circuit 78 in addition to the adjustment mechanism 73. In a case in which the adjustment knob 71 is operated, the lighting circuit 78 operates to turn on the lamp 76. Since it is not necessary to operate a lamp lighting switch in addition to the adjustment knob 71, operability is high.

In each of the above-described embodiments, the X-ray emitting unit 15 is used in combination with the electronic cassette. However, the X-ray emitting unit 15 may be used in combination with a film cassette using an X-ray film as an image recording medium, instead of the electronic cassette.

Each of the above-described embodiments can be applied to a radiation emitter that emits radiation, such as y-rays, other than X-rays. In addition, the invention is not limited to the above-described embodiments and can be appropriately changed without departing from the scope and spirit of the invention. For example, the inventions and/or the embodiments can be combined with each other. The combinations of the inventions and/or the embodiments include a combination of a portion of or the entire content of one invention and a portion of or the entire content of another invention.

In addition to the invention described in the claims, the invention described in the following supplementary notes can be understood from the above description.

"First Supplementary Note" (Related to Third Embodiment)

[First Supplementary Note 1]

There is provided a mobile radiation generation apparatus comprising: a carriage unit that includes a front wheel and a rear wheel and is capable of traveling; a support that vertically stands on the carriage unit, supports an arm unit to which a radiation emitting unit is attached, and is provided between the front wheel and the rear wheel in a front-rear direction of the carriage unit; a main body unit that is mounted on the carriage unit, is provided so as to protrude backward from the support, and has a front surface facing the front wheel, a rear surface facing the rear wheel, first and second side surfaces connecting the front surface and the rear surface, and an upper surface located on an upper side in a vertical direction; a handle that is provided behind the support and above the main body unit and includes a rear bar portion which is located on a rear surface side of the main body unit and extends in a width direction perpendicular to a front-rear direction of the main body unit and first and second side bar portions which are located close to the first and second side surfaces, respectively, and extend in the front-rear direction of the main body unit; an operation panel having an operation surface on which an operation unit is provided; a vertical support portion that is provided on the upper surface of the main body unit, supports the operation panel so as to be rotatable about a rotation axis extending in the vertical direction, and is located at a position closer to the second side bar portion than to the first side bar portion; and a horizontal arm portion that has one end attached to the vertical support portion and the other end attached to the operation panel and extends from the vertical support portion in a horizontal direction perpendicular to the rotation axis. A length of the horizontal arm portion from the one end to the other end is greater than a distance between the vertical support portion and the second side bar portion.

[First Supplementary Note 2]

In the mobile radiation generation apparatus according to First Supplementary Note 1, the operation panel is accommodated inside the handle at an initial position where a longitudinal axis of the horizontal arm portion is parallel to the width direction of the main body unit and the operation surface of the operation panel faces backward in parallel to the width direction.

[First Supplementary Note 3]

In the mobile radiation generation apparatus according to First Supplementary Note 2, the vertical support is provided so as to be movable between a position close to the second side bar portion and a position close to the first side bar portion.

[First Supplementary Note 4]

The mobile radiation generation apparatus according to any one of First Supplementary Notes 1 to 3 further comprises a storage portion that is provided on the rear surface and stores a radiographic image detector having a detection surface which is flat and has a rectangular shape in a plan view such that the detection surface is parallel to the rear surface.

"Second Supplementary Note" (Related to Fifth Embodiment)

[Second Supplementary Note 1]

There is provided a mobile radiation generation apparatus comprising: a carriage unit that includes a front wheel and a rear wheel; an arm unit having a free end to which a radiation emitting unit is attached; and a support portion that vertically stands on the carriage unit and has an upper end portion which supports a base end of the arm unit such that the arm unit is rotatable about a rotation axis parallel to a width direction perpendicular to a front-rear direction of the carriage unit. A part of the support portion which includes the upper end portion is inclined toward a front side of the carriage unit and an inclination angle is fixed.

[Second Supplementary Note 2]

In the mobile radiation generation apparatus according to Second Supplementary Note 1, a length of the arm unit in a longitudinal axis direction is fixed.

[Second Supplementary Note 3]

In the mobile radiation generation apparatus according to Second Supplementary Note 2, the arm unit rotates about the rotation axis and the X-ray emitting unit is moved to a storage position that is below the upper end portion of the support portion.

"Third Supplementary Note" (Related to Unlocking Operation Portion of Arm Unit)

[Third Supplementary Note 1]

There is provided a mobile radiation generation apparatus comprising: a carriage unit; a support portion that stands on the carriage unit in a vertical direction; an arm unit that has a free end attached to a radiation emitting unit and a base end supported by an upper end portion of the support portion in the vertical direction, is rotatable about a rotation axis parallel to a width direction perpendicular to a front-rear direction of the carriage unit, and is moved to a storage position where the radiation emitting unit is located below the upper end portion in the vertical direction; and an unlocking operation portion that unlocks the movement of the arm unit at the storage position, is provided in a root portion of the arm unit attached to the radiation emitting unit, is slidable along a longitudinal axis of the arm unit, and is slid to a base end of the arm unit in a case in which the arm unit is at the storage position.

[Third Supplementary Note 2]

In the mobile radiation generation apparatus according to Third Supplementary Note 1, the arm unit is stopped at any position around the rotation axis by frictional force.

[Third Supplementary Note 3]

In the mobile radiation generation apparatus according to Third Supplementary Note 2, the movement of the arm unit is automatically locked in a case in which the arm unit is developed upward from the storage position and is then moved to the storage position again.

"Fourth Supplementary Note" (Related to Cassette Fixing Mechanism)

[Fourth Supplementary Note 1]

There is provided a mobile radiation generation apparatus comprising: a carriage unit; a support portion that stands on the carriage unit in a vertical direction; an arm unit having a free end attached to a radiation emitting unit and a base end supported by the support portion; a main body unit that is mounted on the carriage unit; a storage portion that is provided on a rear surface of the main body unit and stores at least a portion of a radiographic image detector; and a fixing mechanism that fixes the radiographic image detector stored in the storage portion. The fixing mechanism includes a fixing portion that is provided at a position which is above the storage portion in the vertical direction and faces the storage portion and comes into contact with an upper end portion of the radiographic image detector having a lower end portion stored in the storage portion to fix the radiographic image detector. The fixing portion is movable in a direction in which a gap between the fixing portion and the storage portion changes.

[Fourth Supplementary Note 2]

In the mobile radiation generation apparatus according to Fourth Supplementary Note 1, the fixing portion is slidable in the vertical direction.

[Fourth Supplementary Note 3]

In the mobile radiation generation apparatus according to Fourth Supplementary Note 2, a charging connector that charges the radiographic image detector is provided at a position that is offset from a center position of the main body unit in a width direction in the storage portion. The position of the fixing portion in the width direction is offset to a position corresponding to the charging connector.

EXPLANATION OF REFERENCES

2: X-ray imaging system
11: treatment cart (mobile radiation generation apparatus)
12, 12A, 12B, 12C: electronic cassette
13, 13A, 13B: bed
14: carriage unit
14A: frame
15: X-ray emitting unit
15A: radiation source unit
15B: irradiation field limiter
15C: X-ray tube
16: main body unit
16A: front surface
16B: rear surface
16C: side surface
16D: side surface
16E: upper surface
17: arm unit
18: support
18A: first support portion
18B: second support portion
18C: grip portion
19: handle
19A: front bar portion
19B: rear bar portion
19C: side bar portion
19D: side bar portion
21: operation panel
21A: operation surface
21B: rear surface
23: irradiation switch
23A: hook
24: placement surface
26: unlocking operation portion
28: cassette storage portion
29: bag
31: charging connector
36F: front wheel
36R: rear wheel
38: front pedal
39: rear pedal
41: two-wheel operative association mechanism
41A: two-wheel connection rod
41B: supporting metal part
42: front and rear pedal operative association mechanism
42A: front and rear operative association rod
42B: leading end portion
42C: rear end portion
43: supporting metal part
44: caster frame
44A: main body portion
46: wheel portion
47: supporting portion
48: cover metal part
49: spacer
51: rotating body
52: brake lever
53: push rod
54: gear
55: cam
56: attachment arm
56A: vertical support portion
56B: horizontal arm portion
56C: attachment portion
57: slide groove
58: mount
59: hole
61: first operation unit
61A: switch
61B: sheet 62: second operation unit
62A: touch panel
62B: sheet
66: cassette fixing mechanism
66A: slide groove
66B: fixing portion
66C: key lock
72: shielding plate
73: adjustment mechanism
76: lamp
77: reflective mirror
78: lighting circuit
156: arm
156A: vertical support portion
156B: horizontal arm portion
AX1: rotation axis
AX2: rotation axis
AX3: axis
AX4: axis
AX5: axis
AX6: axis
AX7: axis
BC: center position
C1: axle
D1: distance
D2: length
F: X-ray focus
H: object
L1: distance
L2: distance
ST: medical staff
α: angle

What is claimed is:

1. A mobile radiation generation apparatus comprising:
a carriage unit that includes a front wheel and a rear wheel and is run by rotation of the front wheel and the rear wheel about axles, the front wheel and the rear wheel being casters, each caster independently swiveling about a swivel axis extending in a vertical direction perpendicular to the respective axle;
an arm unit that has a free end attached to a radiation emitting unit and rotates about a rotation axis parallel to the swivel axes with respect to the carriage unit, using a base end as a base point;
a rotation locking mechanism that locks the rotation of the rear wheel about the respective axle;
a swivel locking mechanism that locks the swivel of the rear wheel about the respective swivel axis; and
a front pedal that is provided in the carriage unit so as to protrude forward from the carriage unit and is used to operate both the rotation locking mechanism and the swivel locking mechanism at the same time.

2. The mobile radiation generation apparatus according to claim 1,
wherein the rear wheel includes two or more casters and each of the casters is capable of swiveling independently.

3. The mobile radiation generation apparatus according to claim 1,
wherein the mobile radiation generation apparatus has a first lock mode in which the rotation locking mechanism and the swivel locking mechanism are operated for the rear wheel and a second lock mode in which the rotation locking mechanism is not operated and only the swivel locking mechanism is operated.

4. The mobile radiation generation apparatus according to claim 2,
wherein the mobile radiation generation apparatus has a first lock mode in which the rotation locking mechanism and the swivel locking mechanism are operated for the rear wheel and a second lock mode in which the rotation locking mechanism is not operated and only the swivel locking mechanism is operated.

5. The mobile radiation generation apparatus according to claim 3,
wherein the front pedal selectively switches the first lock mode and the second lock mode.

6. The mobile radiation generation apparatus according to claim 4,
wherein the front pedal selectively switches the first lock mode and the second lock mode.

7. The mobile radiation generation apparatus according to claim 3, further comprising:
a rear pedal that is provided in the carriage unit so as to protrude backward from the carriage unit and has at least some of the functions of the front pedal.

8. The mobile radiation generation apparatus according to claim 4, further comprising:
a rear pedal that is provided in the carriage unit so as to protrude backward from the carriage unit and has at least some of the functions of the front pedal.

9. The mobile radiation generation apparatus according to claim 5, further comprising:
a rear pedal that is provided in the carriage unit so as to protrude backward from the carriage unit and has at least some of the functions of the front pedal.

10. The mobile radiation generation apparatus according to claim 6, further comprising:
a rear pedal that is provided in the carriage unit so as to protrude backward from the carriage unit and has at least some of the functions of the front pedal.

11. The mobile radiation generation apparatus according to claim 7,
wherein the rear pedal has the same functions as the front pedal.

12. The mobile radiation generation apparatus according to claim 8,
wherein the rear pedal has the same functions as the front pedal.

13. The mobile radiation generation apparatus according to claim 9,
wherein the rear pedal has the same functions as the front pedal.

14. The mobile radiation generation apparatus according to claim 10,
wherein the rear pedal has the same functions as the front pedal.

15. The mobile radiation generation apparatus according to claim 11,
wherein the front pedal and the rear pedal are selectively switchable among three positions, that is, an initial position, an upper position that is above the initial position in a vertical direction, and a lower position that is below the initial position in the vertical direction, and
the mobile radiation generation apparatus further comprises a front and rear pedal operative association mechanism that, in a case in which one of the front pedal and the rear pedal is moved to any one of the three positions, moves the other pedal to the same position in operative association with the one pedal.

16. The mobile radiation generation apparatus according to claim 12,
wherein the front pedal and the rear pedal are selectively switchable among three positions, that is, an initial position, an upper position that is above the initial position in a vertical direction, and a lower position that is below the initial position in the vertical direction, and the mobile radiation generation apparatus further comprises a front and rear pedal operative association mechanism that, in a case in which one of the front pedal and the rear pedal is moved to any one of the three positions, moves the other pedal to the same position in operative association with the one pedal.

17. The mobile radiation generation apparatus according to claim 13, wherein the front pedal and the rear pedal are selectively switchable among three positions, that is, an initial position, an upper position that is above the initial position in a vertical direction, and a lower position that is below the initial position in the vertical direction, and the mobile radiation generation apparatus further comprises a front and rear pedal operative association mechanism that, in a case in which one of the front pedal and the rear pedal is moved to any one of the three positions, moves the other pedal to the same position in operative association with the one pedal.

18. The mobile radiation generation apparatus according to claim 14, wherein the front pedal and the rear pedal are selectively switchable among three positions, that is, an initial position, an upper position that is above the initial position in a vertical direction, and a lower position that is below the initial position in the vertical direction, and the mobile radiation generation apparatus further comprises a front and rear pedal operative association mechanism that, in a case in which one of the front pedal and the rear pedal is moved to any one of the three positions, moves the other pedal to the same position in operative association with the one pedal.

* * * * *